US012570894B2

(12) United States Patent
Miyazaki et al.

(10) Patent No.: US 12,570,894 B2
(45) Date of Patent: Mar. 10, 2026

(54) PHOTOCHROMIC COMPOUND AND CURABLE COMPOSITION CONTAINING THE PHOTOCHROMIC COMPOUND

(71) Applicant: TOKUYAMA CORPORATION, Shunan (JP)

(72) Inventors: Masayuki Miyazaki, Shunan (JP); Junji Takenaka, Shunan (JP); Srinivas Venu, Shunan (JP); Junji Momoda, Shunan (JP); Katsuhiro Mori, Shunan (JP)

(73) Assignee: TOKUYAMA CORPORATION, Shunan (JP)

( * ) Notice: Subject to any disclaimer, the term of this patent is extended or adjusted under 35 U.S.C. 154(b) by 615 days.

(21) Appl. No.: 17/768,762

(22) PCT Filed: Oct. 14, 2020

(86) PCT No.: PCT/JP2020/038753
§ 371 (c)(1),
(2) Date: Apr. 13, 2022

(87) PCT Pub. No.: WO2021/075456
PCT Pub. Date: Apr. 22, 2021

(65) Prior Publication Data
US 2023/0242808 A1 Aug. 3, 2023

(30) Foreign Application Priority Data
Oct. 17, 2019 (JP) ................................ 2019-190604

(51) Int. Cl.
*C09K 9/02* (2006.01)
*C07D 311/96* (2006.01)
(Continued)

(52) U.S. Cl.
CPC .............. *C09K 9/02* (2013.01); *C07D 311/96* (2013.01); *C07D 497/10* (2013.01);
(Continued)

(58) Field of Classification Search
CPC .... C09K 9/02; C09K 2211/1018; C09D 4/06; C09D 7/63; C07D 311/96; C07D 497/10;
(Continued)

(56) References Cited

U.S. PATENT DOCUMENTS 5,952,515 A * 9/1999 Melzig .................... C09K 9/02 548/215
2006/0226402 A1* 10/2006 Kim ........................ C09B 57/02 252/586

(Continued)

FOREIGN PATENT DOCUMENTS

EP 2 479 171 A1 7/2012
JP 64-38063 A 2/1989

(Continued)

OTHER PUBLICATIONS

Extended European Search Report for corresponding European Application No. 20877321.8, dated Oct. 26, 2023.

(Continued)

*Primary Examiner* — Bijan Ahvazi
(74) *Attorney, Agent, or Firm* — Birch, Stewart, Kolasch & Birch, LLP

(57) ABSTRACT

A photochromic compound of the present invention comprises at least two monovalent photochromic basic structure groups PC including a T-type photochromic moiety, the photochromic basic structure groups being bonded to an organic group having a non-SO aromatic ring containing neither a sulfur atom nor an oxygen atom.

7 Claims, 1 Drawing Sheet

(51) Int. Cl.

| | |
|---|---|
| ***C07D 497/10*** | (2006.01) |
| ***C07F 7/08*** | (2006.01) |
| ***C09D 4/06*** | (2006.01) |
| ***C09D 7/63*** | (2018.01) |
| ***G02B 1/04*** | (2006.01) |
| ***G02B 1/10*** | (2015.01) |
| ***G02B 5/23*** | (2006.01) |
| *C08K 5/1545* | (2006.01) |
| *C08K 5/357* | (2006.01) |
| *C08K 5/378* | (2006.01) |
| *C08K 5/46* | (2006.01) |
| *C08K 5/5435* | (2006.01) |
| *C08K 5/548* | (2006.01) |

(52) U.S. Cl.

CPC .............. *C07F 7/0812* (2013.01); *C09D 4/06* (2013.01); *C09D 7/63* (2018.01); *G02B 1/041* (2013.01); *G02B 1/10* (2013.01); *G02B 5/23* (2013.01); *C08K 5/1545* (2013.01); *C08K 5/357* (2013.01); *C08K 5/378* (2013.01); *C08K 5/46* (2013.01); *C08K 5/5435* (2013.01); *C08K 5/548* (2013.01); *C09K 2211/1018* (2013.01)

(58) Field of Classification Search

CPC ......... C07F 7/0812; G02B 1/041; G02B 1/10; G02B 5/23; C08K 5/46

See application file for complete search history.

(56) References Cited

U.S. PATENT DOCUMENTS

| | | | | |
|---|---|---|---|---|
| 2007/0215844 | A1* | 9/2007 | Momoda | C07D 311/96 252/582 |
| 2011/0059545 | A1* | 3/2011 | Salman | G01D 7/005 548/409 |
| 2011/0287549 | A1* | 11/2011 | Salman | C09K 9/02 427/591 |
| 2012/0136148 | A1* | 5/2012 | Lu | C09K 9/02 549/382 |
| 2020/0190106 | A1* | 6/2020 | Miyazaki | C08K 5/357 |
| 2021/0032532 | A1 | 2/2021 | Miyazaki et al. | |
| 2023/0109024 | A1 | 4/2023 | Miyazaki et al. | |

FOREIGN PATENT DOCUMENTS

| | | | | | |
|---|---|---|---|---|---|
| JP | S6438063 | A | * | 2/1989 | C07D 207/44 |
| JP | 2005-508897 | A | | 4/2005 | |
| JP | 2007-526223 | A | | 9/2007 | |
| JP | 2010-518360 | A | | 5/2010 | |
| JP | 2012-517518 | A | | 8/2012 | |
| JP | 2018-62496 | A | | 4/2018 | |
| JP | 2018062496 | A | * | 4/2018 | C07D 311/96 |
| JP | 2019-182866 | A | | 10/2019 | |
| KR | 10-2011-0115243 | A | | 10/2011 | |
| KR | 1020110115243 | | * | 10/2011 | C09K 9/02 |
| KR | 10-2012-0053988 | A | | 5/2012 | |
| WO | WO-0039245 | A1 | * | 7/2000 | C07D 405/14 |
| WO | WO 03/020718 | A1 | | 3/2003 | |
| WO | WO 2005/005570 | A1 | | 1/2005 | |
| WO | WO 2006/110513 | A1 | | 10/2006 | |
| WO | WO 2008/090045 | A1 | | 7/2008 | |
| WO | WO 2010/092030 | A1 | | 8/2010 | |
| WO | WO 2019/013249 | A1 | | 1/2019 | |
| WO | WO 2021/172511 | A1 | | 9/2021 | |

OTHER PUBLICATIONS

Ikezawa et al., "Thiophene-substituted phenoxyl-imidazolyl radical complexes with high photosensitivity", Chemical Communications, 2016, vol. 52, No. 12, pp. 2465-2468, DOI: 10.1039/c5cc10133f, total 6 pages.

International Search Report for PCT/JP2020/038753 mailed on Dec. 15, 2020.

Mutoh et al., "Recent advances in visible-light-responsive photochromic molecules", Koukagaku (Photochemistry), 2018, vol. 49, No. 3, pp. 136-143.

Zhao et al., "Synthesis and Photochromism of Novel Phenylene-Linked Photochromic Bispyrans", Organic Letters, 2006, vol. 8, No. 1, pp. 99-102, DOI: 10.1021/01052587y, total 4 pages.

English translation of the Japanese Office Action for corresponding Japanese Application No. 2021-552409, dated Jan. 7, 2025.

English translation of the Korean Office Action for corresponding Korean Application No. 10-2022-7009424, dated Dec. 13, 2024.

European Communication pursuant to Article 94(3) EPC for corresponding European Application No. 20 877 321.8, dated Apr. 22, 2025.

* cited by examiner

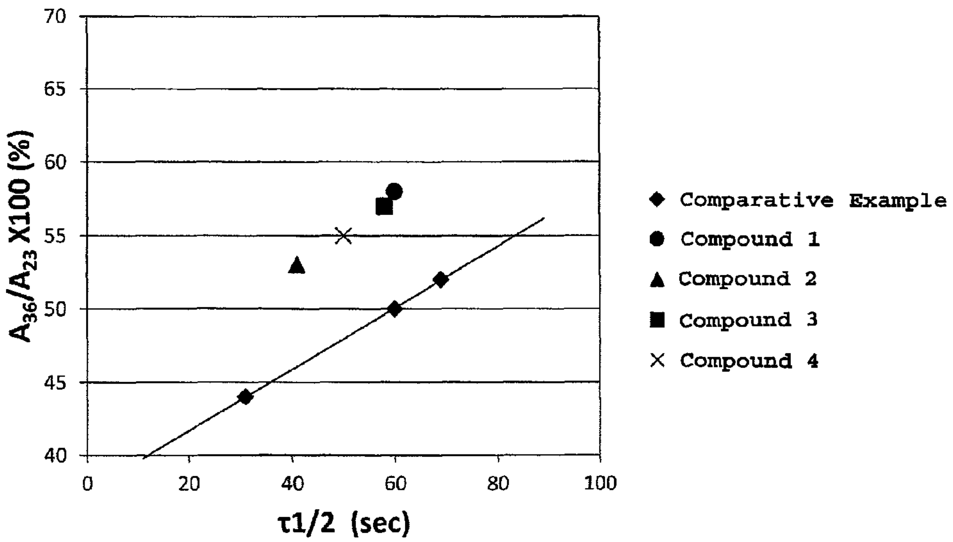
70
65
60
55
50
45
40
0
20
40
60
80
100
$A_{36}/A_{23}$ X100 (%)
τ1/2 (sec)
Comparative Example
Compound 1
Compound 2
Compound 3
Compound 4

PHOTOCHROMIC COMPOUND AND CURABLE COMPOSITION CONTAINING THE PHOTOCHROMIC COMPOUND

TECHNICAL FIELD

The present invention relates to a novel photochromic compound with temperature dependence.

BACKGROUND ART

Photochromic compounds are compounds that can undergo a reversible transformation between two isomers with different absorption spectra when irradiated with ultraviolet-containing light such as sunlight or light from a mercury lamp. Usually, when a colorless compound in a decolored state is irradiated with ultraviolet rays, it rapidly undergoes isomerization (color development reaction) involving a color change to a colored compound in a color developed state. Upon isomerization from the color developed state to the decolored state (fading reaction), some photochromic compounds return to the original colorless state not only by light with a specific wavelength but also by heat. Such photochromic compounds are referred to as T-type photochromic compounds, which have been well studied and developed especially as a photochromic lens material.

Such a photochromic compound for use for a photochromic lens is usually required to possess the following properties:

(I) The degree of coloration in a visible light region before ultraviolet irradiation (initial coloration) is low;

(II) The color optical density is saturated quickly after the start of ultraviolet irradiation;

(III) The speed of return to the original state after the stop of ultraviolet irradiation (fading rate) is high;

(IV) The durability against the repetition of this reversible action is favorable; and (V) The dissolubility in a monomer composition which will serve as a host material after curing is high to achieve high dispersibility in the host material to be used.

A number of chromene compounds have been studied as photochromic compounds satisfying these properties.

With the popularization of photochromic compounds in recent years, they are expected to satisfy further properties that have not been requested.

In general, T-type photochromic compounds are known to have a trade-off relationship between the fading rate and the color optical density and, thus, be easily affected by ambient environmental temperature (have large temperature dependence) For example, when a T-type photochromic compound is used under high temperature as in summer with the hot sun, it is subject to fading and declines in color optical density. As a possible countermeasure, a larger amount of the photochromic compound may be blended to increase the color optical density, thereby obtaining a photochromic lens having high color optical density even under high temperature. However, as the blending amount increases, a proportional relationship between the blending amount and the color optical density usually collapses. Thus, there is a limit to this countermeasure in terms of cost and the dissolubility of the photochromic compound itself.

As described above, a sufficient improvement has not yet been made in T-type photochromic compounds for use under high temperature as in summer by merely increasing the blending amount thereof. Under the circumstances, there has been a growing demand especially for the development of a photochromic compound having high color optical density even under high temperature as in summer.

In order to achieve a T-type photochromic compound having high color optical density under high temperature, it is necessary to improve the thermal stability in the colored state. However, this causes a decrease in the fading rate because of the trade-off relationship between the fading rate and the color optical density. It is usually difficult to achieve both a fast fading rate and small temperature dependence.

In order to improve this problem, the present inventors propose a chromene compound having substituents at specific positions (see Patent Document 1). This compound has relatively small temperature dependence.

However, the chromene compound described in Patent Document 1 results in limited color tones because it has substituents at specific positions. In general, chromene compounds are molecularly designed to satisfy desired photochromic properties for their purposes by incorporating various substituents. Thus, limiting substituents makes it possible to achieve a chromene compound with smaller temperature dependence, but at the same time impairs other properties, making it difficult to obtain satisfactory color tones, for example.

Further, Patent Document 2 proposes a photochromic compound in which two naphthopyran skeletons are linked by an aromatic ring group (SO aromatic ring group) containing a sulfur atom (S) and an oxygen atom (O). However, this photochromic compound has low photochromic durability. In addition, Patent Document 2 gives no consideration to temperature dependence.

PRIOR ART DOCUMENTS

Patent Documents

Patent Document 1: JP 2018-062496 A

Patent Document 2: JP 2005-508897 A

SUMMARY OF THE INVENTION

Problems to be Solved by the Invention

Therefore, an object of the present invention is to provide a photochromic compound that has small temperature dependence, exhibits high color optical density even under high temperature as in summer, is capable of keeping constant color tones at the time of color development and fading, and is excellent in photochromic durability.

Another object of the present invention is to provide a curable composition, an optical article, and a polymer molded article containing the above-described photochromic compound.

Means for Solving the Problems

The present inventors have examined compounds with a T-type photochromic moiety (basic skeleton) about their various structures, substituents, and the positions and combinations of the substituents. As a result, it has been found that temperature dependence is improved when groups having a T-type photochromic moiety are linked via a specific aromatic ring group. Thus, the present invention has been completed.

The present invention provides a photochromic compound comprising at least two monovalent photochromic basic structural groups PC including a T-type photochromic moiety, the photochromic basic structural groups being bonded to an organic group having a non-SO aromatic ring containing neither a sulfur atom nor an oxygen atom.

The following are suitable embodiments of the photochromic compound of the present invention.

(A) The photochromic compound is represented by Formula (1) below.

$$[PC-L]_m-R^3 \quad (1)$$

In the formula, m is an integer of 2 or more,

PC is the monovalent photochromic basic structural group, provided that at least one of L and $R^3$ contains the non-SO aromatic ring, L is a divalent organic group terminally bonded to the PC or a direct bonding, $R^3$ is an m-valent organic group or a direct bonding, and when $R^3$ is a direct bonding, m is 2 and L is a divalent organic group containing the non-SO aromatic ring.

(B) The m-valent organic group represented by above $R^3$ is at least one selected from a non-SO aromatic ring group; a saturated or unsaturated hydrocarbon group having 1 to 15 carbon atoms; a saturated or unsaturated aliphatic ring group that has 3 to 20 carbon atoms and may have a heteroatom in the aliphatic ring; a polyvalent silylene group that has 1 to 3 silicon atoms and has, as a substituent, at least one selected from an alkyl group having 1 to 15 carbon atoms, an alkoxy group having 1 to 15 carbon atoms, or a non-SO aromatic ring group having 6 to 30 carbon atoms; an oxygen atom or a sulfur atom (m=2); or a polyvalent amino group.

(C) The photochromic compound is represented by Formula (1a) below.

$$[PC-(R^1)_n-R^2]_m-R^3 \quad (1a)$$

In the formula, m, PC and $R^3$ are the same as those in the Formula (1), n is a number of 1 to 5, $-(R^1)n-R^2-$ is a divalent organic group corresponding to L in the Formula (1), $R^1$ is a direct bonding or a divalent non-SO aromatic ring group having 6 to 30 carbon atoms, and $R^2$ is a group that links $R^1$ and $R^3$ in the Formula (1) and is a direct bonding or a divalent organic group selected from the following:

a divalent acyclic saturated or unsaturated hydrocarbon group having 1 to 15 carbon atoms;

a divalent saturated or unsaturated aliphatic ring group that has 3 to 20 carbon atoms and may have a heteroatom in the aliphatic ring;

an oxygen atom or a sulfur atom;

a divalent amino group; or a silylene group that has 1 to 3 silicon atoms and has, as a substituent, at least one selected from an alkyl group having 1 to 15 carbon atoms, an alkoxy group having 1 to 15 carbon atoms, or a non-SO aromatic ring group having 6 to 30 carbon atoms.

(D) The T-type photochromic moiety included in the photochromic basic structural groups PC has at least one basic skeleton selected from the group consisting of a naphthopyran moiety, a spirooxazine moiety, and a spiropyran moiety.

(E) The T-type photochromic moiety is a naphthopyran moiety that has an indenonaphthopyran basic skeleton.

(F) The organic groups including the above group $R^3$ bonded to the PC have a molecular weight per PC of less than 1000.

(G) The monovalent photochromic basic structural groups PC are represented by Formula (2) below.

(2)

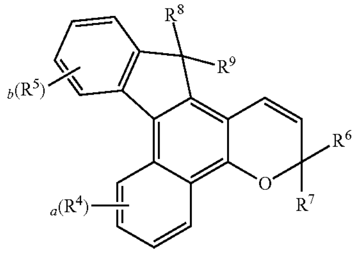

In the formula, a is an integer of 0 to 4, b is an integer of 0 to 4, $R^4$ and $R^3$ are each the following group:

a hydroxyl group;

an alkyl group;

a cycloalkyl group;

an alkoxy group;

an amino group;

a cyano group;

a halogen atom;

a nitro group;

a formyl group;

a hydroxycarbonyl group;

an alkylcarbonyl group;

an alkoxycarbonyl group;

an aryl group;

a heterocyclic group;

an alkylthio group;

a cycloalkylthio group;

an arylthio group;

an aralkyl group;

an aralkoxy group;

an aryloxy group;

a thiol group;

an alkoxyalkylthio group;

a group represented by Formula (X) below:

(X)

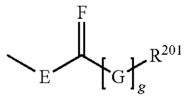

wherein E is an oxygen atom or $NR^{101}$, and $R^{101}$ is a hydrogen atom or an alkyl group, F is an oxygen atom or a sulfur atom, $R^{201}$ is a hydrogen atom, an alkyl group, or a cycloalkyl group, G is an oxygen atom, a sulfur atom, or $NR^{202}$, wherein $R^{202}$ is a hydrogen atom, an alkyl group, a cycloalkyl group, an aryl group, or a heteroaryl group, and when G is an oxygen atom or a sulfur atom, $R^{201}$ is a group other than a hydrogen atom, and g is an integer of 0 or 1; or a group represented by formula (Y) below:

(Y)

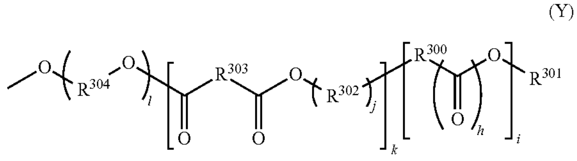

wherein $R^{300}$ is an alkylene group or a silylene group having an alkyl group or an aryl group as a substituent, $R^{301}$ is an alkyl group or an aryl group, $R^{302}$, $R^{303}$ and $R^{304}$ are each an alkylene group, h, j, k and 1 are each an integer of 0 or 1, and i is an integer of 2 to 200; the plural i may be expressed in the same or different units, when a plurality of the $R^4$ or $R^5$ are present depending on the value of a or b, the plural $R^4$ or $R^5$ may be the same or different from each other; when two $R^4$ or $R^5$ are present adjacent to each other, these two adjacent $R^4$ or $R^5$ together may form, with carbon atoms to which the $R^4$ or $R^5$ are bonded, a ring that may contain an oxygen atom, a carbon atom, a sulfur atom, or a nitrogen atom, $R^6$ and $R^7$ are each an aryl group or a heteroaryl group, provided that one of the $R^6$ and $R^7$ is a direct bonding to an organic group, $R^8$ and $R^9$ are each the following group:

a hydrogen atom;
a hydroxyl group;
an alkyl group;
a cycloalkyl group;
an alkoxy group;
an alkoxyalkyl group;
a formyl group;
a hydroxycarbonyl group;
an alkylcarbonyl group;
an alkoxycarbonyl group;
a halogen atom;
an aralkyl group;
an aralkoxy group;
an aryl group;
an aryloxy group;
a heterocyclic group; or
the group represented by Formula (Y), and the $R^8$ and $R^9$ together may form, with carbon atoms in the 13-position to which the $R^8$ and $R^9$ are bonded, an aliphatic ring having 3 to 20 carbon atoms, a fused polycyclic ring in which the aliphatic ring is fused with an aromatic ring or an aromatic heterocyclic ring, a 3- to 20-membered heterocyclic ring, or a fused polycyclic ring in which the heterocyclic ring is fused with an aromatic ring or an aromatic heterocyclic ring.

(H) The $R^8$ and $R^9$ in Formula (2) together form, with the carbon atoms in the 13-position to which the $R^8$ and $R^9$ are bonded, an aliphatic ring having 3 to 20 carbon atoms, a fused polycyclic ring in which the aliphatic ring is fused with an aromatic ring or an aromatic heterocyclic ring, a 3- to 20-membered heterocycle ring, or a fused polycyclic ring in which the heterocyclic ring is fused with an aromatic ring or an aromatic heterocyclic ring.

(I) The aliphatic ring formed by the $R^8$ and $R^9$ in Formula (2) together is a cyclopentane ring, a cyclohexane ring, a cycloheptane ring, a cyclooctane ring, a cyclononane ring, a cyclodecane ring, a cycloundecane ring, a cyclododecane ring, or a spirodicyclohexane ring, and the ring may have one to ten alkyl groups having 1 to 3 carbon atoms or cycloalkyl groups having 5 to 7 carbon atoms as substituents or may be fused with a cycloalkyl group having 5 to 7 carbon atoms.

The present invention also provides a photochromic curable composition comprising the above-described photochromic compound and a polymerizable compound.

The present invention further provides a photochromic optical article formed by polymerization of the aforementioned photochromic curable composition, a polymer molded article in which the above-described photochromic compound is dispersed, and an optical article coated with a polymer film in which the above-described photochromic compound is dispersed.

Effects of the Invention

T-type photochromic compounds have temperature dependence such that they change from a color developed state to a decolored state by temperature. The photochromic compound of the present invention has a molecular structure in which a plurality of T-type photochromic molecules are linked via specific aromatic rings. This molecular structure contributes to reducing temperature dependence of T-type photochromic compounds and keeping a stable color tone even under high temperature as in summer and the like.

The reduction in temperature dependence due to the molecular structure has been achieved as a result of many experiments. The reason for this is still unknown, but the present inventors presume as follows.

When a plurality of T-type photochromic molecules are bonded by rigid bonds like aromatic rings that allow for molecular interactions such as Π-Πstacking, the T-type photochromic molecules are motionally restricted and tend to get close to one another. As a result, a fading reaction is less likely to occur, so that a color developed state is maintained even in a high temperature condition as compared with a case where individual photochromic molecules are present independently of one another.

Further, since the reduction in temperature dependence in the present invention is not achieved by incorporating specific substituents into a photochromic compound, the color tone is not limited.

The aromatic ring between a plurality of the T-type photochromic molecules needs to be a non-SO aromatic ring containing neither a sulfur atom nor an oxygen atom. As shown in Examples below, when a heteroaromatic ring containing a sulfur atom (S) or an oxygen atom (O) serves as a linking group, photochromic durability decreases.

The photochromic compound of the present invention can be used to produce a photochromic lens with small temperature dependence such that it has high color optical density even under high temperature as in summer.

BRIEF DESCRIPTION OF THE DRAWINGS

FIG. 1: a chart showing relationships between temperature dependence and a fading half-life of compounds in Examples and Comparative Examples.

MODE FOR CARRYING OUT THE INVENTION

A photochromic compound of the present invention has a structure in which at least two monovalent photochromic basic structural groups PC containing a T-type photochromic moiety are bonded via an organic group having a non-SO aromatic ring.

<Monovalent Photochromic Basic Structural Group PC>

The monovalent photochromic basic structural group PC of the present invention has a photochromic moiety as a basic skeleton of a T-type photochromic compound. The presence of the photochromic moiety contributes to imparting temperature dependence specific to a T-type photochromic compound, allowing the compound to be thermally isomerized from a color developed state to a decolored state.

The T-type photochromic moiety of the present invention preferably induces a molecular conformational change upon isomerization. More preferably, the T-type photochromic moiety is a naphthopyran moiety, a spirooxazine moiety, or a spiropyran moiety, for example. Among them, a naphthopyran moiety is still more preferable, and an indenonaphthopyran moiety, particularly indeno[2,1-f]naphtho[1,2-b]pyran, is most preferable as a basic skeleton. It is believed that these moieties as a basic skeleton bonded via a specific aromatic ring group effectively suppress isomerization due to the conformational change and, accordingly, reduce temperature dependence.

The monovalent photochromic basic structural group PC having an indeno[2,1-f]naphtho[1,2-b]pyran basic skeleton as mentioned above is represented by Formula (2) below.

(2)

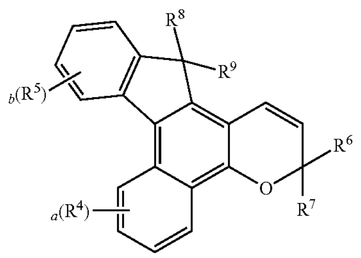

In this photochromic basic structural group PC, a structure from which groups $R^4$ to $R^9$ have been removed is the indeno[2,1-f]naphtho[1,2-b]pyran basic skeleton as a T-type photochromic moiety.

In the Formula (2), a, which represents the number of the groups $R^4$, is an integer of 0 to 4, and b, which represents the number of the groups $R^5$, is an integer of 0 to 4.

$R^4$ and $R^5$ are each the following group:

- a hydroxyl group;
- an alkyl group, especially one having 1 to 6 carbon atoms;
- a cycloalkyl group, especially one having 3 to 8 carbon atoms;
- an alkoxy group, especially one having 1 to 6 carbon atoms;
- an amino group;
- a cyano group;
- a halogen atom;
- a nitro group;
- a formyl group;
- a hydroxycarbonyl group;
- an alkylcarbonyl group, especially one having 2 to 7 carbon atoms;
- an alkoxycarbonyl group, especially one having 1 to 7 carbon atoms;
- an aryl group, especially one having 6 to 12 carbon atoms;
- a heterocyclic group, especially one having a nitrogen atom as a ring member atom;
- an alkylthio group, especially one having 1 to 6 carbon atoms;
- a cycloalkylthio group, especially one having 3 to 8 carbon atoms;
- an arylthio group, especially one having 6 to 12 carbon atoms;
- an aralkyl group, especially one having 7 to 11 carbon atoms;
- an aralkoxy group, especially one having 7 to 11 carbon atoms;
- an aryloxy group, especially one having 6 to 12 carbon atoms;
- a thiol group;
- an alkoxyalkylthio group, especially one having 1 to 6 carbon atoms; or
- a group represented by Formula (X) or Formula (Y) below.

(X)

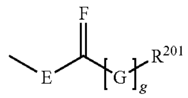

(Y)

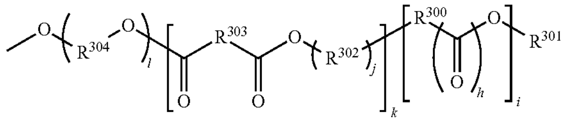

In Formula (X),

E is an oxygen atom or $NR^{101}$ ($R^{101}$ is a hydrogen atom or an alkyl group);

F is an oxygen atom or a sulfur atom;

G is an oxygen atom, a sulfur atom or $NR^{202}$ ($R^{202}$ is a hydrogen atom, an alkyl group, a cycloalkyl group, an aryl group or a heteroaryl group);

g is an integer of 0 or 1; and $R^{201}$ is a hydrogen atom, an alkyl group, a cycloalkyl group, an aryl group or a heteroaryl group, while $R^{201}$ is a group other than a hydrogen atom when G is an oxygen atom or a sulfur atom.

In Formula (Y), $R^{300}$ is an alkylene group or a silylene group having an alkyl group or an aryl group as a substituent;

$R^{301}$ is an alkyl group or an aryl group;

$R^{302}$, $R^{303}$ and $R^{304}$ are each an alkylene group;

h, j, k and 1 are each an integer of 0 or 1; i is an integer of 2 to 200; and the plural i may be expressed in the same or different units.

A plurality of $R^4$ or $R^5$ are to be present depending on the value of a or b. These groups may be the same or different from each other. Further, when two $R^4$ or $R^5$ are present adjacent to each other, these two adjacent $R^4$ or $R^5$ together may form a ring together with the carbon atoms to which the $R^4$ or $R^5$ are bonded. This ring may contain an oxygen atom, a carbon atom, a sulfur atom or a nitrogen atom as a ring member atom.

In Formula (X), E is preferably $NR^{101}$, and $R^{101}$ is preferably a hydrogen atom or an alkyl group having 1 to 6 carbon atoms.

F is preferably an oxygen atom.

G is suitably NH; in other words, $R^{202}$ is suitably a hydrogen atom. Alternatively, G is suitably an oxygen atom.

$R^{201}$ is preferably an alkyl group having 1 to 6 carbon atoms or an aryl group having 6 to 12 carbon atoms.

Particularly suitable groups represented by Formula (X) are as follows.

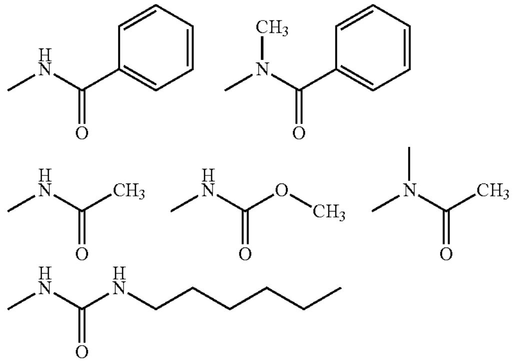

In Formula (Y), $R^{300}$ is preferably an alkylene group having 1 to 6 carbon atoms or a silylene group having an alkyl group with 1 to 6 carbon atoms as a substituent.

$R^{301}$ is preferably an alkyl group having 1 to 6 carbon atoms.

$R^{302}$ is suitably an alkylene group having 1 to 6 carbon atoms.

$R^{303}$ is preferably an alkylene group having 1 to 6 carbon atoms.

$R^{304}$ is preferably an alkylene group having 1 to 6 carbon atoms.

Further, i, which is an integer of 2 to 200, is a number preferably in a range of 5 to 100, more preferably in a range of 8 to 75, and most preferably in a range of 10 to 70.

Particularly suitable groups represented by Formula (Y) are represented by the following formulas.

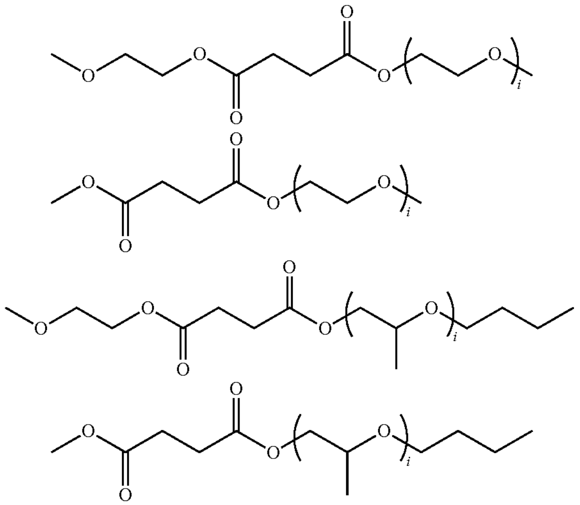

-continued

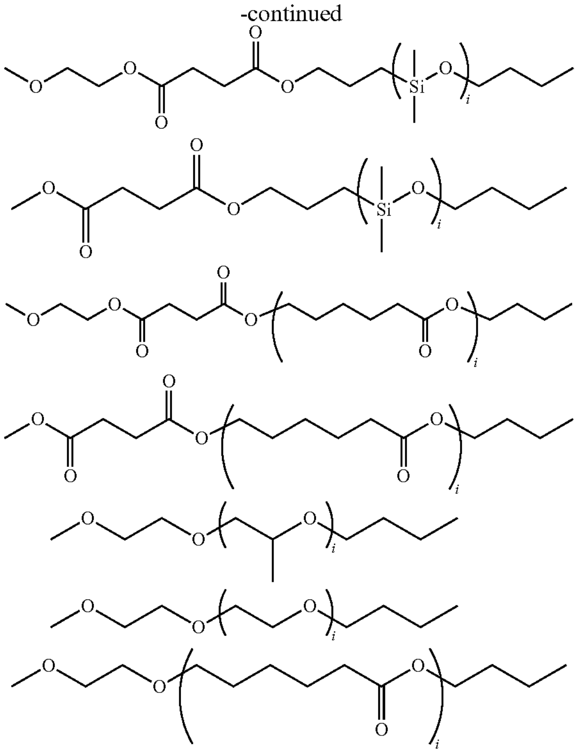

Each of the groups above can be bonded to a substituent such as a halogen atom and may have such a substituent as long as it does not inhibit photochromic properties. Further, the chain group such as an alkyl group may be linear or branched.

Further, unless otherwise specified, not only the groups above but also any group or ring capable of having a substituent that does not inhibit photochromic properties may have such a substituent. Further, the chain group may be linear or may have branches.

In the present invention, $R^4$ is preferably an alkyl group having 1 to 6 carbon atoms, an alkoxy group having 1 to 6 carbon atoms, an amino group, a heterocyclic group, an alkylthio group, an arylthio group, or an aryl group having 6 to 12 carbon atoms. In particular, it is more preferred that this group is present in the 6-position and/or the 7-position. Further, it is preferred that $R^4$ is present in the 6- and 7-positions of the indeno[2,1-f]naphtho[1,2-b]pyran, and these $R^4$ together form an aliphatic ring which may contain an oxygen atom, a nitrogen atom or a sulfur atom. At this time, it is preferred that the number of atoms of the aliphatic ring that contains an oxygen atom, a nitrogen atom or a sulfur atom (the number of atoms including heteroatoms and carbon atoms to which $R^4$ in the 6- and 7-positions are bonded) is 5 to 8. The aliphatic ring may have a substituent, which is suitably an alkyl group having 1 to 6 carbon atoms.

$R^5$ is suitably a hydrogen atom (when b=0), an alkyl group having 1 to 6 carbon atoms, an alkoxy group having 1 to 6 carbon atoms, an aryl group having 6 to 12 carbon atoms, or an arylthio group. It is more preferable that $R^5$ is present in the 11-position of the indeno[2,1-f]naphtho[1,2-b]pyran, and is a hydrogen atom (when b=0), an alkyl group having 1 to 6 carbon atoms, an alkoxy group having 1 to 6 carbon atoms, an aryl group with 6 to 12 carbon atoms that may have a substituent, or an arylthio group.

In the Formula (2), one of $R^6$ and $R^7$ is a direct bonding to an organic group having a non-SO aromatic ring described below. It is considered that this moiety serving as a direct bonding allows for moderate control of the molecular motion of ring opening/closure and, accordingly, contributes to reducing temperature dependence.

$R^6$ and $R^7$ are each an aryl group or a heteroaryl group, provided that one of them is the direct bonding as described above.

$R^8$ and $R^9$ are each the following atom or group:

a hydrogen atom;

a hydroxyl group;

an alkyl group, especially one having 1 to 6 carbon atoms;

a cycloalkyl group, especially one having 3 to 8 carbon atoms;

an alkoxy group, especially one having 1 to 6 carbon atoms;

an alkoxyalkyl group;

a formyl group;

a hydroxycarbonyl group;

an alkylcarbonyl group, especially one having 2 to 7 carbon atoms;

an alkoxycarbonyl group, especially one having 1 to 7 carbon atoms;

a halogen atom;

an aralkyl group, especially one having 7 to 11 carbon atoms;

an aralkoxy group, especially one having 7 to 11 carbon atoms;

an aryl group, especially one having 6 to 12 carbon atoms;

an aryloxy group, especially one having 6 to 12 carbon atoms;

a heterocyclic group; or the group represented by Formula (Y), preferably the group specifically shown as $R^4$ and $R^5$.

$R^8$ and $R^9$ together may form, with the carbon atoms in the 13-position to which the $R^8$ and $R^9$ are bonded, an aliphatic ring having 3 to 20 carbon atoms, a fused polycyclic ring in which the aliphatic ring is fused with an aromatic ring or an aromatic heterocyclic ring, a 3- to 20-membered heterocyclic ring, or a fused polycyclic ring in which the heterocyclic ring is fused with an aromatic ring or an aromatic heterocyclic ring.

Particularly preferred examples of the ring to be formed by $R^8$ and $R^9$ together include aliphatic rings having 3 to 20 carbon atoms, such as a cyclopentane ring, a cyclohexane ring, a cycloheptane ring, a cyclooctane ring, a cyclononane ring, a cyclodecane ring, a cycloundecane ring, a cyclododecane ring, and a spirodicyclohexane ring. These aliphatic rings may preferably have 1 to 10 substituents such as alkyl groups having 1 to 3 carbon atoms or cycloalkyl groups having 5 to 7 carbon atoms. These aliphatic rings may be fused with a cycloalkyl group having 5 to 7 carbon atoms.

Particularly suitable examples of the aliphatic rings include those represented by the following formulas.

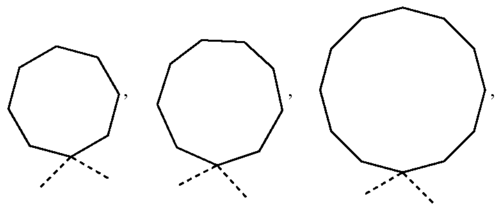

-continued

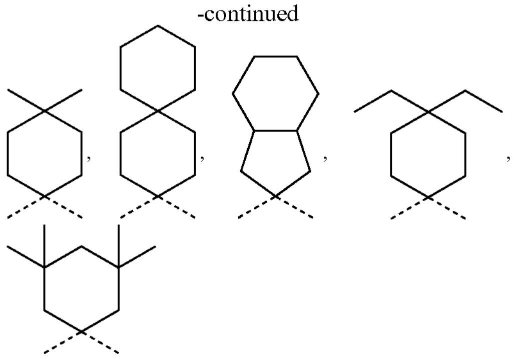

A plurality of the monovalent photochromic basic structural groups PC of Formula (2) having the T-type photochromic basic skeleton as described above are present in a molecule. The photochromic compound of the present invention has a structure in which the plurality of the photochromic basic structural groups PC are bonded via an organic group containing a non-SO aromatic ring described below.

<Organic Group Containing Non-SO Aromatic Ring>

The organic group to link the above-described monovalent photochromic basic structural groups PC in the present invention may have the following structure: The non-SO aromatic ring itself serves as a bonding group; the non-SO aromatic ring is present in the main chain of the aliphatic group; or a plurality of the non-SO aromatic rings are linked. The non-SO aromatic ring is an aromatic hydrocarbon ring or an aromatic heterocyclic ring containing neither a sulfur atom (S) nor an oxygen atom (O) therein. Since such an aromatic ring serves as a rigid bond that allows for molecular interactions such as r-r stacking, the molecular motion of the T-type photochromic moieties bonded to this bond is restricted, resulting in reduced temperature dependence. If the aromatic heterocyclic ring contains a sulfur atom (S) or an oxygen atom (O), photochromic durability decreases, while temperature dependence is reduced.

The non-SO aromatic ring of the present invention suitably has 6 to 30 carbon atoms or ring member atoms.

Examples of the aromatic hydrocarbon ring include: a benzene ring; a naphthalene ring; an anthracene ring; a phenanthrene ring; and a polycyclic aromatic ring in which any of these rings is further fused with a benzene ring or the like, such as a tetracene ring, a pentacene ring, a benzopyrene ring, a chrysene ring, a pyrene ring, or a triphenylene ring.

The aromatic heterocyclic ring is not particularly limited as long as it contains neither a sulfur atom nor an oxygen atom in the ring. Examples include a pyrrole ring, an indole ring, an isoindole ring, a pyridine ring, a pyrimidine ring, a quinazoline ring, a pyridazine ring, a cinnoline ring, a phthalazine ring, and a 1,2,3-, 1,2,4- or 1,3,5-triazine ring.

The non-SO aromatic ring of the present invention is particularly suitably a benzene ring or a polycyclic aromatic hydrocarbon ring in which a benzene ring is fused with one or a plurality of benzene rings.

The above-described organic group containing the non-SO aromatic ring in the present invention has a plurality of bonds, the positions of which are not particularly limited. Hereinafter, a description will be given of suitable examples of the molecular structure of the photochromic compound in which a plurality of the PCs are bonded via the organic group containing the non-SO aromatic ring.

<Suitable Molecular Structure of Photochromic Compound>

The photochromic compound in which a plurality of the T-type photochromic moieties are linked via the organic group containing the non-SO aromatic ring is represented by Formula (1) below.

$$[PC-L]_m-R^3 \quad (1)$$

In Formula (1), m is an integer of 2 or more, and PC is the monovalent photochromic basic structural group as described above.

As can be understood from this formula, m represents not only the valence (i.e., the number of the bonds) of $R^3$ but also the number of the PCs, i.e., the number of the T-type photochromic moieties (basic skeletons), contained in the molecule.

When m has a too high value, a reduction in temperature dependence as aimed in the present invention is less likely to be achieved. In addition, it becomes more difficult to produce a photochromic compound with a higher number of PCs contained in a molecule. For these reasons, the value of m is preferably not more than 20, more preferably not more than 10, even more preferably not more than 6, and most preferably 2 to 4.

In Formula (1), L and $R^3$ are each a linking group to link a plurality of the PCs. Thus, at least one of L and $R^3$ has to contain the non-SO aromatic ring. On this condition, $R^3$ and L are the following groups.

First, $R^3$ is an m-valent organic group or a direct bonding. When $R^3$ is a direct bonding, m is 2, and then L is a divalent group containing the non-SO aromatic ring. In other words, L in this case never serves as a direct bonding.

Alternatively, $R^3$ may be an m-valent organic group that does not contain the non-SO aromatic ring. Examples include the following groups:

- a saturated or unsaturated hydrocarbon group having 1 to 15 carbon atoms;
- a saturated or unsaturated aliphatic ring group having 3 to 20 carbon atoms, which may have a heteroatom in the aliphatic ring;
- a polysilylene group having 1 to 3 silicon atoms that has as a substituent at least one selected from an alkyl group having 1 to 15 carbon atoms, an alkoxy group having 1 to 15 carbon atoms, or a non-SO aromatic ring group having 6 to 30 carbon atoms;
- an oxygen atom or a sulfur atom (m=2); and
- an amino group.

In the present invention, $R^3$ is suitably a direct bonding, an m-valent non-SO aromatic ring group, an oxygen atom, a nitrogen atom, amethylene group, or a combination thereof. For example, an oxygen atom may be combined with a methylene group to form $-O-CH_2-$ and further with a methylene group to form a trivalent group such as $-O-CH<$.

In the present invention, $R^3$ preferably has a molecular weight of less than 200. When $R^3$ is larger, the motion of the photochromic moiety is less restricted, which tends to decrease the effect of reducing temperature dependence.

On the other hand, Lis a divalent organic group terminally bonded to the PC or a direct bonding. L may be any of divalent organic groups including not only a divalent non-SO aromatic ring group but also various organic groups other than SO aromatic ring groups. When L is a direct bonding, $R^3$ is a group including the non-SO aromatic ring group.

Further, L may suitably be a divalent group represented by the following formula:

$$-(R^1)n\text{-}R^2-$$

Accordingly, when L is the divalent organic group, the photochromic compound of General Formula (1) is represented by General Formula (1a) below.

$$[PC-(R^1)_n-R^2]_m-R^3 \quad (1a)$$

In Formula (1a), $-(R^1)n\text{-}R^2-$ corresponds to L as a divalent organic group in Formula (1), and m, PC and $R^3$ are the same as those in the above Formula (1).

Further, n is a number of 1 to 5, and $R^1$ is a direct bonding or a divalent non-SO aromatic ring group. When $R^1$ is a direct bonding, n is 1.

The non-SO aromatic ring group here is any of the above-described non-SO aromatic rings that have two bonds.

In the above Formula (1a), $R^1$ is a direct bonding or a non-SO aromatic ring group. When n is 2 or more, the plurality of $R^1$ may be different. When $R^1$ is a direct bonding, the PC is directly bonded to $R^2$.

When an excessively large number of the photochromic moieties are contained, molecular motion is excessively restricted, which tends to decrease the effect of reducing temperature dependence, though depending on the size of the photochromic moiety. In addition, it tends to be complicated to produce the photochromic compound itself. For these reasons, the number (n) of $R^1$ is preferably 5 or less, particularly 3 or less, more preferably 2 or less, and most suitably 1.

In the above Formula (1a), $R^2$, which is a group that bonds $R^1$ and $R^3$ in Formula (1), is a direct bonding or a divalent organic group selected from the following:

- a divalent acyclic saturated or unsaturated hydrocarbon group having 1 to 15 carbon atoms;
- a divalent aliphatic ring group having 3 to 20 carbon atoms, which may have a heteroatom in the aliphatic ring;
- an oxygen atom or a sulfur atom;
- a divalent amino group; and
- a silylene group having 1 to 3 silicon atoms that has as a substituent at least one selected from an alkyl group having 1 to 15 carbon atoms, an alkoxy group having 1 to 15 carbon atoms, or a non-SO aromatic ring group having 6 to 30 carbon atoms.

Among them, $R^2$ is preferably a direct bonding, a methylene group, an ethylene group, a vinylene group, an ethynylene group, a cyclohexylene group, an oxygen atom, a sulfur atom, a polyvalent amino group, an azo group, a silylene group, a tetramethylsiloxane group, a tetramethyldisililene group, or a combination group thereof (excluding the direct bonding). Particularly preferably, $R^2$ is a direct bonding, a methylene group, a vinylene group, an ethynylene group, a cyclohexylene group, an oxygen atom, a sulfur atom, apolyvalent amino group, an azo group, or a combination group thereof.

An example of the combination group is $-O-CH_2-$, which is a group composed of an oxygen atom and a methylene group.

As with $R^3$, when $R^2$ is large, the effect pf restricting the motion of the photochromic moiety is reduced, which tends to decrease the effect of reducing temperature dependence. Thus, $R^2$ has a molecular weight of less than 500, preferably less than 300, more preferably less than 150, and most preferably not more than 100.

As described above, in order to greatly reduce temperature dependence by restricting the motion of the photochromic moiety most effectively within a range that does not impair photochromic properties, it is suitable that the organic groups including the group $R^3$ bonded to the PC are not larger than a certain size. For example, the organic groups ($L+R^3$) preferably have a molecular weight per PC of less than 1000, particularly less than 750, more preferably less than 500, and most preferably less than 300. Thus, it is necessary to take into account the molecular weight when selecting the type ($R^3$, $R^1$, $R^2$) and number (m, n), etc. of the respective groups to perform molecular design.

The lowest molecular weight of the organic groups is 72, which is achieved when L is a direct bonding and $R^3$ is a benzene ring with all the hydrogen atoms substituted by PC (m=6).

In any case, in the photochromic compound of the present invention, the non-SO aromatic ring is always present between a plurality of the PCs.

Particularly suitable examples of the photochromic compound include those represented by the following formulas.

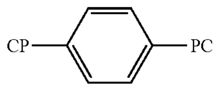
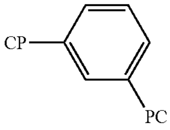
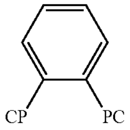
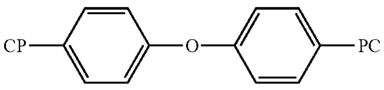
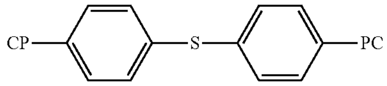
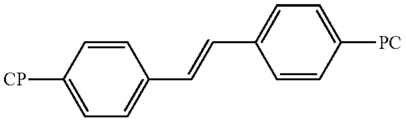
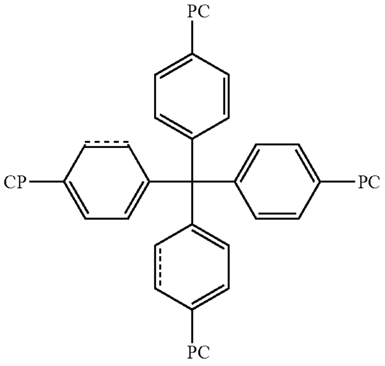
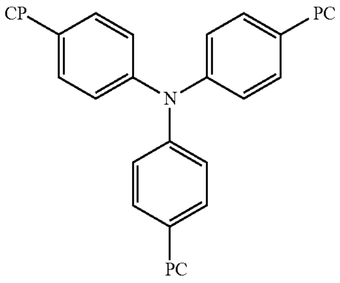
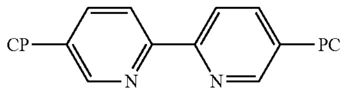
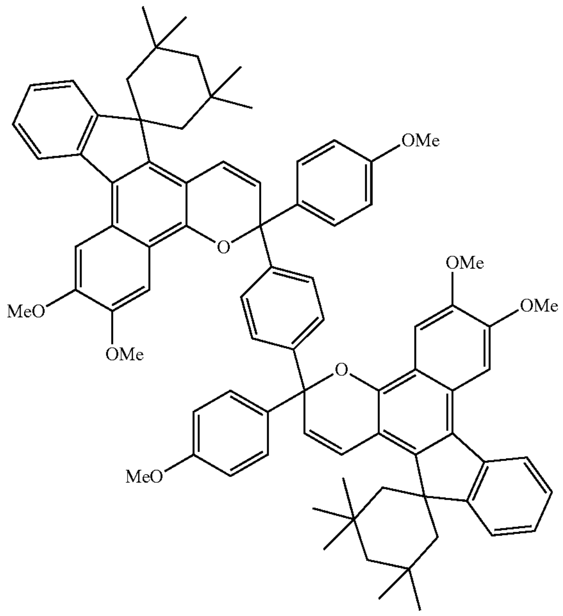

-continued
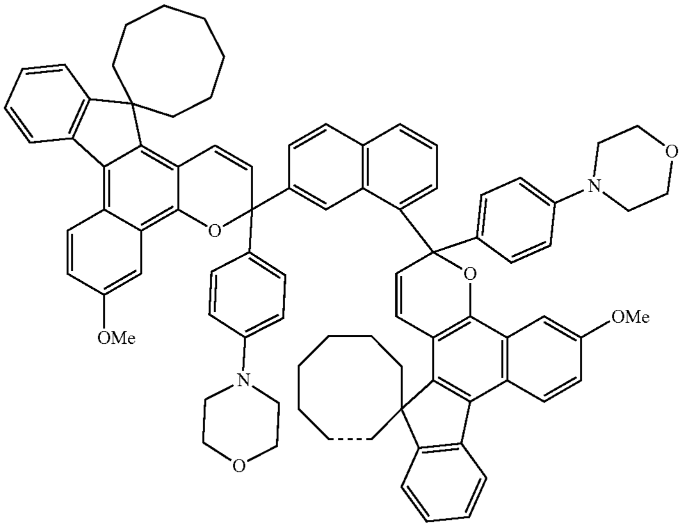
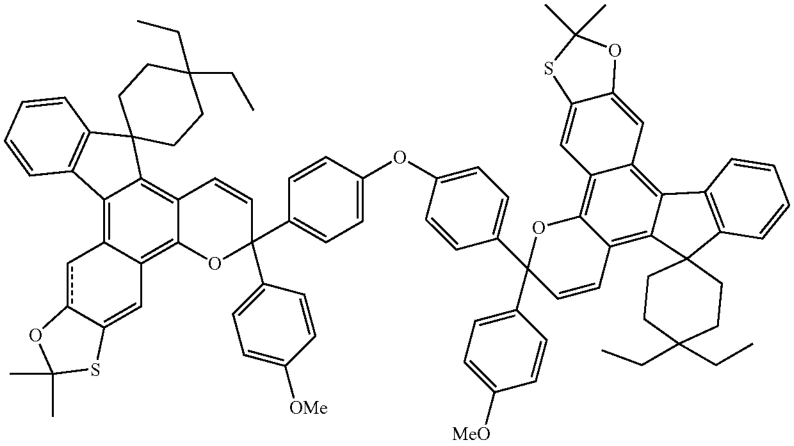
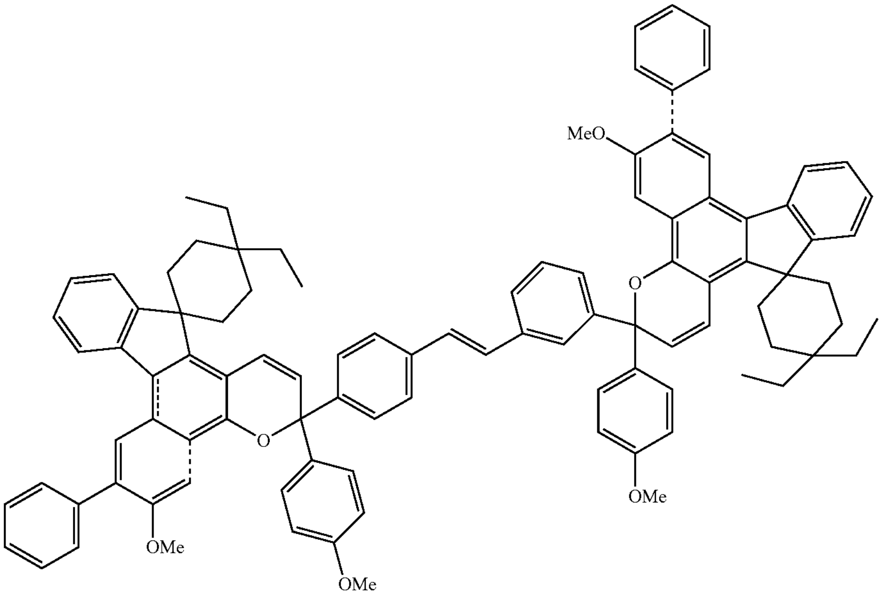

-continued
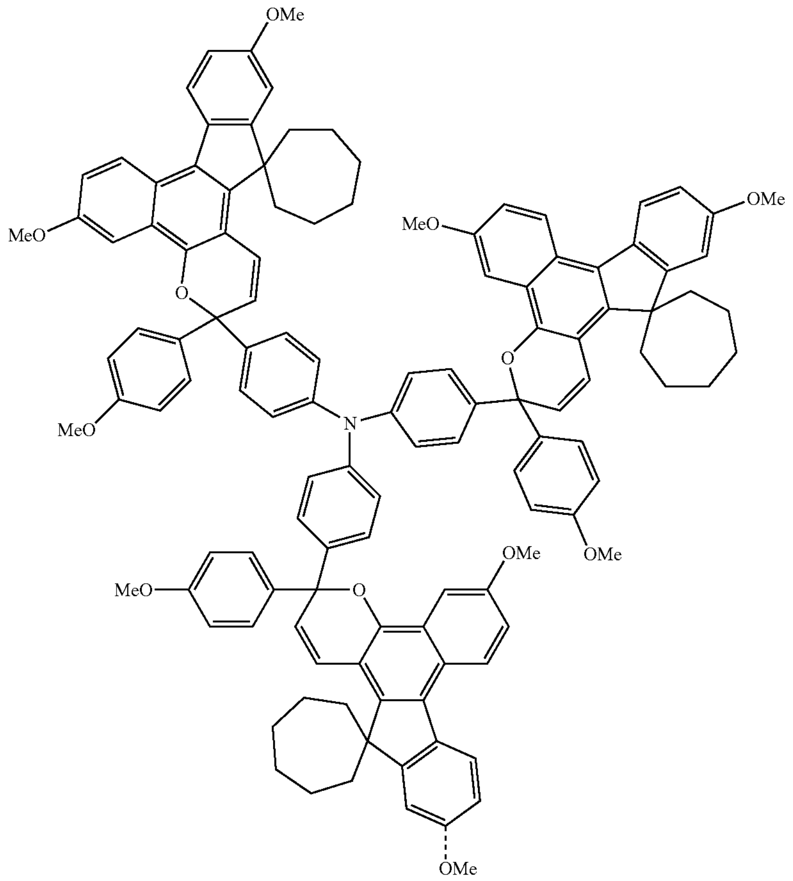
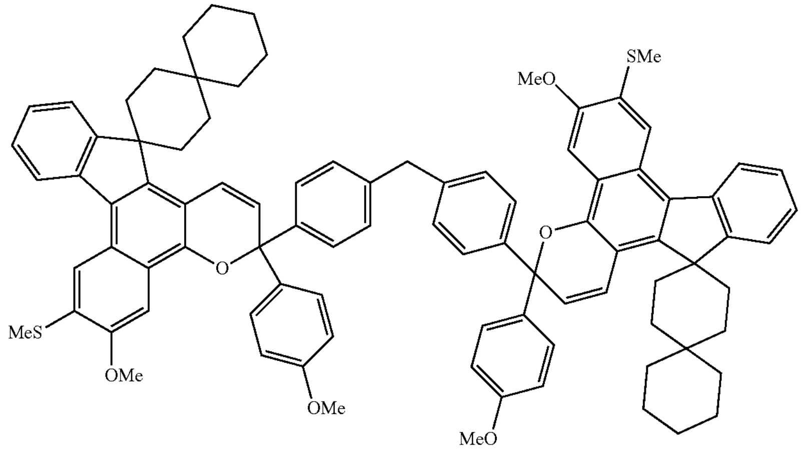
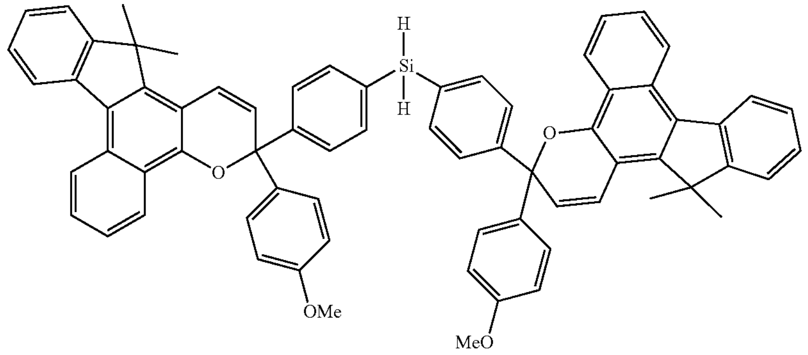

-continued

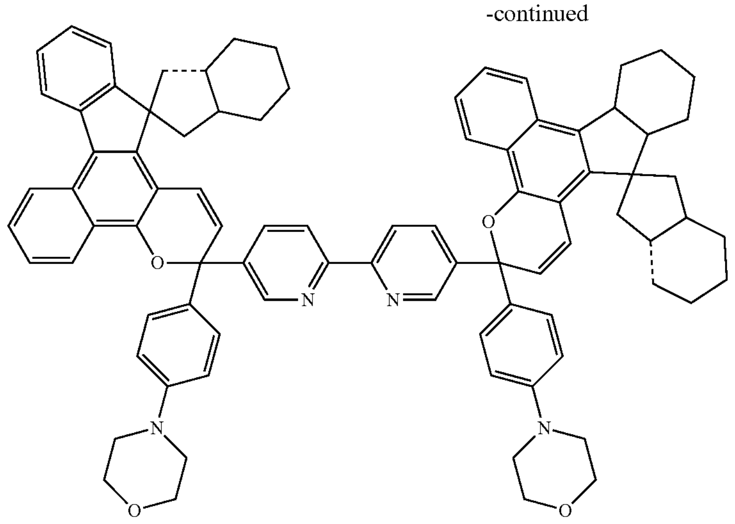

<Identification of Photochromic Compound>

The photochromic compound of the present invention, which is usually present as a solid at ordinary temperature and pressure, can be confirmed in the following manner: (a) to (c).

(a) The following peaks are measured in the proton nuclear magnetic resonance ($^1$H-NMR) spectrum:

δ: 5.0 to 9.0 ppm (a peak due to aromatic protons and alkene protons); and

δ: 1.0 to 4.0 ppm (a peak due to protons of alkyl groups and alkylene groups.)

The number of protons in the respective bonding groups can be determined by a relative comparison of the spectral intensities.

This allows for the identification of the bond.

(b) Elemental analysis allows for the determination of the composition of a corresponding product.

(c) The following peaks are measured in the $^{13}$C-nuclear magnetic resonance (13C-NMR) spectrum:

δ: 110 to 160 ppm (a peak due to carbons of aromatic hydrocarbon groups);

δ: 80 to 140 ppm (a peak due to carbons of alkenes and alkynes); and

δ: 20 to 80 ppm (a peak due to carbons of alkyl groups and alkylene groups.)

<Production of Photochromic Compound>

The photochromic compound of the present invention can be synthesized by using, for example, a cross-coupling reaction.

For example, a compound having a halogen atom, a triflate group or the like is prepared as a starting compound, which is subjected to a cross-coupling reaction with an organozinc compound, an organoboron compound, or an organotin compound in the presence of a transition metal catalyst such as palladium or nickel, thereby producing the photochromic compound.

Further, the indenonaphthopyran compound represented by Formula (2) can be suitably produced by the following method.

In the following description, references in each formula are the same as those in the above-described formulas unless otherwise specified.

A naphthol compound represented by Formula (3) below is reacted with a propargyl alcohol compound represented by Formula (4) below in the presence of an acid catalyst, thereby synthesizing the indenonaphthopyran compound represented by Formula (2).

(3)

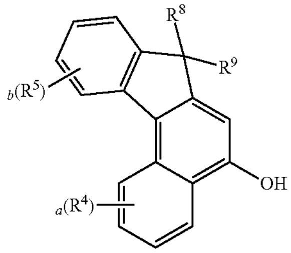

(4)

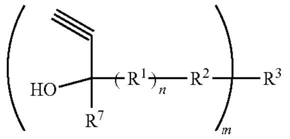

Examples of the acid catalyst used in the aforementioned reaction include sulfuric acid, benzenesulfonic acid, p-toluenesulfonic acid, and acidic alumina. The acid catalyst is preferably used in a range of 0.1 to 10 parts by mass per 100 parts by mass of the total amount of the naphthol compound and the propargyl alcohol compound.

The reaction temperature is preferably 0° C. to 200° C. The solvent is preferably an aprotic organic solvent such as N-methylpyrrolidone, dimethylformamide, tetrahydrofuran, benzene, toluene, methyl ethyl ketone, or methyl isobutyl ketone.

The product obtained by this reaction is purified by silica gel column chromatography, for example, followed further by purification by recrystallization.

The naphthol compound represented by Formula (3) preferably has a structure that allows the production of the suitable indenonaphthopyran (chromene) compound represented by Formula (2). Particularly preferred examples of the naphthol compound include those represented by the following formulas.

-continued

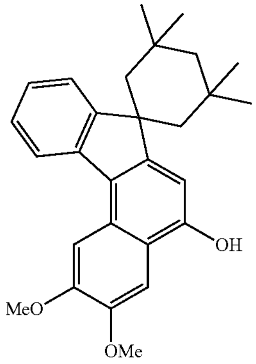

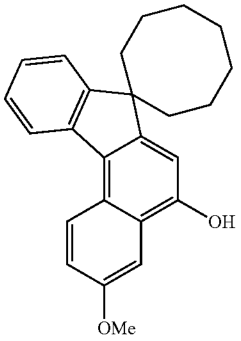

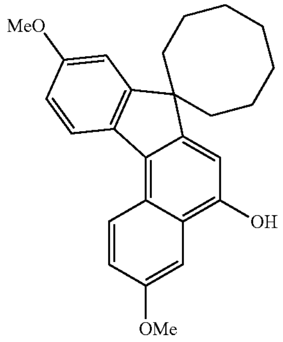

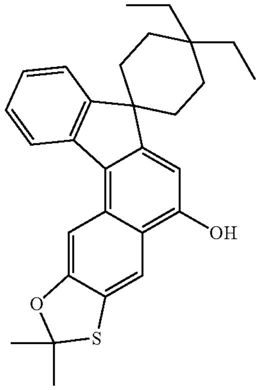

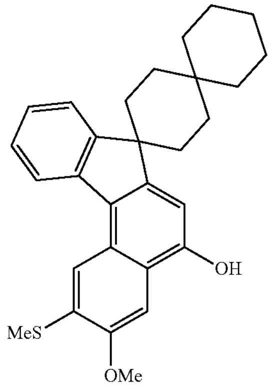

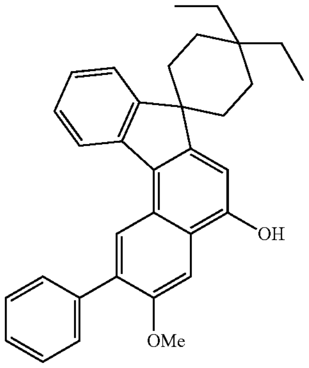

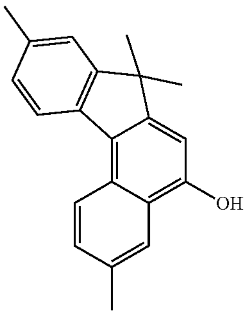

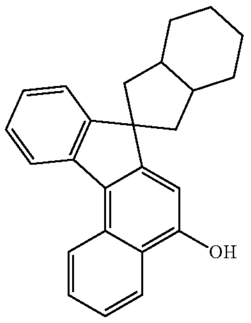

The naphthol compound represented by Formula (3) can be synthesized in the following manner, for example.

First, a benzophenone compound represented by Formula (5) below is prepared.

(5)

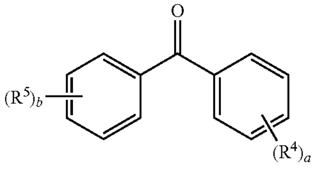

The benzophenone compound is subjected to the Stobbe reaction, a cyclization reaction, a hydrolysis reaction using an alkali or an acid, benzyl protection, debenzylation by the hydrolysis reaction using an alkali or an acid, and the like, thereby obtaining a benzyl protected carboxylic acid represented by Formula (6) below (where Bn is a benzyl group).

(6)

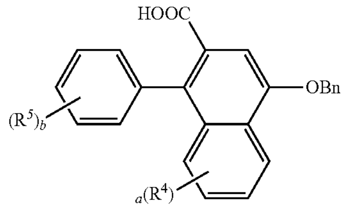

Then, the benzyl protected carboxylic acid above is converted into an amine by the Curtius rearrangement, the Hofmann rearrangement, the Lossen rearrangement or the like, from which a diazonium salt is prepared by a method known per se.

The diazonium salt is converted into a bromide by the Sandmeyer reaction or the like, and the thus-obtained bromide is reacted with magnesium, lithium or the like to prepare an organometallic compound. The organometallic compound is reacted with a ketone represented by Formula (7) below in an organic solvent at −80° C. to 70° C. for 10 minutes to four hours, thereby obtaining an alcohol compound.

(7)

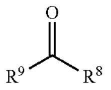

The thus-obtained alcohol compound is subjected to the Friedel-Crafts reaction. More specifically, the alcohol compound is reacted under neutral to acidic conditions at 10° C. to 120° C. for 10 minutes to two hours, so that the alcohol moiety is converted to a spiro moiety by a nucleophilic substitution reaction, thereby synthesizing the naphthol compound represented by Formula (3).

(3)

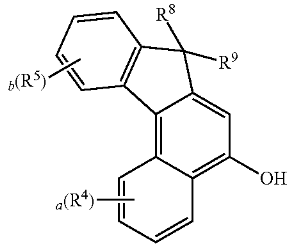

In this reaction, the reaction ratio of the organometallic compound to the ketone represented by Formula (7) is preferably selected from a range of 1:10 to 10:1 (molar ratio).

The reaction temperature is preferably −80° C. to 70° C.

The solvent is preferably an aprotic organic solvent such as diethyl ether, tetrahydrofuran, benzene, or toluene.

The Friedel-Crafts reaction is preferably performed using an acid catalyst such as acetic acid, hydrochloric acid, sulfuric acid, benzenesulfonic acid, p-toluenesulfonic acid, or acidic alumina. This reaction uses an aprotic organic solvent such as tetrahydrofuran, benzene, or toluene.

The propargyl alcohol compound represented by Formula (4) can be easily synthesized by reacting, for example, a ketone compound corresponding to Formula (4) with a metal acetylene compound such as lithium acetylide.

The photochromic (chromene) compound synthesized as described above is well soluble in a common organic solvent such as toluene, chloroform, or tetrahydrofuran. When the photochromic compound of the present invention is dissolved in such a solvent, the resultant solution, which is usually almost colorless and transparent, exhibits a good photochromic action such that it rapidly gets into a color developed state when irradiated with sunlight or ultraviolet rays, while it rapidly returns to its original colorless state reversibly when the light is blocked.

The photochromic compound of the present invention can be used in combination with another photochromic compound depending on the intended use. For example, for use for a photochromic lens which requires various color tones, another known photochromic compound such as fulgide, flugimide, spirooxazine, or chromene can be used in combination. Among them, a chromene compound is particularly preferably used in combination for the following reasons: Uniform color tones can be kept at the time of color development and fading; a deterioration in photochromic properties causes less color deviation at the time of color development; and initial coloration can be reduced. In this case where temperature dependence is to be reduced, it is preferable to use a plurality of kinds of the photochromic compounds of the present invention and adjust the color tone.

When the photochromic compound of the present invention is used in combination with another photochromic compound to form a photochromic composition, the blending ratio of each of the chromene compounds is appropriately determined depending on the desired color tone.

<Photochromic Curable Composition>

The photochromic compound of the present invention and the aforementioned photochromic composition are preferably combined with a polymerizable compound to be used as a photochromic curable composition.

The photochromic curable composition of the present invention preferably contains the photochromic compound of the present invention (or the photochromic composition) in an amount of 0.001 to 10 parts by mass per 100 parts by mass of a polymerizable compound, though the content cannot be determined definitely because it varies depending on the color development intensity of the photochromic compound, the selected lens material, and the thickness of the lens.

The optimum blending amount varies with the intended use. The following are an example of using the photochromic curable composition for a thin-film optical article and an example of using the photochromic curable composition for a thick-film optical article.

Use for Thin-Film Optical Article:

For example, when the photochromic curable composition is formed into a thin film (a polymer film formed by polymerization of the photochromic curable composition) of approximately 100 μm, it is preferable to adjust the color tone by using the photochromic compound of the present invention (or the photochromic composition) in an amount of 0.001 to 10 parts by mass per 100 parts by mass of another polymerizable monomer.

Use for Thick-Film Optical Article:

When the photochromic curable composition is formed into a thick cured body (a polymer molded body formed by polymerization of the photochromic curable composition) with a thickness of not less than 1 millimeter, for example, it is preferable to adjust the color tone by using the photochromic compound of the present invention (or the photochromic composition) in an amount of 0.001 to 1 parts by mass per 100 parts by mass of the thick cured body or another polymerizable monomer giving the thick cured body.

<Polymerizable Compound>

As described above, the photochromic compound of the present invention is preferably combined with a polymerizable compound to be used as a photochromic curable composition. Examples of the polymerizable compound include a urethane- or urea-based polymerizable compound capable of forming a urethane bond, a urea bond, and the like, a radically polymerizable compound, and an epoxy-based polymerizable compound. Although these polymerizable compounds are not particularly limited, the polymerizable compound described in WO 2018/235771 can be suitably used, for instance.

Among them, polymerizable compounds described below are used particularly suitably.

Iso(Thio)Cyanate Compound:

An iso(thio)cyanate compound is a compound having an isocyanate group or an isothiocyanate group, and it may contain both an isocyanate group and an isothiocyanate group. This compound is suitably used in combination with any of the following compounds containing active hydrogen.

Examples of the iso (thio) cyanate compounds are as follows, though the compounds are not limited to these examples:

Polyiso(thio)cyanate having at least two iso(thio)cyanate groups in one molecule;

Aromatic polyiso(thio)cyanate having an aromatic ring such as m-xylene diisocyanate or 4,4'-diphenylmethane diisocyanate; and Aliphatic polyiso(thio)cyanate such as norbornane diisocyanate or dicyclohexylmethane-4,4'-diisocyanate.

Compound Having Active Hydrogen:

The compound having active hydrogen is preferably a compound having a hydroxyl group and/or a thiol group, and particularly preferably, a polyfunctional compound having two or more active hydrogens in one molecule, though the present invention is not limited thereto. Specific examples of the compound having active hydrogen include polyfunctional thiol compounds such as pentaerythritoltetrakis(3-mercaptopropionate) and 4-mercaptomethyl-3,6-dithia-octanedithiol, and polyfunctional alcohols such as trimethylolpropane and pentaerythritol.

Radically Polymerizable Compound:

The radically polymerizable compound can be classified into a polyfunctional radically polymerizable compound and a monofunctional radically polymerizable compound, each of which can be used alone, or a plurality of the compounds can be used in combination. Examples of the radically polymerizable substituent include a group having an unsaturated double bond, that is, a vinyl group (including a styryl group, a (meth)acrylic group, an allyl group, and the like).

The polyfunctional radically polymerizable compound is a compound having two or more radically polymerizable substituents in a molecule. This polyfunctional radically polymerizable compound can be classified into a first polyfunctional radically polymerizable compound having 2 to 10 radically polymerizable substituents and a second polyfunctional radically polymerizable compound having more than 10 radically polymerizable substituents.

The first radically polymerizable compound is not particularly limited, but preferably it has 2 to 6 radically polymerizable substituents. Specific examples thereof are as follows.

Polyfunctional (Meth)Acrylic Ester Compounds:

Ethylene glycol di(meth)acrylate,

Diethylene glycol di(meth)acrylate,

Triethylene glycol di(meth)acrylate,

Tetraethylene glycol di(meth)acrylate,

Ethylene glycol bisglycidyl(meth)acrylate,

Bisphenol A di(meth)acrylate, 2,2-Bis(4-(metha)acryloyloxyethoxyphenyl)propane, and 2,2-Bis(3,5-dibromo-4-(meth)acryloyloxyethoxyphenyl) propane.

Polyfunctional Allylic Compounds:

Diallyl phthalate,

Diallyl terephthalate,

Diallyl isophthalate,

Diallyl tartrate,

Diallyl epoxy succinate,

Diallyl fumarate,

Diallyl chlorendate,

Diallyl hexaphthalate,

Diallyl carbonate,

Allyl diglycol carbonate, and

Trimethylolpropane triallyl carbonate.

Polyfunctional Thio(Meth)Acrylic Ester Compounds:

1,2-Bis(methacryloylthio)ethane,

Bis(2-acryloylthioethyl)ether, and 1,4-Bis(methacryloylthiomethyl)benzene.

Vinyl Compounds:

Divinylbenzene.

Examples of the second polyfunctional radically polymerizable compound having more than 10 radically polymerizable substituents include compounds having a relatively large molecular weight, such as a silsesquioxane compound having radically polymerizable substituents and a polyrotaxane compound having radically polymerizable substituents.

The monofunctional radically polymerizable compound is a compound having one radically polymerizable substituent in a molecule, and specific examples thereof include the following compounds, though the present invention is not limited thereto.

Unsaturated Carboxylic Acids:

Acrylic acid,

Methacrylic acid, and

Maleic anhydride.

(Meth)Acrylic Acid Esters:

Methyl(meth)acrylate,

Benzyl methacrylate,

Phenyl methacrylate,

2-Hydroxyethyl methacrylate,

Glycidyl (meth)acrylate,

β-Methylglycidyl (meth)acrylate,

Bisphenol A-monoglycidyl ether-methacrylate,

4-Glycidyloxymethacrylate, 3-(Glycidyl-2-oxyethoxy)-2-hydroxypropyl methacrylate, 3-(Glycidyloxy-1-isopropyloxy)-2-hydroxypropylacrylate, and 3-(Glycidyloxy-2-hydroxypropyloxy)-2-hydroxypropylacrylate.

Fumaric Acid Esters:

Diethyl fumarate, and

Diphenyl fumarate.

Thio(Meth)Acrylic Acids:
- Methylthioacrylate,
- Benzylthioacrylate, and
- Benzylthiomethacrylate.

Vinyl Compounds:
- Styrene,
- Chlorostyrene,
- Methylstyrene,
- Vinylnaphthalene,
- α-Methylstyrene dimer, and
- Bromostyrene.

The radically polymerizable compound may be used alone, or a mixture of a plurality thereof may be used. In this case, the amount of the polyfunctional radically polymerizable compound is preferably set to 80 to 100 parts by mass, and the amount of the monofunctional radically polymerizable compound is preferably set to 0 to 20 parts by mass, relative to 100 parts by mass of the total of the radically polymerizable compounds. More preferably, the polyfunctional radically polymerizable compound is set to 90 to 100 parts by mass, and the monofunctional radically polymerizable compound is set to 0 to 10 parts by mass. Further, it is preferable to set the first polyfunctional radically polymerizable compound to 80 to 100 parts by mass, the second radically polymerizable compound to 0 to 20 parts by mass, and the monofunctional radically polymerizable compound to 0 to 20 parts by mass, relative to 100 parts by mass of the total of the radically polymerizable compounds. And it is further preferable to set the first polyfunctional radically polymerizable compound to 85 to 100 parts by mass, the second polyfunctional radically polymerizable compound to 0 to 15 parts by mass, and the monofunctional radically polymerizable compound to 0 to 15 parts by mass.

Compounding Agent:

Various compounding agents known per se exemplified by stabilizers may be blended in the curable composition of the present invention, within a range not impairing the effect of the present invention, and the examples include a mold release agent, an ultraviolet absorber, an infrared absorber, an ultraviolet stabilizer, an antioxidant, a coloring inhibitor, an antistatic agent, a fluorescent dye, a dye, a pigment, and a perfume. A solvent or a leveling agent also may be blended. Furthermore, thiols such as t-dodecylmercaptan may be blended as a polymerization modifier, if necessary.

Among these agents, the ultraviolet stabilizer is suitable from the viewpoint that the durability of the photochromic moiety can be improved. As the ultraviolet stabilizer, a hindered amine light stabilizer, a hindered phenol antioxidant, a sulfur-based antioxidant and the like are known. Particularly suitable ultraviolet stabilizers are as follows:

- Bis(1,2,2,6,6-pentamethyl-4-piperidyl) sebacate;
- ADKSTAB® LA-52, LA-57, LA-62, LA-63, LA-67, LA-77, LA-82, and LA-87 manufactured by ADEKA CORPORATION;
- 2,6-Di-tert-butyl-4-methyl-phenol;
- Ethylenebis(oxyethylene)bis[3-(5-tert-butyl-4-hydroxy-m-tolyl)propionate]; and
- IRGANOX® 1010, 1035, 1075, 1098, 1135, 1141, 1222, 1330, 1425, 1520, 259, 3114, 3790, 5057, and 565 manufactured by Ciba Specialty Chemicals.

Though the use amount of the ultraviolet stabilizer is not particularly limited as long as the effect of the present invention is not impaired, usually it is in the range of 0.001 to 10 parts by mass, particularly 0.01 to 1 parts by mass, relative to 100 parts by mass of the photochromic hydroxyurethane compound of the present invention. In particular, in a case of using a hindered amine light stabilizer, the effect of improving durability may vary depending on the type of photochromic moiety, and as a result, a color deviation may occur in the adjusted color tone at the time of color development. In order to prevent or reduce the color deviation, the blending amount is preferably 0.5 to 30 mol, more preferably 1 to 20 mol, and still more preferably 2 to 15 mol, per mol of the photochromic moiety.

Besides the ultraviolet stabilizer, the ultraviolet absorber can also be used. Known ultraviolet absorbers are available, such as a benzophenone compound, a benzotriazole compound, a cyanoacrylate compound, a triazine compound, and a benzoate compound. In particular, a cyanoacrylate compound and a benzophenone compound are preferred. The ultraviolet stabilizer is preferably used in an amount in a range of 0.001 to 5 parts by mass per 100 parts by mass of the photochromic curable composition containing the photochromic compound and the polymerizable compound.

<Use of Photochromic Curable Composition: Optical Article>

The polymerizable compound for use in the photochromic curable composition of the present invention is as exemplified above. The blending proportion of the polymerizable compound may be determined appropriately depending on the intended use. However, the blending amount of the chromene compound or the photochromic composition is preferably as described above.

The photochromic curable composition of the present invention can be prepared by mixing the photochromic compound (photochromic composition) for use, the polymerizable compound, and the additive, etc. to be blended as needed.

Polymerization curing for producing a photochromic cured body is performed by radical polymerization, ring-opening polymerization, anionic polymerization or condensation polymerization by irradiation with active energy rays such as ultraviolet rays, α rays, β rays or γ rays, by heating or a combination thereof, for instance. In other words, an appropriate polymerization means may be employed in accordance with the type of the polymerizable compound and the polymerization curing accelerator and the form of the photochromic cured body to be formed.

At the time of thermally polymerizing the curable composition of the present invention in which the polymerizable compound is blended, the temperature affects the properties of the photochromic cured body to be obtained.

The temperature condition cannot be definitely limited as it is under the influence of the type and amount of the thermal polymerization initiator and the type of the polymerizable compound. Usually, however, a method in which polymerization is started at a relatively low temperature, which is then slowly raised is suitable. As for the polymerization time, which also varies with various factors just like the temperature, it is suitable to determine in advance the optimal time depending on the conditions. It is usually preferable to select the condition so that polymerization is completed in 2 to 48 hours. In a case of obtaining a photochromic laminated sheet, it is preferable to determine the optimal temperature and time so that polymerization is performed at a temperature at which the reaction of the polymerizable functional groups proceeds and a target molecular weight is obtained by the polymerization.

In the photopolymerization of the curable composition of the present invention, the UV intensity as one of the polymerization conditions particularly affects the properties of the photochromic cured body to be obtained. The illumination condition cannot be definitely limited because it is under the influence of the type and amount of the photopolymerization initiator and the type of the polymerizable monomer. However, it is usually preferable to select the condition so that UV light of 50 to 500 $mW/cm^2$ is irradiated at a wavelength of 365 nm for 0.5 to 5 minutes.

The photochromic compound of the present invention can be widely used as a photochromic material. Examples include various memory materials as a replacement for a silver halide photosensitive material, such as a copying material, a printing photoreceptor, a memory material for cathode-ray tubes, a photosensitive material for lasers, and a photosensitive material for holography. In addition, a photochromic material using the chromene compound of the present invention can also be used as a photochromic lens material, an optical filter material, a display material, an actinometer material, a decoration material and the like.

For example, a photochromic lens using the photochromic compound of the present invention can be produced by polymerization curing as described above in any known manner as long as uniform dimming performance is achieved.

In a case of exhibiting photochromic properties by a kneading method, the aforementioned curable composition is injected between glass molds held by an elastomer gasket or a spacer, followed by cast polymerization with heat in an air furnace or by irradiation with active energy rays such as ultraviolet rays depending on the type of the polymerizable compound and the polymerization curing accelerator, thereby obtaining a photochromic cured body molded into a form of an optical material such as a lens.

In a case of exhibiting photochromic properties by a lamination method, the curable composition is appropriately dissolved in an organic solvent to prepare a coating liquid, and the coating liquid is applied to a surface of an optical base material such as a lens base material by spin coating, dipping, or the like, dried to remove the organic solvent, and then, UV-irradiated or heated in an inert gas such as nitrogen or the like to perform polymerization curing. In this manner, a photochromic layer made of a photochromic cured body is formed on the surface of the optical base material (coating method).

It is also possible to form the photochromic layer of a photochromic cured body on the surface of the optical base material by cast polymerization using an inner mold. In the formation, an optical base material like a lens base material is disposed facing the glass mold so as to form a predetermined void, into which the curable composition is injected, and polymerization curing is performed by UV irradiation, heating or the like (cast polymerization method).

In a case of forming a photochromic layer on the surface of the optical base material by the lamination method (coating method and cast polymerization method) as described above, it is also possible to subject in advance the surface of the optical base material to a chemical treatment with an alkaline solution, an acid solution or the like, or a physical treatment by corona discharge, plasma discharge, polishing or the like so as to enhance the adhesion between the photochromic layer and the optical base material. Needless to note, it is also possible to provide a transparent adhesive resin layer on the surface of the optical base material.

In a case of exhibiting photochromic properties by a binder method, a photochromic sheet is prepared by sheet formation using the curable composition. This sheet is sandwiched between two transparent sheets (optical sheets) and subjected to the polymerization curing as described above, whereby a photochromic laminate having a photochromic layer as an adhesive layer is obtained.

In this case, the photochromic sheet can also be prepared by applying a coating liquid containing the curable composition dissolved in an organic solvent.

The thus produced photochromic laminate is mounted in a mold, for instance, and thereafter, a thermoplastic resin (e.g., polycarbonate) for an optical base material like a lens is injection molded, whereby an optical base material like a lens having a predetermined shape imparted with photochromic properties is obtained.

This photochromic laminate can also be made to adhere to the surface of the optical base material by an adhesive or the like to obtain a photochromic lens.

In a case of producing a photochromic laminate in the aforementioned manner, it is preferable that a urethane- or urea-based polymerizable compound is used as the polymerizable compound, since it has particularly high adhesion to the optical base material. Particularly preferably, a urethane-based polymerizable compound is used, which is adjusted to form polyurethane.

The aforementioned curable composition of the present invention exhibits photochromic properties excellent in color optical density at high temperature.

The photochromic layer or the photochromic cured body formed of the curable composition of the present invention may be subjected to any post-treatment, depending on its application. Examples of the post-treatment include: dyeing with a dyestuff such as a dispersive dye; formation of a hard coat film by use of a silane coupling agent or a hard coat agent based on a sol of silicon, zirconium, antimony, aluminum, tin, or tungsten as a main component; formation of a thin film by vapor deposition of a metal oxide such as $SiO_2$, $TiO_2$, or ZrO2; an antireflection treatment by use of a thin film coating of an organic polymer; and an antistatic treatment.

EXAMPLES

Example 1

First Step:

| | |
|---|---|
| 4,4'-stilbenedicarboxylic acid | 2.68 g (10.0 mmol), |
| thionyl chloride | 50 mL, and |
| DMF | 3 drops |

were refluxed under nitrogen for two hours. After confirmation that the raw materials had been consumed, vacuum concentration was performed to dryness. Thus, 4,4'-stilbenedicarbonyl chloride as a yellow solid was obtained in a yield of 100%.

Second Step:

Aluminum chloride 2.93 g (22.0 mmol), and
dichloromethane 30 mL
were added to the 4,4'-stilbenedicarbonyl chloride obtained in the first step, followed by stirring under nitrogen for one hour.

Anisole 2.70 g (25.0 mmol), and
dichloromethane 50 mL
were stirred at ice temperature, to which the dichloromethane solution of the 4,4'-stilbenedicarbonyl chloride and the aluminum chloride obtained above was added, followed by stirring for 12 hours while raising the temperature to room temperature.

500 mL of methanol at ice temperature was added, and a precipitated solid was filtered and washed with methanol. 100 mL of chloroform was added to the thus-obtained solid, followed by refluxing for one hour. The resultant solid was cooled to room temperature and filtered to obtain bisbenzophenone represented by Formula (8) below in a yield of 75%.

(8)

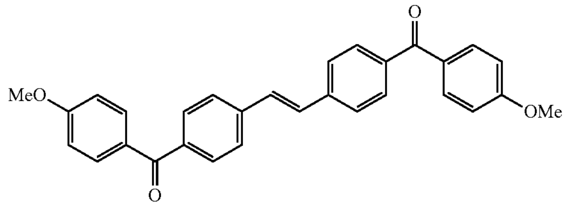

Third Step:

Trimethylsilylacetylene 2.95 g (30.0 mmol), and
THF 30 mL
were stirred and cooled to −20° C., to which 18.8 mL of n-BuLi (a 1.6 mM hexane solution) was slowly added, followed by stirring for one hour.

2.24 g (5.0 mmol) of the bisbenzophenone obtained in the second step was added thereto, followed by stirring for 12 hours while raising the temperature to room temperature.

After confirmation that the raw materials had been consumed, the resultant mixture was ice cooled, to which a 20 mL methanol solution of 1.74 g (31.0 mmol) of potassium hydroxide was added, followed by stirring for another three hours. A 10% aqueous ammonium chloride solution was used to perform separation, thereby obtaining bispropargyl alcohol represented by Formula (9) below in a yield of 90%.

(9)

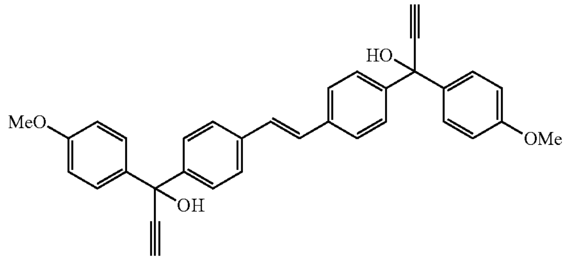

Fourth Step:

Anaphthol compound represented by Formula (10) below was prepared.

(10)

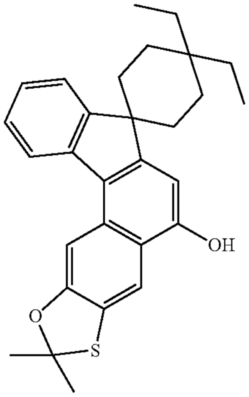

The naphthol compound above 1.33 g (3.0 mmol), and
the bispropargyl alcohol compound obtained in the third step
2.00 g (4.0 mmol) were dissolved in 50 ml of toluene, to which
pyridinium p-toluenesulfonate 0.75 g (0.3 mmol) was added, followed by stirring at 85° C. for one hour. After the reaction, the solvent was removed, followed by purification by chromatography on silica gel, thereby obtaining a compound represented by Formula (11) below in a yield of 70%.

(11)

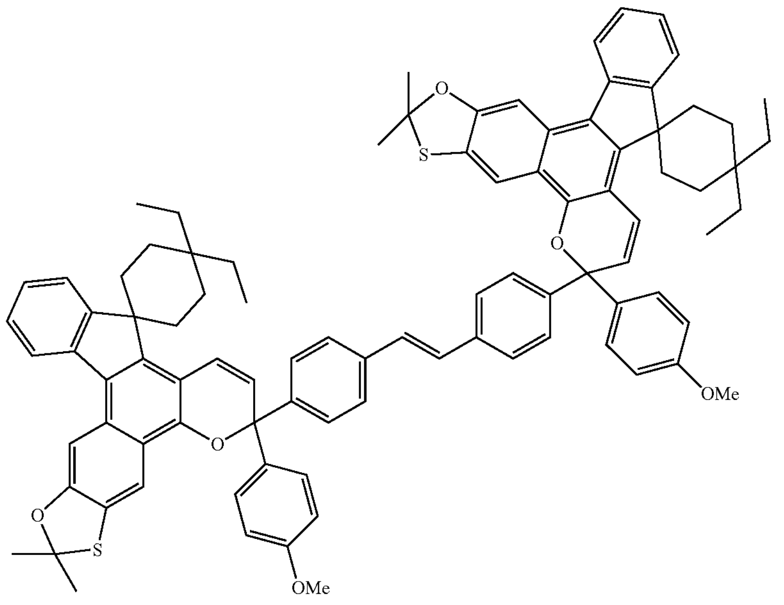

The elemental analysis values of this product were as follows:

C: 81.5%, H: 6.7%, and S: 4.7%.

These analysis values were in great identified with the calculated values, C: 81.6%, H: 6.6%, and S: 4.7%, of $C_{92}H_{88}O_6S_2$.

Further, the proton nuclear magnetic resonance spectrum was measured. The following peaks were observed:

a peak of 48 H due to cyclohexane rings, ethyl groups, and methyl groups at around 1.0 to 3.0 ppm;

a peak of 6 H due to methoxy groups at around δ 2.3 to 4.0 ppm; and a peak of 34 H due to aromatic protons and alkene protons at around δ 5.0 to 9.0 ppm.

Furthermore, the $^{13}C$-nuclear magnetic resonance spectrum was measured. The following peaks were observed:

a peak due to aromatic ring carbons at around δ 110 to 160 ppm;

a peak due to alkene carbons at around δ 80 to 140 ppm; and a peak due to alkyl carbons at δ 20 to 60 ppm.

Examples 2 to 4

Each of propargyl alcohol compounds shown in Table 1 (Examples 2 to 4) was prepared in the same manner as in Example 1, and reacted with the naphthol compound of Example 1, thereby synthesizing a chromene compound (photochromic compound).

TABLE 1

| Example | Propargyl alcohol compound | Photochromic compound |
|---|---|---|
| 2 | 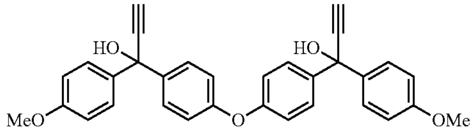 [SMILES: C#CC(O)(c1ccc(OC)cc1)c1ccc(Oc2ccc(C(O)(C#C)c3ccc(OC)cc3)cc2)cc1] | 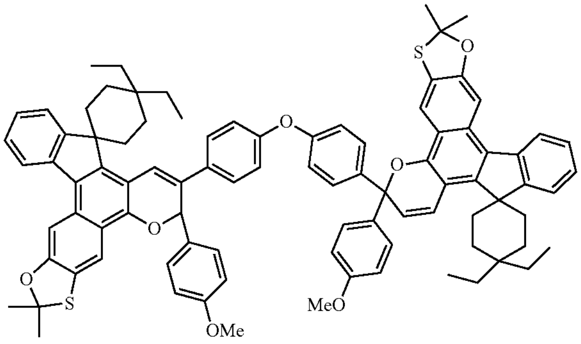 [SMILES: CCC1(CC)CCC2(CC1)c1ccccc1-c1c2c2c(c3cc4c(cc13)OC(C)(C)S4)OC(c1ccc(OC)cc1)C(c1ccc(Oc3ccc(C4(c5ccc(OC)cc5)C=Cc5c6c(c7cc8c(cc7c5O4)SC(C)(C)O8)-c4ccccc4C64CCC(CC)(CC)CC4)cc3)cc1)=C2] |
| 3 | 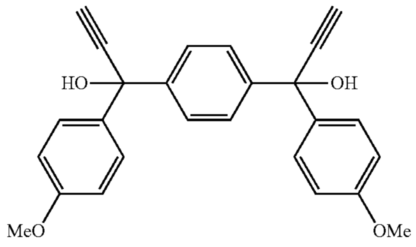 [SMILES: C#CC(O)(c1ccc(OC)cc1)c1ccc(C(O)(C#C)c2ccc(OC)cc2)cc1] | 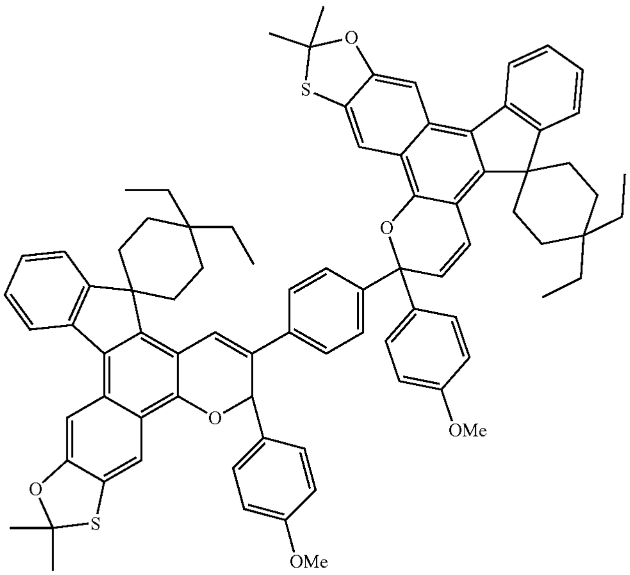 [SMILES: CCC1(CC)CCC2(CC1)c1ccccc1-c1c2c2c(c3cc4c(cc13)OC(C)(C)S4)OC(c1ccc(OC)cc1)C(c1ccc(C3(c4ccc(OC)cc4)C=Cc4c5c(c6cc7c(cc6c4O3)SC(C)(C)O7)-c3ccccc3C53CCC(CC)(CC)CC3)cc1)=C2] |

TABLE 1-continued

| Example | Propargyl alcohol compound | Photochromic compound |
|---|---|---|
| 4 | 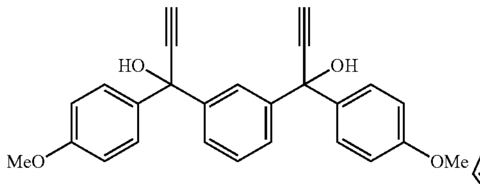 | 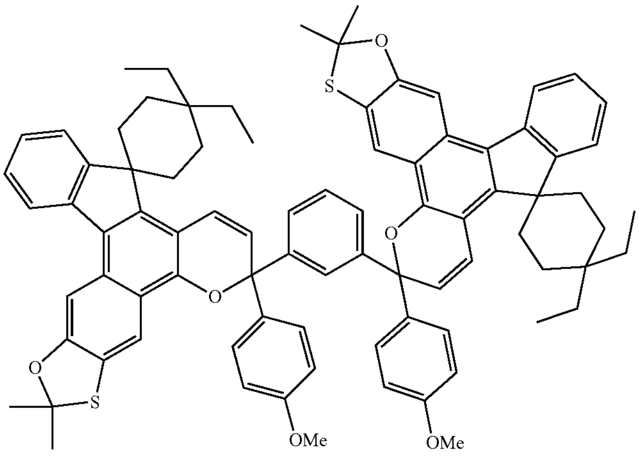 [SMILES: CCC1(CC)CCC2(CC1)c1ccccc1-c1c2c2c(c3cc4c(cc13)OC(C)(C)S4)OC(c1ccc(OC)cc1)(c1cccc(C3(c4ccc(OC)cc4)C=Cc4c5c(c6cc7c(cc6c4O3)SC(C)(C)O7)-c3ccccc3C53CCC(CC)(CC)CC3)c1)C=C2] |

Each of the obtained chromene compounds was subjected to a structural analysis by using the same structure confirmation means as in Example 1. As a result, the chromene compound was identified as a compound represented by each of the structural formulas shown in Table 1.

Further, Table 2 shows the elemental analysis values of each of the compounds, the calculated values obtained from the structural formula of each of the compounds, and the characteristic 1H-NMR spectrum.

TABLE 2

| Example | Compound No. | Calculated value C | Calculated value H | Calculated value S | Measured value C | Measured value H | Measured value S | $^1$H-NMR |
|---|---|---|---|---|---|---|---|---|
| 2 | 2 | 80.44 | 6.45 | 4.77 | 80.43 | 6.43 | 4.8 | δ 0-5.0 ppm, 54 H<br>δ 5.0-9.0 ppm, 32 H |
| 3 | 3 | 80.60 | 6.60 | 5.12 | 80.58 | 6.61 | 5.11 | δ 0-5.0 ppm, 28 H<br>δ 5.0-9.0 ppm, 54 H |
| 4 | 4 | 80.60 | 6.60 | 5.12 | 80.61 | 6.62 | 5.09 | δ 0-5.0 ppm, 28 H<br>δ 5.0-9.0 ppm, 54 H |

Examples 5 to 8

(Evaluation in Toluene Solution)

A toluene solution of 0.05 mmol/L (0.1 mmol/L in terms of the photochromic moiety) of each of the photochromic compounds of Examples 1 to 4 was prepared and subjected to the following evaluation using a quartz cell with an optical path length of 1 cm. The results are shown in Table 3.

(1) Photochromic Properties

[1] Maximum Absorption Wavelength (λmax):

The maximum absorption wavelength was obtained after color development by a spectrophotometer (instantaneous multichannel photodetector, MCPD3000) manufactured by Otsuka Electronics Co., Ltd. for use as an indicator of the color tone at the time of color development.

[2] Color Optical Density ($A_{23}$) at 23° C.:

A difference between the absorbance {s (180)} after light irradiation at 23° C. for 180 seconds and the absorbance s (O) before light irradiation, at the aforementioned maximum absorption wavelength was defined as an indicator of the color optical density. The higher this value, the better the photochromic properties.

[3] Color Optical Density ($A_{36}$) at 36° C.:

A difference between the absorbance {s (180)} after light irradiation at 36° C. for 180 seconds and the absorbance s (O) before light irradiation, at the aforementioned maximum absorption wavelength was defined as an indicator of the color optical density. The higher this value, the better the photochromic properties.

[4] Temperature Dependence ($A_{36}/A_{23}\times100$)

A ratio of the color optical density ($A_{36}$) at 36° C. to the color optical density ($A_{23}$) at 23° C. was defined as temperature dependence. The higher this value, the smaller and better the temperature dependence.

[5] Fading Half-Life at 23° C. [τ½ (Sec.)]:

A time required for the absorbance of the sample at the aforementionedmaximum absorption wavelength to decrease to ½ of {ε(180)−ε(0)} when light irradiation at 23° C. for 180 seconds was stopped was defined as an indicator of the fading rate. The shorter this time, the higher the fading rate.

TABLE 3

| Example | Compound No. | L-R$^3$ molecular weight | λ max (nm) | $A_{23}$ (−) | $A_{36}$ (−) | $A_{36}/A_{23}\times100$ (%) | τ 1/2 (sec) |
|---|---|---|---|---|---|---|---|
| 5 | 1 | 178 | 461 | 0.83 | 0.48 | 58% | 60 |
| | | | 562 | 0.59 | 0.34 | 58% | 59 |
| 6 | 2 | 168 | 448 | 0.83 | 0.44 | 53% | 41 |
| | | | 554 | 0.55 | 0.30 | 53% | 41 |
| 7 | 3 | 76 | 444 | 0.78 | 0.44 | 57% | 58 |
| | | | 556 | 0.53 | 0.29 | 57% | 57 |
| 8 | 4 | 76 | 443 | 0.69 | 0.38 | 55% | 50 |
| | | | 551 | 0.45 | 0.25 | 56% | 49 |

In Table 3, the compound synthesized in Example 1 is referred to as Compound 1, and the compounds synthesized in Examples 2 to 4 are similarly referred to as Compounds 2 to 4, respectively.

Comparative Examples 1 to 3

For comparison, a toluene solution of 0.1 mmol/L of a compound represented by each of Formulas (A) to (C) below was obtained and subjected to the property evaluation in the same manner as in Examples. The results are shown in Table 4.

(A)

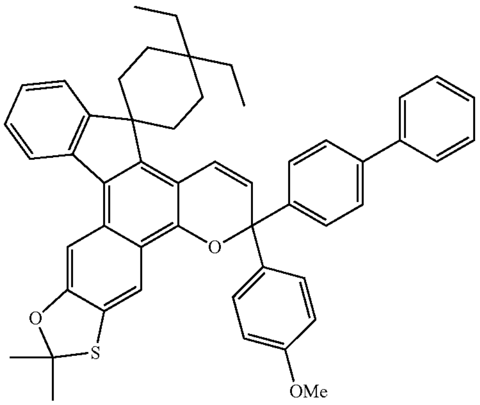

(B)

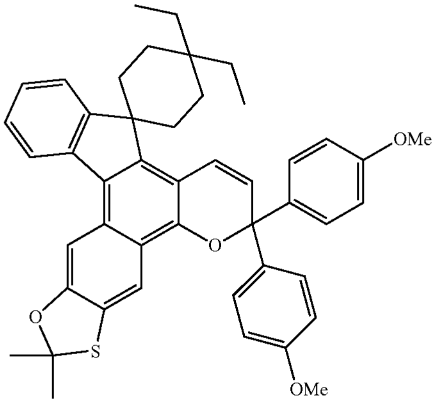

(C)

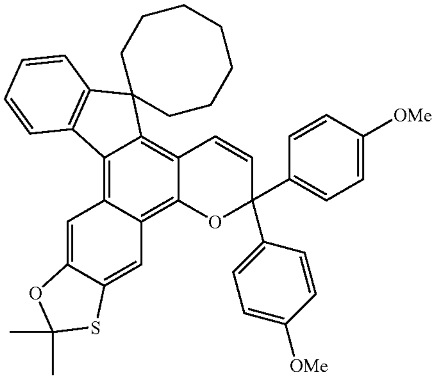

TABLE 4

| Comparative Example | Compound No. | λ max (nm) | $A_{23}$ (−) | $A_{36}$ (−) | $A_{36}/A_{23}$ × 100 (%) | τ 1/2 (sec) |
|---|---|---|---|---|---|---|
| 1 | A | 450 | 1.14 | 0.59 | 52% | 69 |
| | | 558 | 0.74 | 0.38 | 52% | 69 |
| 2 | B | 455 | 0.82 | 0.36 | 44% | 31 |
| | | 557 | 0.59 | 0.26 | 44% | 31 |

TABLE 4-continued

| Comparative Example | Compound No. | λ max (nm) | $A_{23}$ (−) | $A_{36}$ (−) | $A_{36}/A_{23}$ × 100 (%) | τ 1/2 (sec) |
|---|---|---|---|---|---|---|
| 3 | C | 452 | 1.16 | 0.58 | 50% | 60 |
| | | 558 | 0.77 | 0.38 | 50% | 60 |

FIG. 1 shows a plot of the results of the temperature dependence ($A_{36}/A_{23}$×100(%) in Tables 3 and 4) and the fading half-life at 23° C. in Examples 5 to 8 and Comparative Examples 1 to 3.

As can be seen from FIG. 1, the compounds of Comparative Examples exhibit a linear relationship between the temperature dependence and the fading half-life at 23° C. This means that a compound with a higher fading rate has smaller temperature dependence. Since the compounds of Examples and the compounds of Comparative Examples have the same structure except for the presence or absence of a bond, the compounds of Examples 5 to 8 and the compounds of Comparative Examples 1 to 3, which are contained at the same concentration in terms of the photochromic moiety, can be compared as they are.

As is evident from FIG. 1, the relationship of Examples 5 to 8 (Compounds No. 1 to 4) using the photochromic compound of the present invention is observed above the linear relationship of Comparative Examples. This means that the photochromic compound of the present invention is more excellent (smaller) in temperature dependence when compared at the same fading rate.

Example 9

(Physical Property Evaluation of Photochromic Plastic Lens Produced by Coating Method)

The chromene compound No. 1 obtained in Example 1 was mixed with a photopolymerization initiator and a polymerizable monomer. Then, the mixture was coated on the surface of a lens base material, and further irradiated with ultraviolet rays to polymerize a coating film on the surface of the lens base material.

A combination of the following radically polymerizable monomers was used for a photochromic curable composition.

Polyethylene glycol dimethacrylate (average molecular weight: 736)
45 parts by mass,
Polyethylene glycol dimethacrylate (average molecular weight: 536)
7 parts by mass,
Trimethylolpropane trimethacrylate 40 parts by mass,
γ-methacryloyloxypropyltrimethoxysilane
2 parts by mass, and
Glycidyl methacrylate 1 part by mass.

The total amount of the radically polymerizable monomers was set to 100 parts by mass. The photochromic compound was added to the radically polymerizable monomers in an amount of 0.27 mmol relative to 100 g of the total amount of the radically polymerizable monomers.

Further, the following additives were added and mixed well to obtain a photochromic curable composition.

Phenylbis(2,4,6-trimethylbenzoyl)phosphine oxide (photopolymerization initiator, Irgacure 819 manufactured by BASF) 0.3 parts by mass, Ethylenebis(oxyethylene)bis[3-(5-tert-butyl-4-hydroxy-m-tolyl)propionate] (stabilizer, Irganox 245 manufactured by Ciba Specialty Chemicals) 1 part by mass, Bis(1,2,2,6,6-pentamethyl-4-piperidyl) sebacate (molecular weight: 508) 3 parts by mass, and Leveling agent (L7001 manufactured by Toray Dow Corning Corp.) 0.1 parts by mass.

Each of the additives was blended in the aforementioned proportion relative to 100 parts by mass of the total amount of the radically polymerizable monomers.

Polymerization was performed by using the aforementioned photochromic curable composition in the following manner by a lamination method to obtain a photochromic laminate (photochromic optical article).

A thiourethane-based plastic lens having a center thickness of 2 mm and a refractive index of 1.60 was used as an optical base material. This thiourethane-based plastic lens was subjected in advance to alkali etching at 50° C. for five minutes with using a 10% aqueous sodium hydroxide solution, and then, washed sufficiently with distilled water.

A spin coater (1H-DX2, manufactured by MIKASA Corporation) was used to coat a moisture-curable primer (product name: TR-SC-P, manufactured by Tokuyama Corporation) on the surface of the aforementioned plastic lens for 15 seconds at a rotational speed of 70 rpm, and then, for 10 seconds at 1000 rpm. Thereafter, about 2 g of the obtained photochromic curable composition was spin-coated for 40 seconds at a rotational speed of 60 rpm, and then, for 10 to 20 seconds at 600 rpm to ensure that the photochromic coating layer had a film thickness of 40 μm.

The lens thus coated with the photochromic curable composition (photochromic coating layer) was irradiated with light for 90 seconds by using a metal halide lamp having a power of 200 $mW/cm^2$ in a nitrogen gas atmosphere to cure the coating film. Thereafter, the lens was further heated at 110° C. for one hour to produce a photochromic laminate having a photochromic layer.

The thus obtained photochromic laminate was evaluated as a sample in the same manner as in Examples 5 to 8. The results are shown in Table 5.

Examples 10 to 12

The operation of Example 9 was carried out in a like manner except for using the compound of Example 2 (Compound 2) in Example 10, the compound of Example 3 (Compound 3) in Example 11, or the compound of Example 4 (Compound 4) in Example 12, thereby producing a photochromic laminate. The photochromic laminate was evaluated in a like manner. The results are shown in Table 5.

TABLE 5

| Example | Compound No. | $L-R^3$ molecular weight | λ max (nm) | $A_{23}$ (−) | $A_{36}$ (−) | $A_{36}/A_{23}$ × 100 (%) | τ 1/2 (sec) |
|---|---|---|---|---|---|---|---|
| 9 | 1 | 178 | 465 | 0.79 | 0.49 | 62% | 102 |
| | | | 570 | 0.57 | 0.35 | 62% | 102 |
| 10 | 2 | 168 | 454 | 0.83 | 0.45 | 53% | 68 |
| | | | 563 | 0.55 | 0.31 | 53% | 68 |
| 11 | 3 | 76 | 452 | 0.79 | 0.44 | 57% | 98 |
| | | | 566 | 0.52 | 0.29 | 57% | 98 |
| 12 | 4 | 76 | 448 | 0.83 | 0.50 | 60% | 108 |
| | | | 560 | 0.54 | 0.33 | 61% | 108 |

Examples 13 to 31

In the same manner as in Example 1, each of propargyl alcohol compounds and naphthol compounds shown in Tables 6 to 9 were reacted with each other to synthesize each of chromene compounds shown in Tables 10 to 15.

TABLE 6

| Example | Propargyl alcohol compound | Napthol compound |
|---|---|---|
| 13 | 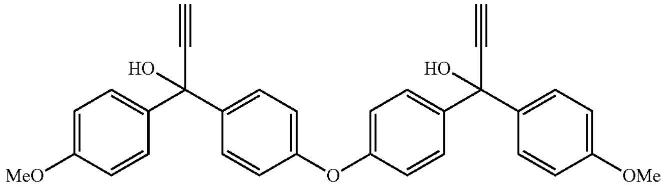 [SMILES: C#CC(O)(c1ccc(OC)cc1)c1ccc(Oc2ccc(C(O)(C#C)c3ccc(OC)cc3)cc2)cc1] | 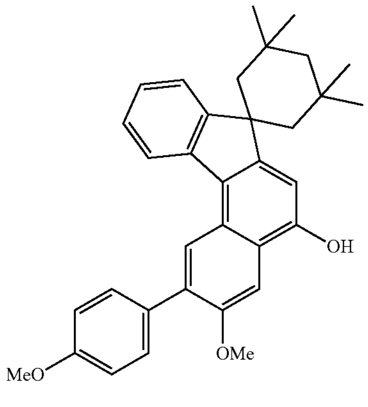 [SMILES: COc1ccc(-c2cc3c4c(cc(O)c3cc2OC)C2(CC(C)(C)CC(C)(C)C2)c2ccccc2-4)cc1] |
| 14 | 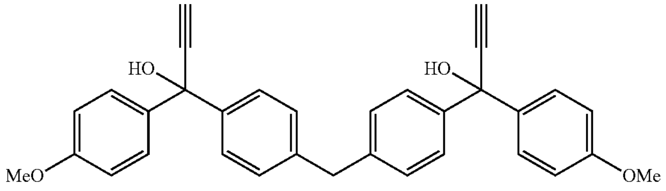 [SMILES: C#CC(O)(c1ccc(Cc2ccc(C(O)(C#C)c3ccc(OC)cc3)cc2)cc1)c1ccc(OC)cc1] | 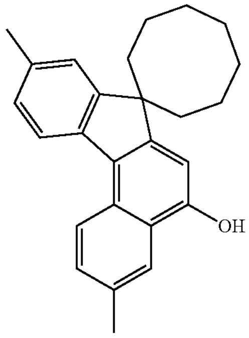 [SMILES: Cc1ccc2c(c1)C1(CCCCCCC1)c1cc(O)c3cc(C)ccc3c1-2] |

TABLE 6-continued
| Example | Propargyl alcohol compound | Napthol compound |
|---|---|---|
| 15 | 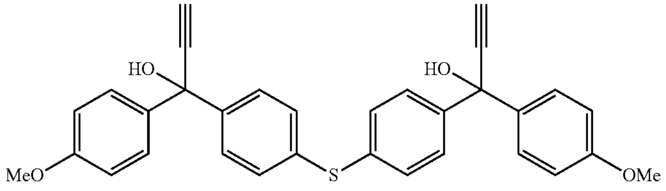 [SMILES: C#CC(O)(c1ccc(OC)cc1)c1ccc(Sc2ccc(C(O)(C#C)c3ccc(OC)cc3)cc2)cc1] | 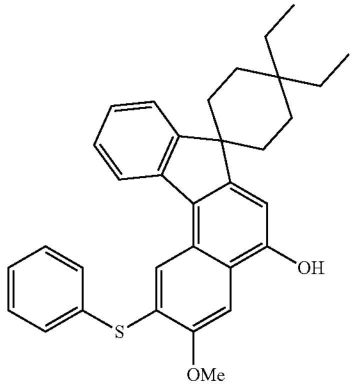 [SMILES: CCC1(CC)CCC2(CC1)c1ccccc1-c1c2cc(O)c2cc(OC)c(Sc3ccccc3)cc12] |
| 16 | 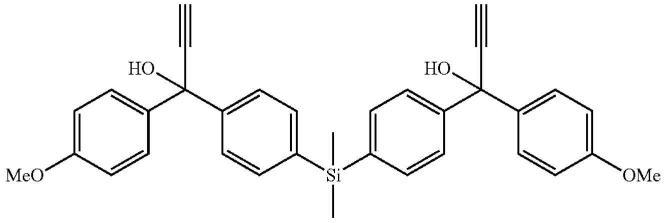 [SMILES: C#CC(O)(c1ccc(OC)cc1)c1ccc([Si](C)(C)c2ccc(C(O)(C#C)c3ccc(OC)cc3)cc2)cc1] | 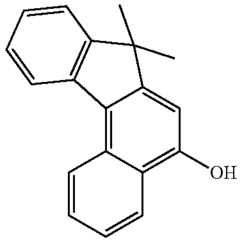 [SMILES: CC1(C)c2ccccc2-c2c1cc(O)c1ccccc21] |
| 17 | 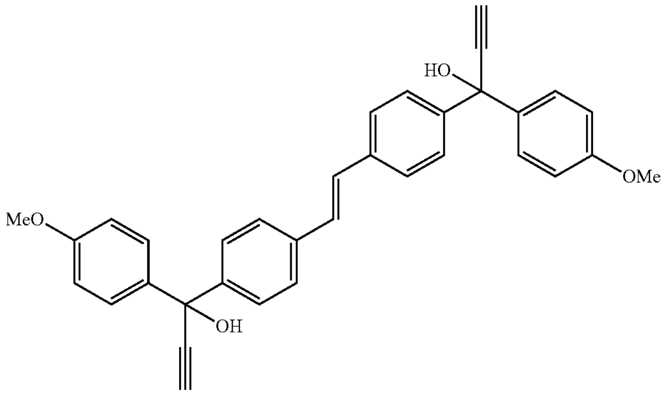 [SMILES: C#CC(O)(c1ccc(/C=C/c2ccc(C(O)(C#C)c3ccc(OC)cc3)cc2)cc1)c1ccc(OC)cc1] | 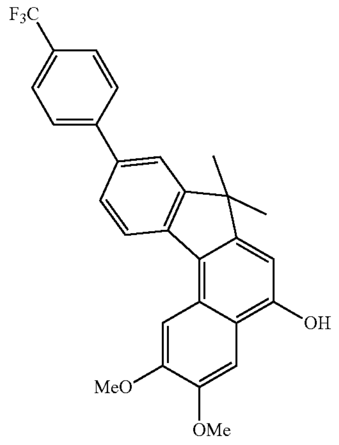 [SMILES: COc1cc2c(O)cc3c(c2cc1OC)-c1ccc(-c2ccc(C(F)(F)F)cc2)cc1C3(C)C] |

TABLE 7
| Example | Propargyl alcohol compound | Napthol compound |
|---|---|---|
| 18 | 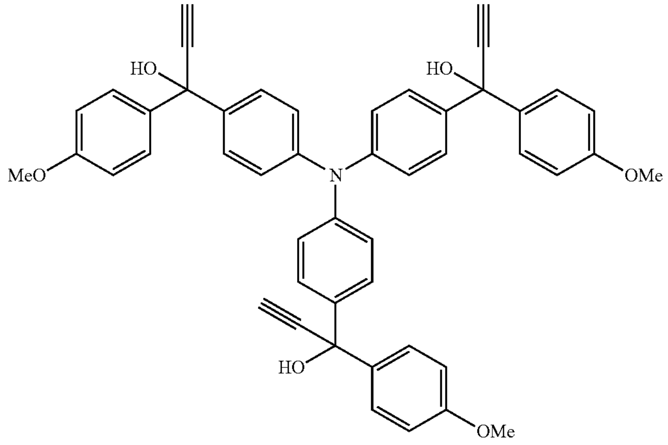 [SMILES: C#CC(O)(c1ccc(OC)cc1)c1ccc(N(c2ccc(C(O)(C#C)c3ccc(OC)cc3)cc2)c2ccc(C(O)(C#C)c3ccc(OC)cc3)cc2)cc1] | 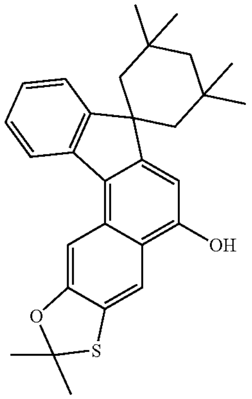 [SMILES: CC1(C)CC(C)(C)CC2(C1)c1ccccc1-c1c2cc(O)c2cc3c(cc12)OC(C)(C)S3] |
| 19 | 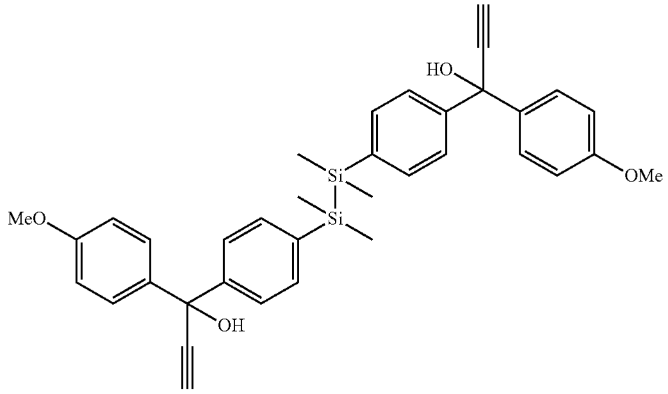 [SMILES: C#CC(O)(c1ccc(OC)cc1)c1ccc([Si](C)(C)[Si](C)(C)c2ccc(C(O)(C#C)c3ccc(OC)cc3)cc2)cc1] | 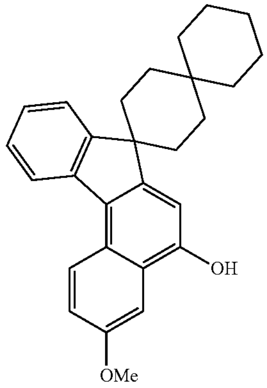 [SMILES: COc1ccc2c3c(cc(O)c2c1)C1(CCC2(CCCCC2)CC1)c1ccccc1-3] |
| 20 | 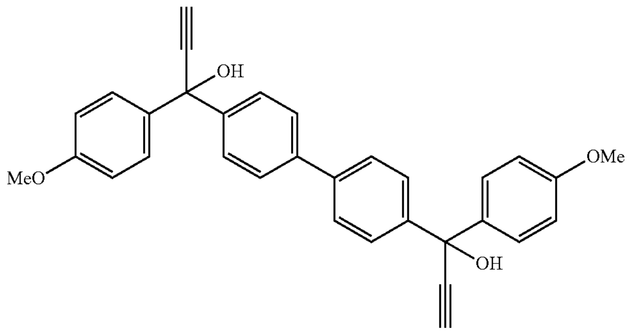 [SMILES: C#CC(O)(c1ccc(OC)cc1)c1ccc(-c2ccc(C(O)(C#C)c3ccc(OC)cc3)cc2)cc1] | 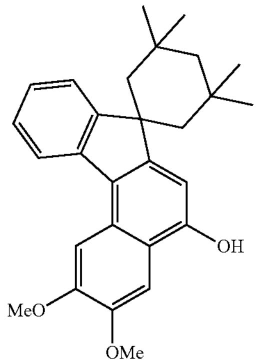 [SMILES: COc1cc2c(O)cc3c(c2cc1OC)-c1ccccc1C31CC(C)(C)CC(C)(C)C1] |
| 21 | 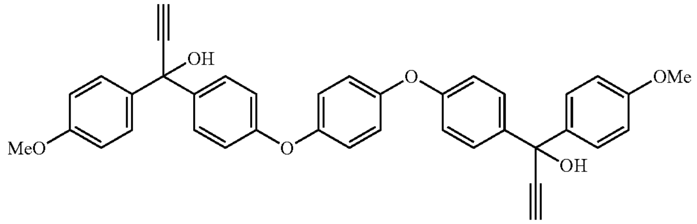 [SMILES: C#CC(O)(c1ccc(OC)cc1)c1ccc(Oc2ccc(Oc3ccc(C(O)(C#C)c4ccc(OC)cc4)cc3)cc2)cc1] | 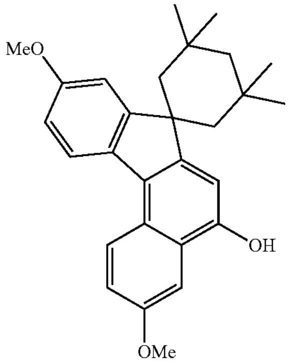 [SMILES: COc1ccc2c(c1)C1(CC(C)(C)CC(C)(C)C1)c1cc(O)c3cc(OC)ccc3c1-2] |

TABLE 7-continued
| Example | Propargyl alcohol compound | Napthol compound |
|---|---|---|
| 22 | 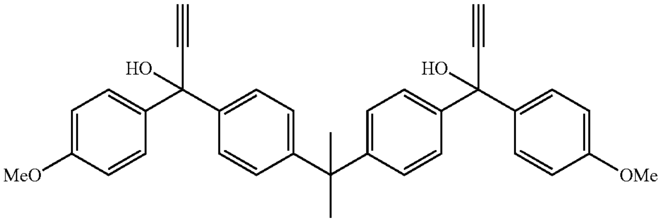 [SMILES: C#CC(O)(c1ccc(OC)cc1)c1ccc(C(C)(C)c2ccc(C(O)(C#C)c3ccc(OC)cc3)cc2)cc1] | 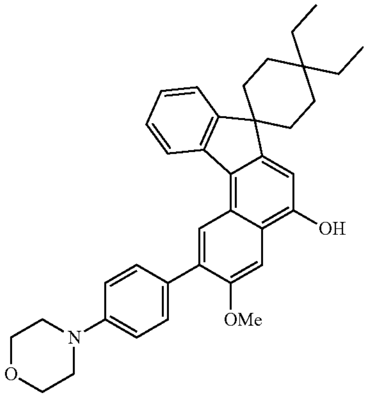 [SMILES: CCC1(CC)CCC2(CC1)c1ccccc1-c1c2cc(O)c2cc(OC)c(-c3ccc(N4CCOCC4)cc3)cc12] |
TABLE 8
| Example | Propargyl alcohol compound | Napthol compound |
|---|---|---|
| 23 | 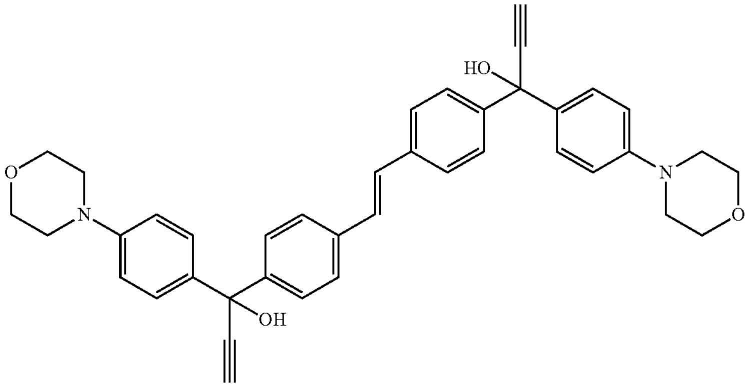 [SMILES: C#CC(O)(c1ccc(/C=C/c2ccc(C(O)(C#C)c3ccc(N4CCOCC4)cc3)cc2)cc1)c1ccc(N2CCOCC2)cc1] | 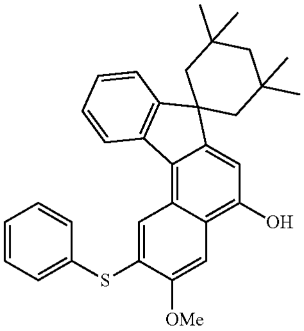 [SMILES: COc1cc2c(O)cc3c(c2cc1Sc1ccccc1)-c1ccccc1C31CC(C)(C)CC(C)(C)C1] |
| 24 | 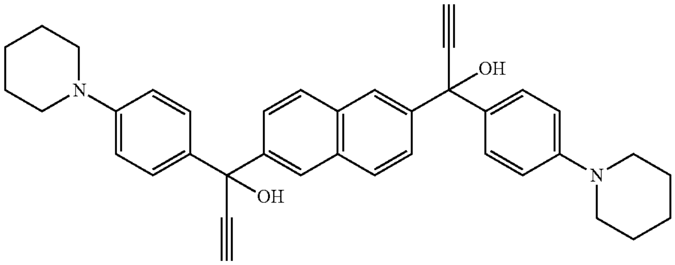 [SMILES: C#CC(O)(c1ccc(N2CCCCC2)cc1)c1ccc2cc(C(O)(C#C)c3ccc(N4CCCCC4)cc3)ccc2c1] | 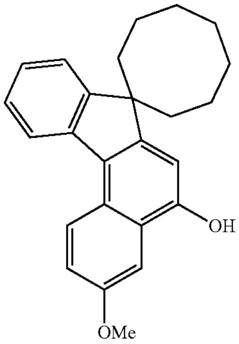 [SMILES: COc1ccc2c3c(cc(O)c2c1)C1(CCCCCCC1)c1ccccc1-3] |
| 25 | 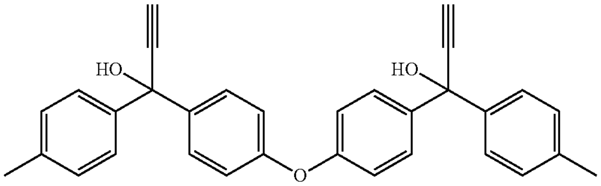 | 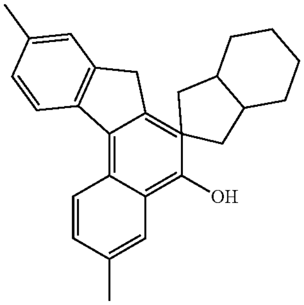 |

TABLE 8-continued
| Example | Propargyl alcohol compound | Napthol compound |
| --- | --- | --- |
| 26 | 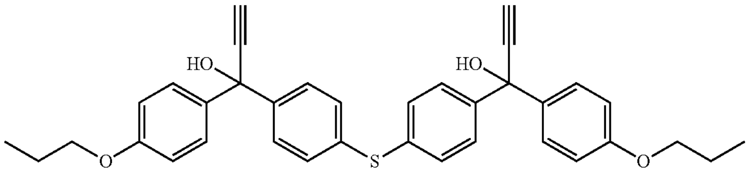 [SMILES: C#CC(O)(c1ccc(OCCC)cc1)c1ccc(Sc2ccc(C(O)(C#C)c3ccc(OCCC)cc3)cc2)cc1] | 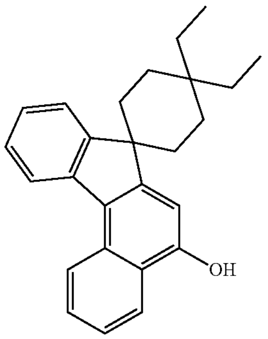 [SMILES: CCC1(CC)CCC2(CC1)c1ccccc1-c1c2cc(O)c2ccccc12] |
| 27 | 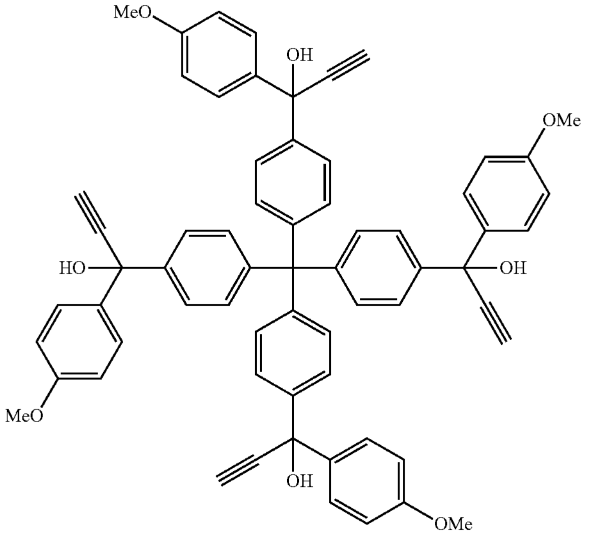 [SMILES: C#CC(O)(c1ccc(OC)cc1)c1ccc(C(c2ccc(C(O)(C#C)c3ccc(OC)cc3)cc2)(c2ccc(C(O)(C#C)c3ccc(OC)cc3)cc2)c2ccc(C(O)(C#C)c3ccc(OC)cc3)cc2)cc1] | 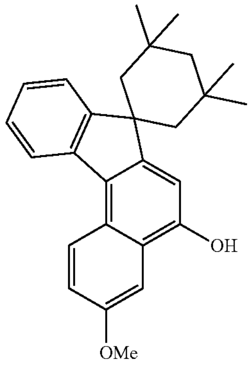 [SMILES: COc1ccc2c3c(cc(O)c2c1)C1(CC(C)(C)CC(C)(C)C1)c1ccccc1-3] |
TABLE 9
| Example | Propargyl alcohol compound | Napthol compound |
| --- | --- | --- |
| 28 | 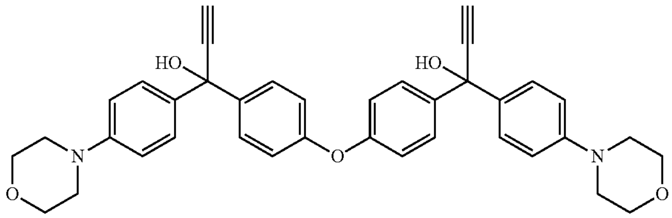 [SMILES: C#CC(O)(c1ccc(Oc2ccc(C(O)(C#C)c3ccc(N4CCOCC4)cc3)cc2)cc1)c1ccc(N2CCOCC2)cc1] | 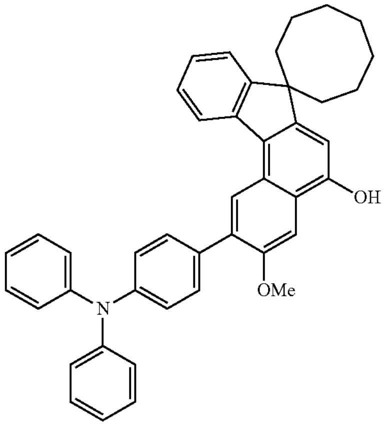 [SMILES: COc1cc2c(O)cc3c(c2cc1-c1ccc(N(c2ccccc2)c2ccccc2)cc1)-c1ccccc1C31CCCCCCC1] |

TABLE 9-continued
| Example | Propargyl alcohol compound | Napthol compound |
| --- | --- | --- |
| 29 | 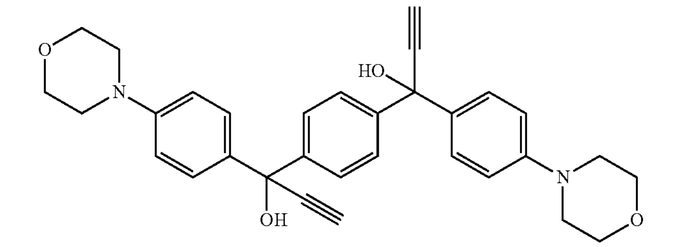 [SMILES: C#CC(O)(c1ccc(N2CCOCC2)cc1)c1ccc(C(O)(C#C)c2ccc(N3CCOCC3)cc2)cc1] | 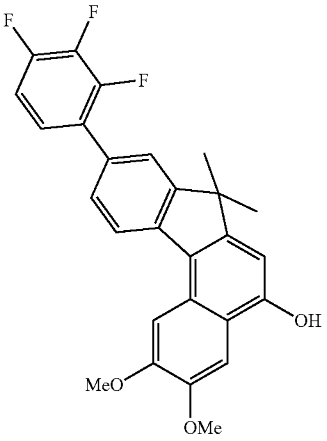 [SMILES: COc1cc2c(O)cc3c(c2cc1OC)-c1ccc(-c2ccc(F)c(F)c2F)cc1C3(C)C] |
| 30 | 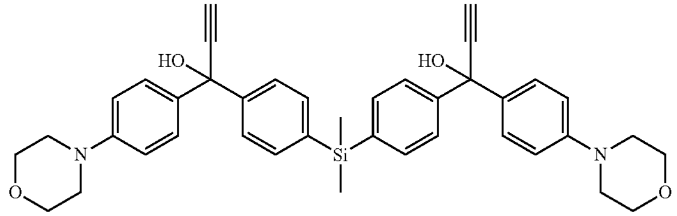 [SMILES: C#CC(O)(c1ccc(N2CCOCC2)cc1)c1ccc([Si](C)(C)c2ccc(C(O)(C#C)c3ccc(N4CCOCC4)cc3)cc2)cc1] | 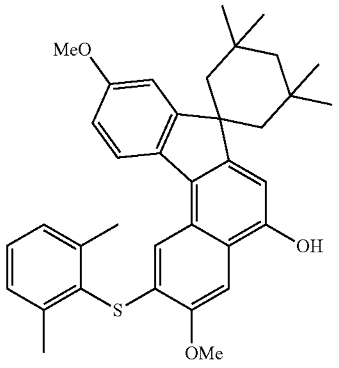 [SMILES: COc1ccc2c(c1)C1(CC(C)(C)CC(C)(C)C1)c1cc(O)c3cc(OC)c(Sc4c(C)cccc4C)cc3c1-2] |
| 31 | 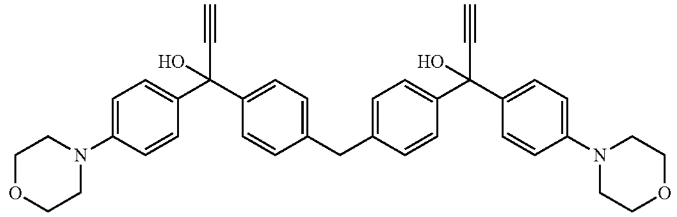 [SMILES: C#CC(O)(c1ccc(Cc2ccc(C(O)(C#C)c3ccc(N4CCOCC4)cc3)cc2)cc1)c1ccc(N2CCOCC2)cc1] | 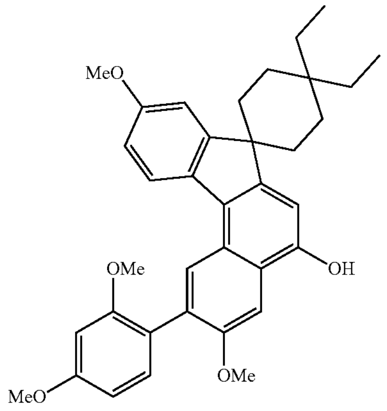 [SMILES: CCC1(CC)CCC2(CC1)c1cc(OC)ccc1-c1c2cc(O)c2cc(OC)c(-c3ccc(OC)cc3OC)cc12] |

TABLE 10
| Example | Photochromic compound |
|---|---|
| 13 | 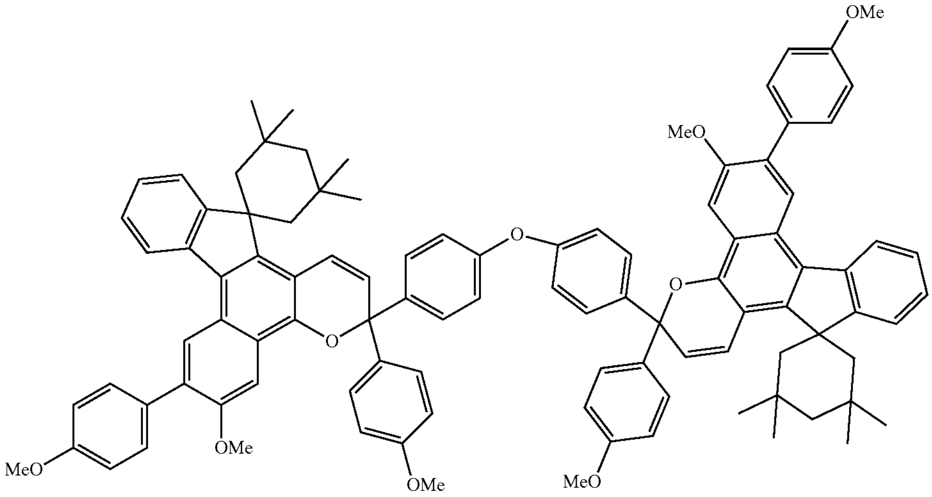 [SMILES: COc1ccc(-c2cc3c4c(c5c(c3cc2OC)OC(c2ccc(OC)cc2)(c2ccc(Oc3ccc(C6(c7ccc(OC)cc7)C=Cc7c8c(c9cc(-c%10ccc(OC)cc%10)c(OC)cc9c7O6)-c6ccccc6C86CC(C)(C)CC(C)(C)C6)cc3)cc2)C=C5)C2(CC(C)(C)CC(C)(C)C2)c2ccccc2-4)cc1] |
| 14 | 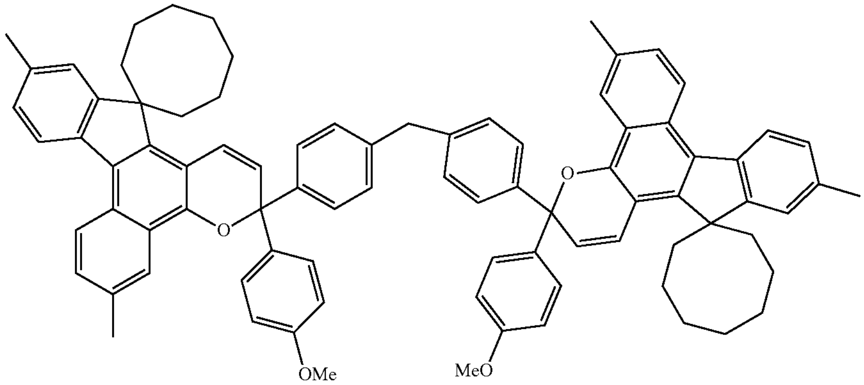 |
| 15 | 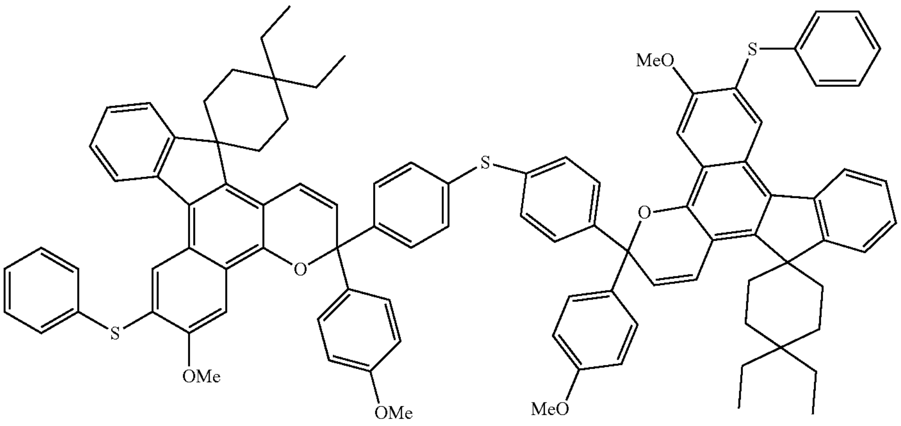 [SMILES: CCC1(CC)CCC2(CC1)c1ccccc1-c1c2c2c(c3cc(OC)c(Sc4ccccc4)cc13)OC(c1ccc(OC)cc1)(c1ccc(Sc3ccc(C4(c5ccc(OC)cc5)C=Cc5c6c(c7cc(Sc8ccccc8)c(OC)cc7c5O4)-c4ccccc4C64CCC(CC)(CC)CC4)cc3)cc1)C=C2] |

TABLE 10-continued
| Example | Photochromic compound |
|---|---|
| 16 | 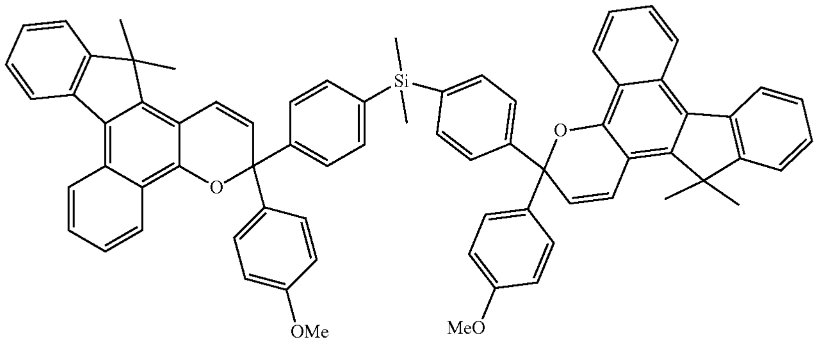 [SMILES: COc1ccc(C2(c3ccc([Si](C)(C)c4ccc(C5(c6ccc(OC)cc6)C=Cc6c7c(c8ccccc8c6O5)-c5ccccc5C7(C)C)cc4)cc3)C=Cc3c4c(c5ccccc5c3O2)-c2ccccc2C4(C)C)cc1] |
TABLE 11
| Example | Photochromic compound |
|---|---|
| 17 | 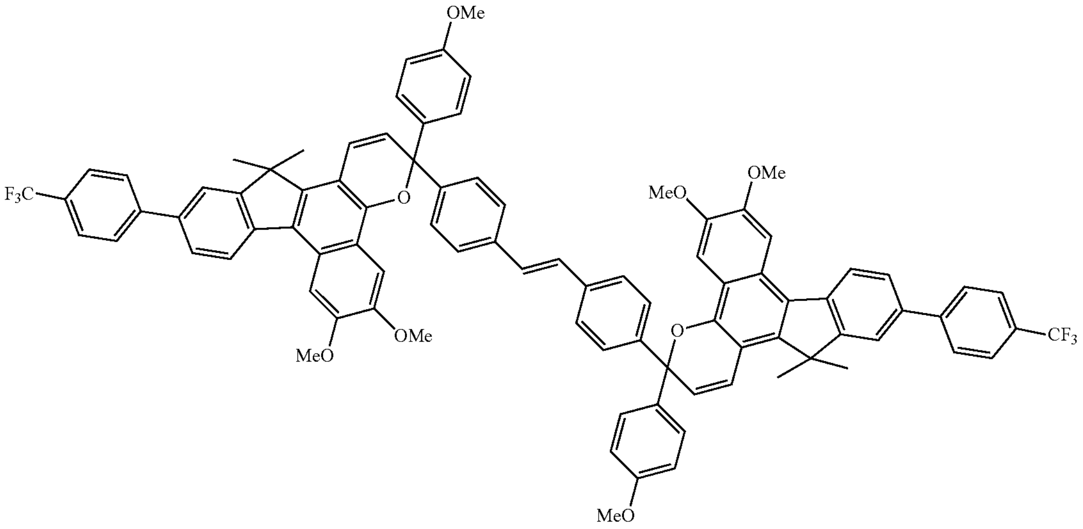 [SMILES: COc1ccc(C2(c3ccc(/C=C/c4ccc(C5(c6ccc(OC)cc6)C=Cc6c7c(c8cc(OC)c(OC)cc8c6O5)-c5ccc(-c6ccc(C(F)(F)F)cc6)cc5C7(C)C)cc4)cc3)C=Cc3c4c(c5cc(OC)c(OC)cc5c3O2)-c2ccc(-c3ccc(C(F)(F)F)cc3)cc2C4(C)C)cc1] |

TABLE 11-continued
| Example | Photochromic compound |
| --- | --- |
| 18 | 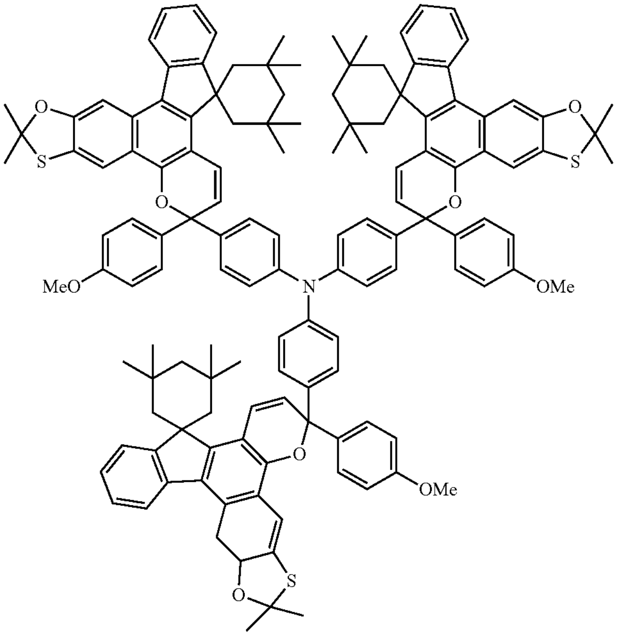 |
| 19 | 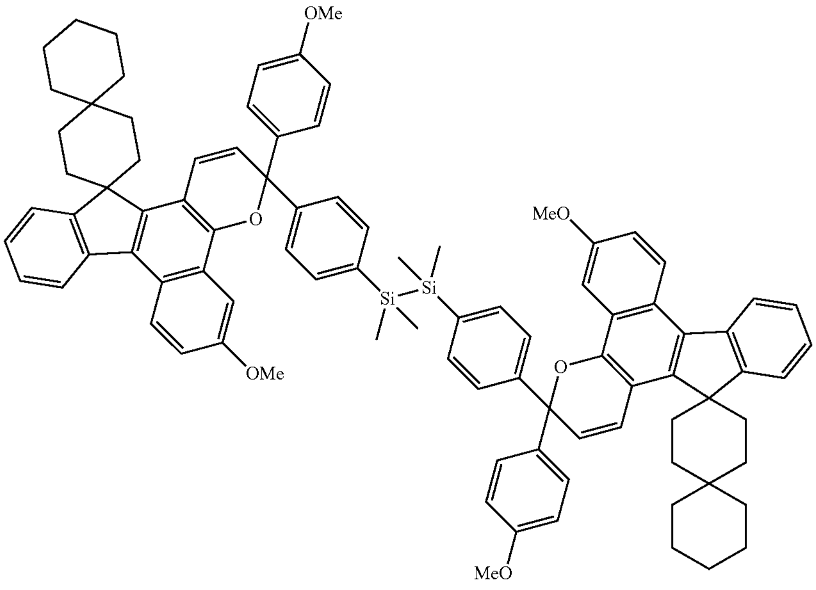 [SMILES: COc1ccc(C2(c3ccc([Si](C)(C)[Si](C)(C)c4ccc(C5(c6ccc(OC)cc6)C=Cc6c7c(c8ccc(OC)cc8c6O5)-c5ccccc5C75CCC6(CCCCC6)CC5)cc4)cc3)C=Cc3c4c(c5ccc(OC)cc5c3O2)-c2ccccc2C42CCC3(CCCCC3)CC2)cc1] |

TABLE 12
| Example | Photochemic compound |
| --- | --- |
| 20 | 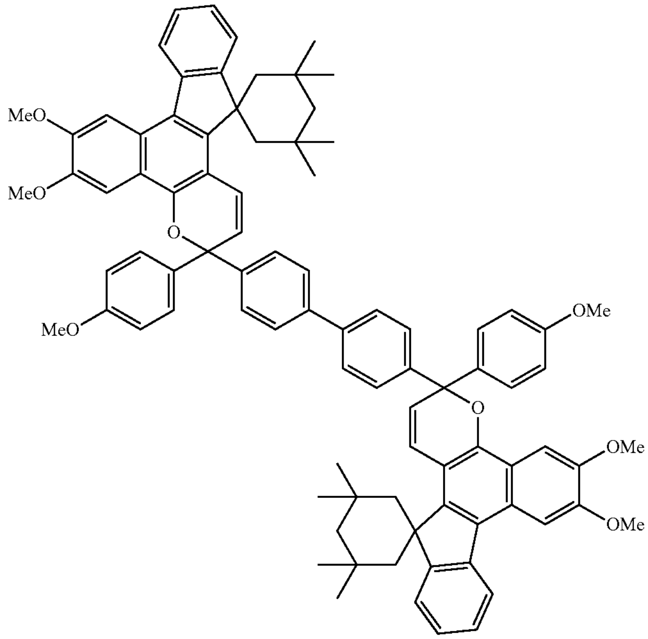 [SMILES: COc1ccc(C2(c3ccc(-c4ccc(C5(c6ccc(OC)cc6)C=Cc6c7c(c8cc(OC)c(OC)cc8c6O5)-c5ccccc5C75CC(C)(C)CC(C)(C)C5)cc4)cc3)C=Cc3c4c(c5cc(OC)c(OC)cc5c3O2)-c2ccccc2C42CC(C)(C)CC(C)(C)C2)cc1] |
| 21 | 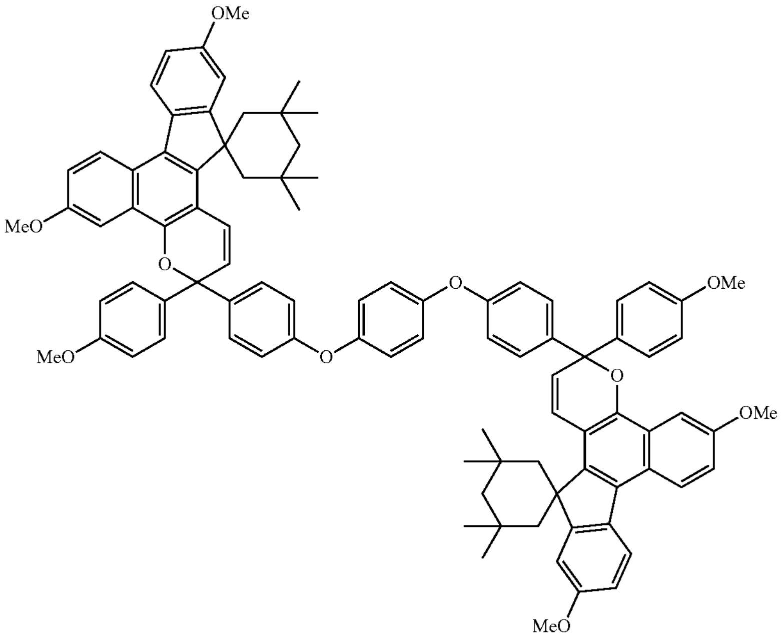 [SMILES: COc1ccc(C2(c3ccc(Oc4ccc(Oc5ccc(C6(c7ccc(OC)cc7)C=Cc7c8c(c9ccc(OC)cc9c7O6)-c6ccc(OC)cc6C86CC(C)(C)CC(C)(C)C6)cc5)cc4)cc3)C=Cc3c4c(c5ccc(OC)cc5c3O2)-c2ccc(OC)cc2C42CC(C)(C)CC(C)(C)C2)cc1] |

TABLE 12-continued
| Example | Photochromic compound |
| --- | --- |
| 22 | 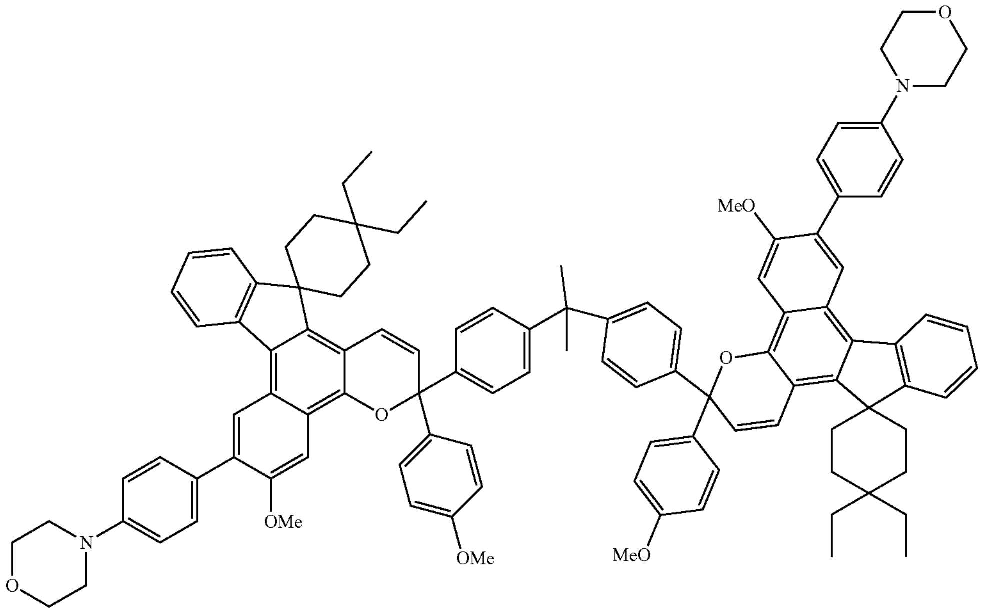 [SMILES: CCC1(CC)CCC2(CC1)c1ccccc1-c1c2c2c(c3cc(OC)c(-c4ccc(N5CCOCC5)cc4)cc13)OC(c1ccc(OC)cc1)(c1ccc(C(C)(C)c3ccc(C4(c5ccc(OC)cc5)C=Cc5c6c(c7cc(-c8ccc(N9CCOCC9)cc8)c(OC)cc7c5O4)-c4ccccc4C64CCC(CC)(CC)CC4)cc3)cc1)C=C2] |
TABLE 13
| Example | Photochromic compound |
| --- | --- |
| 23 | 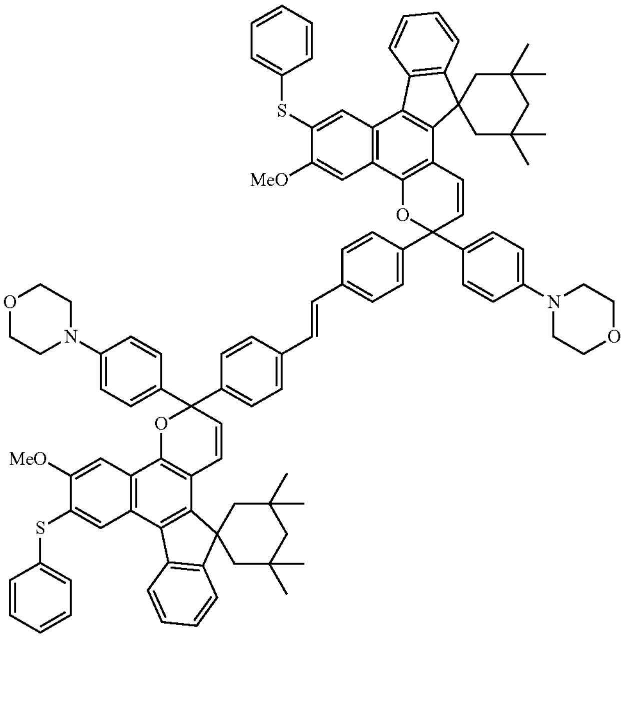 [SMILES: COc1cc2c3c(c4c(c2cc1Sc1ccccc1)-c1ccccc1C41CC(C)(C)CC(C)(C)C1)C=CC(c1ccc(/C=C/c2ccc(C4(c5ccc(N6CCOCC6)cc5)C=Cc5c6c(c7cc(Sc8ccccc8)c(OC)cc7c5O4)-c4ccccc4C64CC(C)(C)CC(C)(C)C4)cc2)cc1)(c1ccc(N2CCOCC2)cc1)O3] |

TABLE 13-continued
| Example | Photochromic compound |
|---|---|
| 24 | 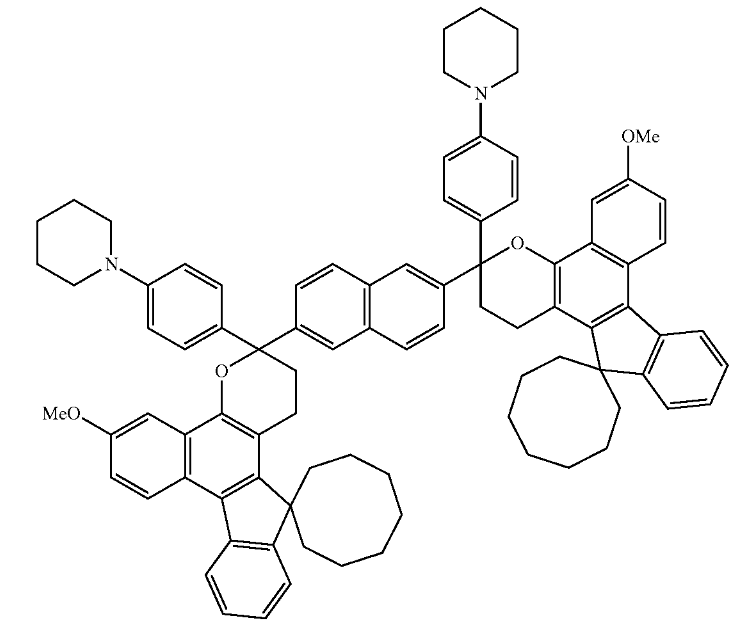 [SMILES: COc1ccc2c3c(c4c(c2c1)OC(c1ccc(N2CCCCC2)cc1)(c1ccc2cc(C5(c6ccc(N7CCCCC7)cc6)CCc6c7c(c8ccc(OC)cc8c6O5)-c5ccccc5C75CCCCCCC5)ccc2c1)CC4)C1(CCCCCCC1)c1ccccc1-3] |
| 25 | 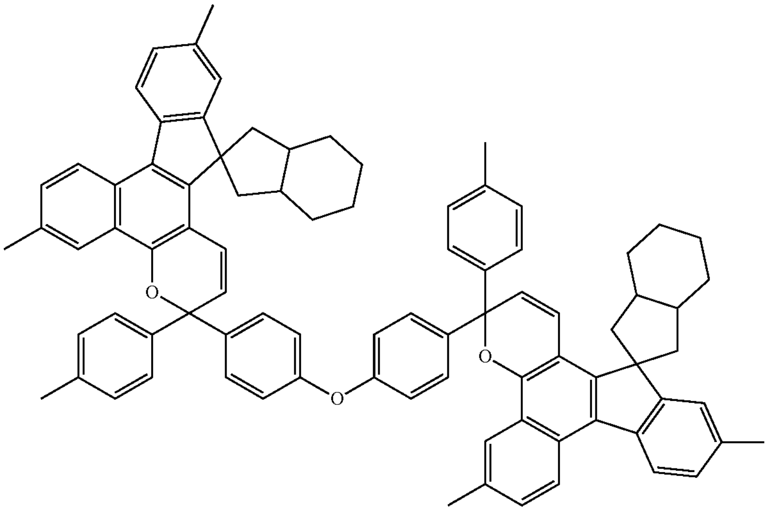 |

TABLE 14
| Example | Photochromic compound |
|---|---|
| 26 | 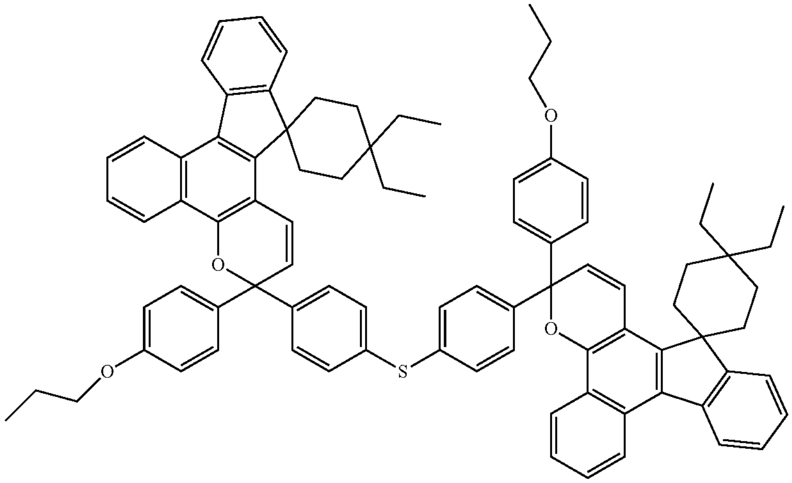 [SMILES: CCCOc1ccc(C2(c3ccc(Sc4ccc(C5(c6ccc(OCCC)cc6)C=Cc6c7c(c8ccccc8c6O5)-c5ccccc5C75CCC(CC)(CC)CC5)cc4)cc3)C=Cc3c4c(c5ccccc5c3O2)-c2ccccc2C42CCC(CC)(CC)CC2)cc1] |
| 27 | 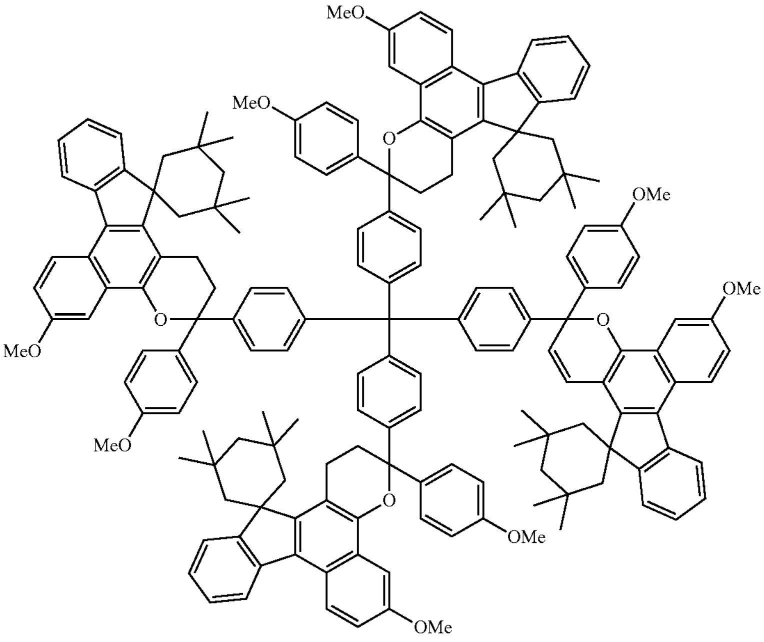 [SMILES: COc1ccc(C2(c3ccc(C(c4ccc(C5(c6ccc(OC)cc6)CCc6c7c(c8ccc(OC)cc8c6O5)-c5ccccc5C75CC(C)(C)CC(C)(C)C5)cc4)(c4ccc(C5(c6ccc(OC)cc6)CCc6c7c(c8ccc(OC)cc8c6O5)-c5ccccc5C75CC(C)(C)CC(C)(C)C5)cc4)c4ccc(C5(c6ccc(OC)cc6)CCc6c7c(c8ccc(OC)cc8c6O5)-c5ccccc5C75CC(C)(C)CC(C)(C)C5)cc4)cc3)C=Cc3c4c(c5ccc(OC)cc5c3O2)-c2ccccc2C42CC(C)(C)CC(C)(C)C2)cc1] |

TABLE 14-continued
| Example | Photochromic compound |
| --- | --- |
| 28 | 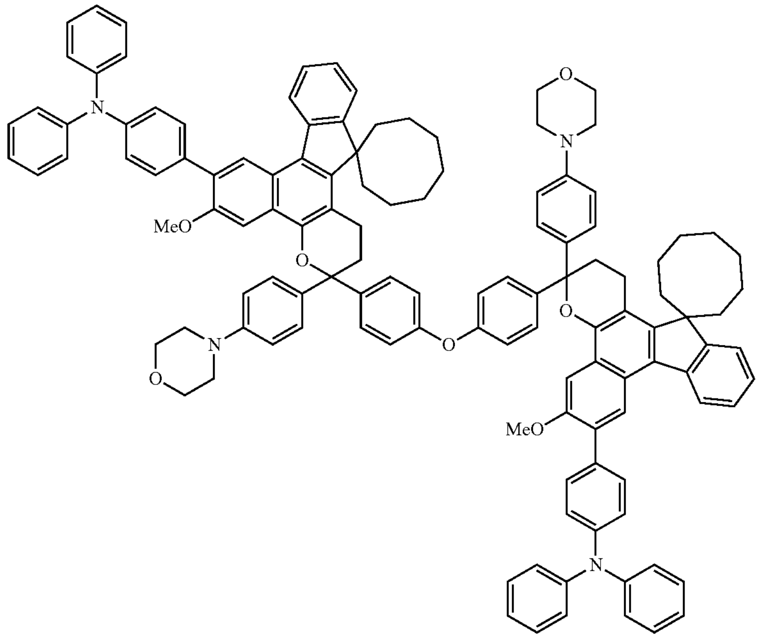 [SMILES: COc1cc2c3c(c4c(c2cc1-c1ccc(N(c2ccccc2)c2ccccc2)cc1)-c1ccccc1C41CCCCCCC1)CCC(c1ccc(Oc2ccc(C4(c5ccc(N6CCOCC6)cc5)CCc5c6c(c7cc(-c8ccc(N(c9ccccc9)c9ccccc9)cc8)c(OC)cc7c5O4)-c4ccccc4C64CCCCCCC4)cc2)cc1)(c1ccc(N2CCOCC2)cc1)O3] |
TABLE 15
| Example | Photochromic compound |
| --- | --- |
| 29 | 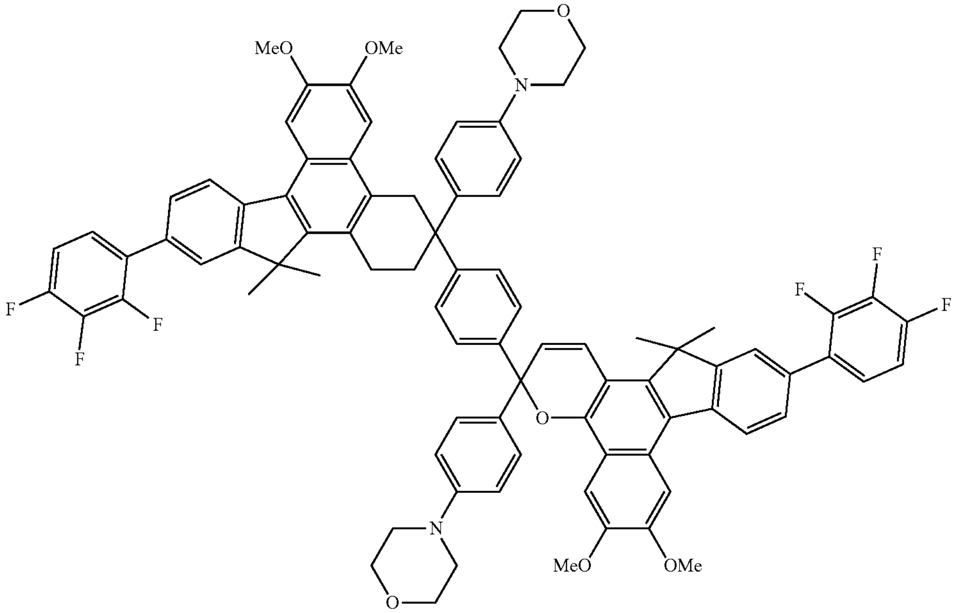 [SMILES: COc1cc2c3c(c4c(c2cc1OC)-c1ccc(-c2ccc(F)c(F)c2F)cc1C4(C)C)CCC(c1ccc(N2CCOCC2)cc1)(c1ccc(C2(c4ccc(N5CCOCC5)cc4)C=Cc4c5c(c6cc(OC)c(OC)cc6c4O2)-c2ccc(-c4ccc(F)c(F)c4F)cc2C5(C)C)cc1)C3] |

TABLE 15-continued

| Example | Photochromic compound |
|---|---|
| 30 | 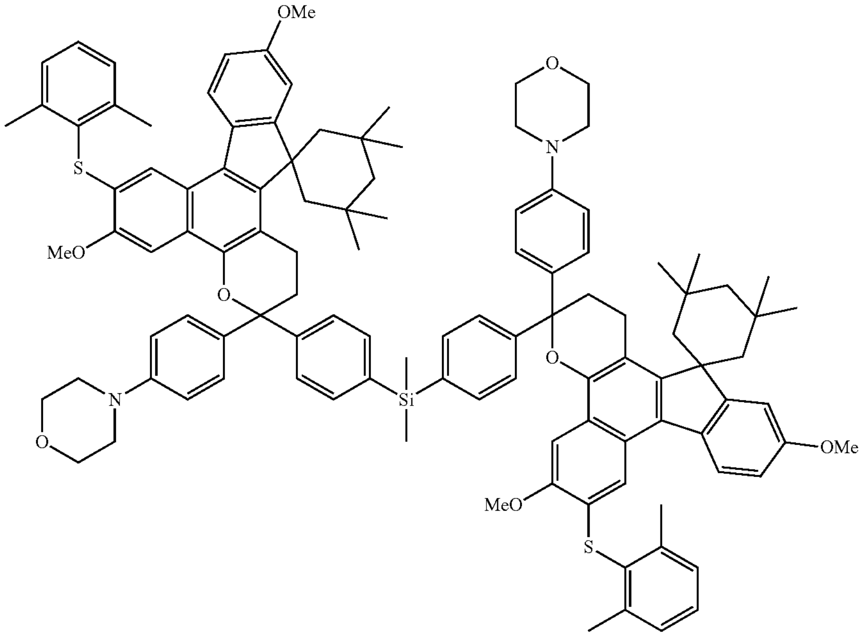 [SMILES: COc1ccc2c(c1)C1(CC(C)(C)CC(C)(C)C1)c1c3c(c4cc(OC)c(Sc5c(C)cccc5C)cc4c1-2)OC(c1ccc(N2CCOCC2)cc1)(c1ccc([Si](C)(C)c2ccc(C4(c5ccc(N6CCOCC6)cc5)CCc5c6c(c7cc(Sc8c(C)cccc8C)c(OC)cc7c5O4)-c4ccc(OC)cc4C64CC(C)(C)CC(C)(C)C4)cc2)cc1)CC3] |
| 31 | 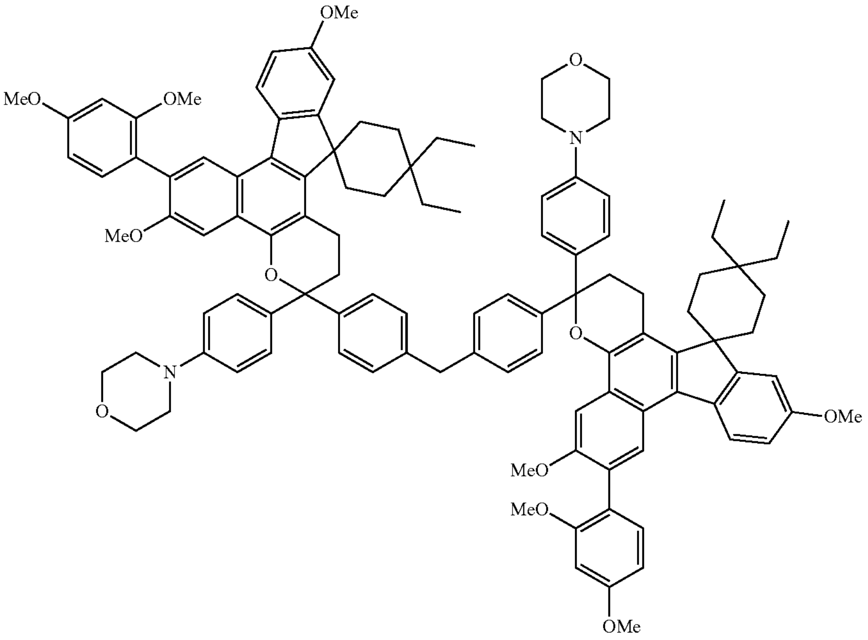 [SMILES: CCC1(CC)CCC2(CC1)c1cc(OC)ccc1-c1c2c2c(c3cc(OC)c(-c4ccc(OC)cc4OC)cc13)OC(c1ccc(Cc3ccc(C4(c5ccc(N6CCOCC6)cc5)CCc5c6c(c7cc(-c8ccc(OC)cc8OC)c(OC)cc7c5O4)-c4ccc(OC)cc4C64CCC(CC)(CC)CC4)cc3)cc1)(c1ccc(N3CCOCC3)cc1)CC2] |

Each of the obtained chromene compounds was subjected to a structural analysis by using the same structure confirmation means as in Example 1. As a result, the chromene compound was identified as the compound represented by each of the structural formulas shown in Tables 10 to 15. Further, Table 16 shows the elemental analysis values of each of the compounds, the calculated values obtained from the structural formula of each of the compounds, and the characteristic $^{1}$H-NMThR spectrum.

TABLE 16

| Example | Compound No. | Calculated value C | H | N | S | Measured value C | H | N | S | ¹H-NMR |
|---|---|---|---|---|---|---|---|---|---|---|
| 13 | 13 | 83.42 | 6.58 | — | — | 83.39 | 6.59 | — | — | δ 0-5.0 ppm, 54 H<br>δ 5.0-9.0 ppm, 40 H |
| 14 | 14 | 87.59 | 6.92 | — | — | 87.61 | 6.91 | — | — | δ 0-5.0 ppm, 48 H<br>δ 5.0-9.0 ppm, 34 H |
| 15 | 15 | 80.62 | 6.21 | — | 6.59 | 80.64 | 6.20 | — | 6.57 | δ 0-5.0 ppm, 48 H<br>δ 5.0-9.0 ppm, 42 H |
| 16 | 16 | 85.00 | 5.94 | — | — | 85.02 | 5.91 | — | — | δ 0-5.0 ppm, 24 H<br>δ 5.0-9.0 ppm, 36 H |
| 17 | 17 | 77.57 | 5.06 | — | — | 77.59 | 5.05 | — | — | δ 0-5.0 ppm, 30 H<br>δ 5.0-9.0 ppm, 40 H |
| 18 | 18 | 80.84 | 6.48 | 0.70 | 4.80 | 80.85 | 6.46 | 0.71 | 4.78 | δ 0-5.0 ppm, 81 H<br>δ 5.0-9.0 ppm, 48 H |
| 19 | 19 | 81.74 | 7.01 | — | — | 81.74 | 7.03 | — | — | δ 0-5.0 ppm, 60 H<br>δ 5.0-9.0 ppm, 34 H |
| 20 | 20 | 83.12 | 6.82 | — | — | 83.15 | 6.81 | — | — | δ 0-5.0 ppm, 54 H<br>δ 5.0-9.0 ppm, 32 H |
| 21 | 21 | 81.83 | 6.58 | — | — | 81.84 | 6.59 | — | — | δ 0-5.0 ppm, 54 H<br>δ 5.0-9.0 ppm, 36 H |
| 22 | 22 | 83.07 | 7.04 | 1.78 | — | 83.08 | 7.03 | 1.79 | — | δ 0-5.0 ppm, 70 H<br>δ 5.0-9.0 ppm, 32 H |
| 23 | 23 | 81.40 | 6.57 | 1.79 | 4.10 | 81.38 | 6.58 | 1.76 | 4.11 | δ 0-5.0 ppm, 58 H<br>δ 5.0-9.0 ppm, 44 H |
| 24 | 24 | 85.54 | 7.02 | 2.27 | — | 85.53 | 7.03 | 2.28 | — | δ 0-5.0 ppm, 54 H<br>δ 5.0-9.0 ppm, 32 H |
| 25 | 25 | 89.08 | 6.78 | — | — | 89.10 | 6.79 | — | — | δ 0-5.0 ppm, 46 H<br>δ 5.0-9.0 ppm, 32 H |
| 26 | 26 | 85.26 | 6.99 | — | 2.59 | 85.29 | 6.97 | — | 2.58 | δ 0-5.0 ppm, 50 H<br>δ 5.0-9.0 ppm, 36 H |
| 27 | 27 | 85.33 | 6.79 | — | — | 85.26 | 6.72 | — | — | δ 0-5.0 ppm, 96 H<br>δ 5.0-9.0 ppm, 68 H |
| 28 | 28 | 84.23 | 6.27 | 3.17 | — | 84.27 | 6.3 | 3.19 | — | δ 0-5.0 ppm, 50 H<br>δ 5.0-9.0 ppm, 60 H |
| 29 | 29 | 75.21 | 5.14 | 2.04 | — | 75.25 | 5.11 | 2.09 | — | δ 0-5.0 ppm, 40 H<br>δ 5.0-9.0 ppm, 30 H |
| 30 | 30 | 78.56 | 6.95 | 1.64 | 3.74 | 78.51 | 6.97 | 1.63 | 3.71 | δ 0-5.0 ppm, 82 H<br>δ 5.0-9.0 ppm, 36 H |
| 31 | 31 | 79.92 | 6.89 | 1.68 | — | 79.88 | 6.91 | 1.65 | — | δ 0-5.0 ppm, 78 H<br>δ 5.0-9.0 ppm, 36 H |

Example 32

First Step:

The reaction of Example 1 of WO 2013/052338 was carried out based on the method described therein except that anisoyl chloride was replaced by a compound of Formula (12) below, thereby obtaining bisbenzophenone represented by Formula (13) below in a yield of 65%.

(12)

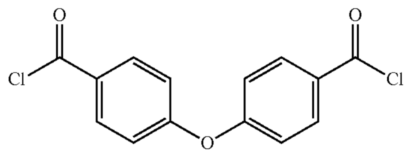

(13)

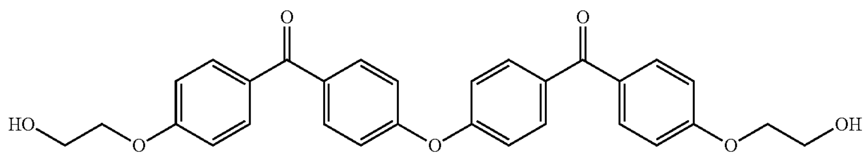

Second Step:

The reaction of Example 1 of the present application was carried out in a like manner except that the bisbenzophenone of Formula (8) used in the third step of Example 1 was replaced by the bisbenzophenone of Formula (13), thereby obtaining a compound represented by Formula (14) below in a yield of 64%.

(14)

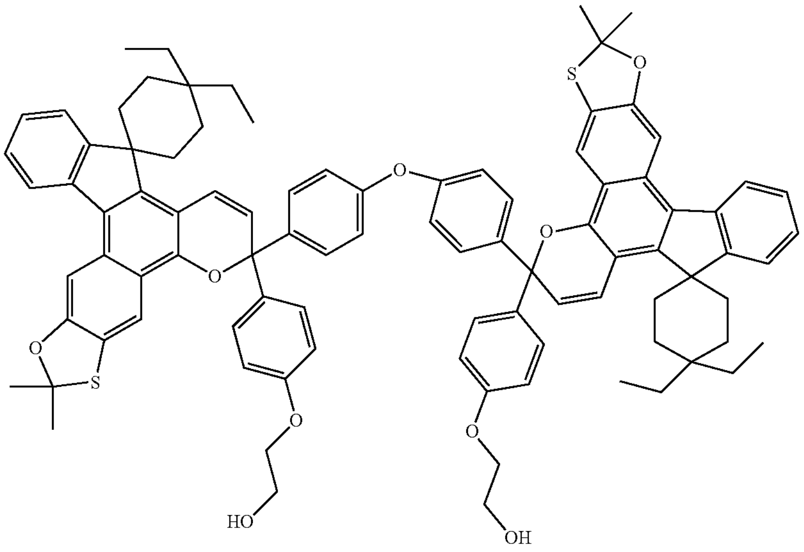

Third Step:

Polyethylene glycol monomethyl ether having a number average molecular weight of 750 75 g (0.10 mol),
succinic anhydride 20 g (0.20 mol),
triethylamine 30.3 g (0.30 mol), and
dichloromethane 1000 mL were mixed and stirred at room temperature for 12 hours. After the reaction was complete, separation was performed by using 10% salt water. An organic layer thus obtained was dried with anhydrous magnesium sulfate. The magnesium sulfate was filtered, and the solvent was distilled off to obtain an oily compound represented by Formula (15) below.

(15)

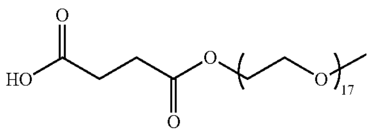

Fourth Step:

The compound (photochromic compound) of Formula (14) obtained in the second step 2.8 g (2.0 mmol),
the compound of Formula (15) obtained in the third step 4.3 g (5.0 mmol), and
dichloromethane 50 ml were mixed and stirred, to which
WSC (water-soluble carbodiimide) 768 mg, and
DMAP (dimethylaminopyridine) 252 mg
were added and stirred for 12 hours while being protected from light. After confirmation by TLC (Thin Layer Chromatography) that there was no material remaining, water was added to stop the reaction. After extraction with toluene, the mixture was concentrated on an evaporator and purified by silica gel chromatography to obtain a photochromic compound represented by Formula (16) below. The yield was 75%.

(16)

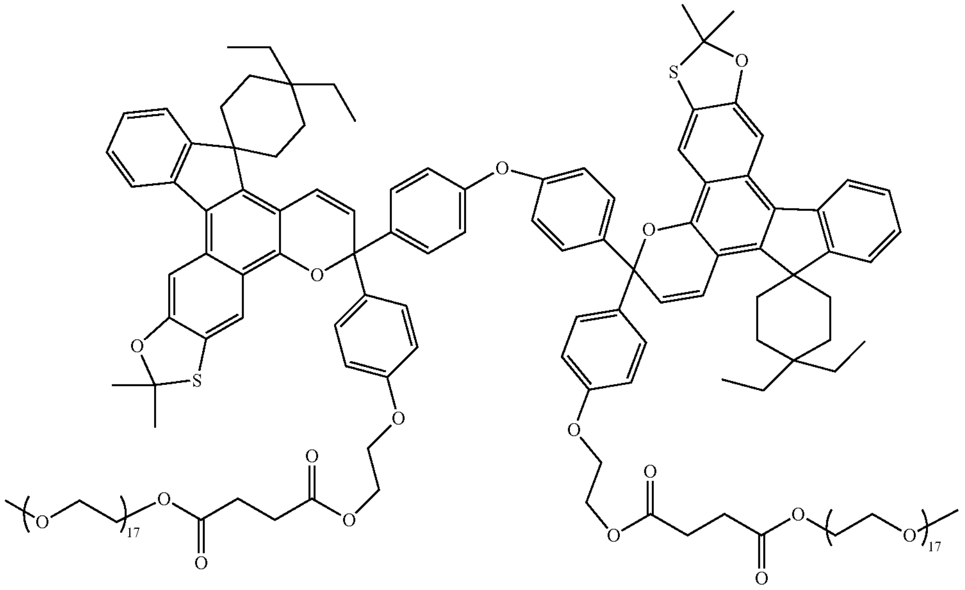

For the aforementioned compound, the proton nuclear magnetic resonance spectrum was measured. The following peaks were observed:

a peak of about 206 H due to cyclohexane rings, ethyl groups, methyl groups, succinic acid moieties, methoxy groups, ethylene glycol moieties, and polyethylene glycol chains at around δ 1.0 to 5.0 ppm; and a peak of 32 H due to aromatic protons and alkene protons at around δ 5.0 to 9.0 ppm.

Example 33

First Step:

The reaction of Example 1 was carried out in a like manner except that the 4,4'-stilbenedicarbonyl chloride was replaced by paraphenylene dicarbonyl chloride, and the anisole was replaced by dimethylaniline, thereby synthesizing a bispropargyl alcohol compound represented by Formula (17) below.

(17)

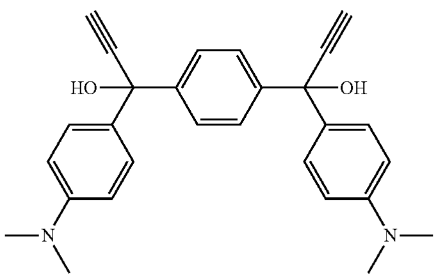

The aforementioned bispropargyl alcohol compound was reacted with a naphthol compound represented by Formula (18) below in the same manner as in Example 1 to obtain a photochromic compound represented by Formula (19) below in a yield of 50%.

(18)

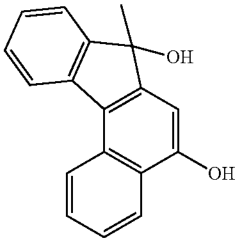

(19)

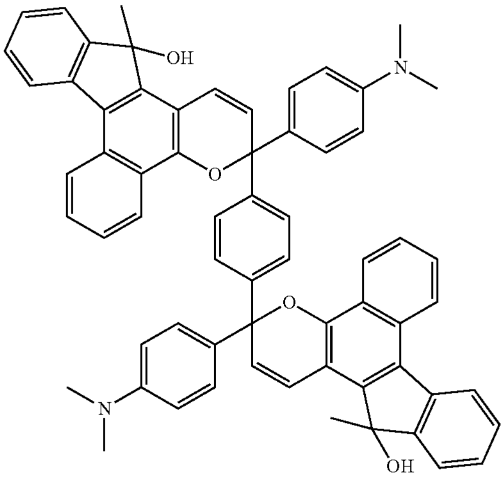

Second Step:

The same operation as in the third step of Example 32 was carried out except that the polyethylene glycol monomethyl ether having a number average molecular weight of 750 was replaced by a compound represented by Formula (20) below having a number average molecular weight of 1100, thereby obtaining a compound represented by Formula (21) below.

(20)

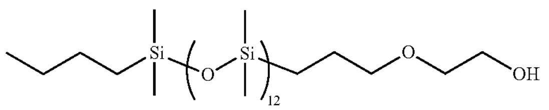

(21)

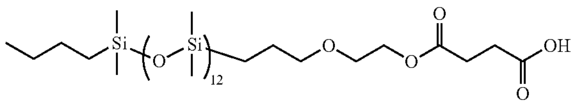

Third Step:

The operation of the fourth step of Example 32 was carried out in a like manner except that the compounds of Formulas (14) and (15) were replaced by the compounds of Formulas (19) and (21), respectively, thereby obtaining a photochromic compound represented by Formula (22) below. The yield was 79%.

The results are shown in Tables 17 and 18. Example 53 used the compound synthesized in Example 32 (Compound 32), and Example 54 used the compound synthesized in Example 33 (Compound 33).

TABLE 17

| Example | Compound No. | L-$R^3$ molecular weight | λ max (nm) | $A_{23}$ (-) | $A_{36}$ (-) | $A_{36}$/$A_{23}$ × 100 (%) | τ 1/2 (sec) |
|---|---|---|---|---|---|---|---|
| 34 | 13 | 168 | 443 | 0.59 | 0.33 | 56% | 56 |
| | | | 567 | 0.54 | 0.30 | 56% | 56 |
| 35 | 14 | 166 | 431 | 0.66 | 0.43 | 65% | 156 |
| | | | 553 | 1.14 | 0.74 | 65% | 156 |
| 36 | 15 | 184 | 458 | 1.03 | 0.77 | 75% | 192 |
| | | | 568 | 0.74 | 0.55 | 74% | 192 |
| 37 | 16 | 210 | 425 | 0.57 | 0.39 | 69% | 114 |
| | | | 549 | 0.91 | 0.64 | 69% | 114 |
| 38 | 17 | 178 | 459 | 1.21 | 0.98 | 81% | 237 |
| | | | 581 | 0.77 | 0.62 | 80% | 238 |
| 39 | 18 | 242 | 590 | 0.26 | 0.14 | 56% | 45 |

(22)

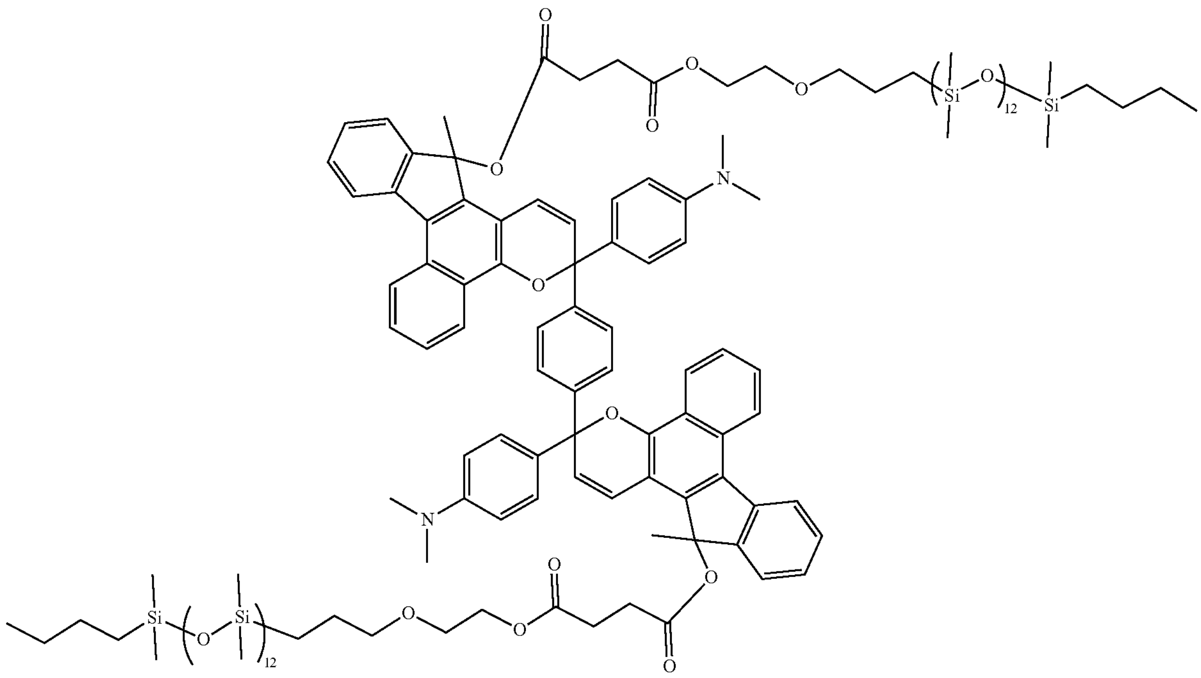

For the aforementioned photochromic compound, the proton nuclear magnetic resonance spectrum was measured. The following peaks were observed:

a peak of about 208 H due to methyl groups, ethylene glycol moieties, succinic acid moieties, propyl groups, diethylamino groups, and polydimethylsiloxane chains at around δ 1.0 to 5.0 ppm; and a peak of 32 H due to aromatic protons and alkene protons at around δ 5.0 to 9.0 ppm.

Examples 34 to 54

The operation of Example 9 was carried out in a like manner except for using each of the compounds shown in Tables 10 to 15, thereby producing a photochromic laminate. The photochromic laminate was evaluated in a like manner.

TABLE 17-continued

| Example | Compound No. | L-$R^3$ molecular weight | λ max (nm) | $A_{23}$ (-) | $A_{36}$ (-) | $A_{36}$/$A_{23}$ × 100 (%) | τ 1/2 (sec) |
|---|---|---|---|---|---|---|---|
| 40 | 19 | 268 | 436 | 0.54 | 0.34 | 62% | 115 |
| | | | 560 | 0.89 | 0.56 | 63% | 116 |
| 41 | 20 | 152 | 446 | 0.72 | 0.40 | 55% | 65 |
| | | | 557 | 0.49 | 0.27 | 55% | 65 |
| 42 | 21 | 260 | 423 | 0.37 | 0.24 | 64% | 124 |
| | | | 580 | 0.60 | 0.39 | 66% | 123 |
| 43 | 22 | 194 | 455 | 1.01 | 0.80 | 79% | 165 |
| | | | 559 | 0.77 | 0.61 | 79% | 165 |
| 44 | 23 | 178 | 490 | 0.44 | 0.27 | 62% | 57 |
| | | | 595 | 0.47 | 0.29 | 61% | 56 |

TABLE 17-continued

| Example | Compound No. | L-$R^3$ molecular weight | λ max (nm) | $A_{23}$ (−) | $A_{36}$ (−) | $A_{36}$/$A_{23}$ × 100 (%) | τ 1/2 (sec) |
|---|---|---|---|---|---|---|---|
| 45 | 24 | 126 | 595 | 1.03 | 0.71 | 69% | 121 |
| 46 | 25 | 168 | 429 | 0.44 | 0.26 | 59% | 86 |
| | | | 548 | 0.91 | 0.54 | 59% | 86 |
| 47 | 26 | 184 | 427 | 0.37 | 0.23 | 62% | 64 |
| | | | 541 | 0.74 | 0.46 | 62% | 64 |

TABLE 18

| Example | Compound No. | L-$R^3$ molecular weight | λ max (nm) | $A_{23}$ (−) | $A_{36}$ (−) | $A_{36}$/$A_{23}$ × 100 (%) | τ 1/2 (sec) |
|---|---|---|---|---|---|---|---|
| 48 | 27 | 316 | 420 | 0.19 | 0.12 | 61% | 160 |
| | | | 564 | 0.31 | 0.19 | 61% | 161 |
| 49 | 28 | 168 | 484 | 0.81 | 0.6 | 74% | 135 |
| | | | 587 | 0.86 | 0.64 | 74% | 136 |
| 50 | 29 | 76 | 470 | 0.80 | 0.59 | 75% | 171 |
| | | | 595 | 0.66 | 0.49 | 75% | 170 |
| 51 | 30 | 210 | 470 | 0.56 | 0.37 | 66% | 91 |
| | | | 600 | 0.58 | 0.38 | 66% | 91 |
| 52 | 31 | 166 | 462 | 0.57 | 0.36 | 63% | 132 |
| | | | 583 | 0.78 | 0.49 | 63% | 132 |
| 53 | 32 | 168 | 454 | 0.79 | 0.41 | 53% | 56 |
| | | | 567 | 0.52 | 0.28 | 53% | 56 |
| 54 | 33 | 76 | 584 | 0.54 | 0.26 | 48% | 43 |

Example 55

(Physical Property Evaluation of Photochromic Plastic Lens Produced by Binder Method)

A photochromic layer was produced by the following method.

Preparation of Terminal Non-Reactive Urethane Urea Resin:

A 2 L four-neck flask fitted with a stirring blade, a condenser, a thermometer, and a nitrogen gas inlet tube was charged with polycarbonate diol having a number average molecular weight of 700 220 parts by mass, isophorone diisocyanate 100 parts by mass, and toluene 72 parts by mass for reaction in a nitrogen atmosphere at 100° C. for seven hours, thereby synthesizing a urethane prepolymer having an isocyanate group at the terminal.

After the synthesis of the urethane prepolymer, the reaction solution was cooled to approximately 0° C. and dissolved in 205 parts by mass of isopropyl alcohol and 382 parts by mass of diethyl ketone, and then, the temperature of this solution was held at 0° C.

Then, a mixed solution of 23 parts by mass of bis-(4-aminocyclohexyl)methane as a chain extender and 20 parts by mass of diethyl ketone was added dropwise within 30 minutes and allowed to react at 0° C. for one hour.

Thereafter, 5.7 parts by mass of 1,2,2,6,6-pentamethyl-4-aminopiperidine was further added dropwise and allowed to react at 0° C. for one hour to obtain a diethyl ketone solution of a terminal non-reactive urethane urea resin.

Preparation of Composition for Forming Photochromic Layer:

Relative to 100 parts by mass of the solid content of the obtained solution of the terminal non-reactive urethane urea resin, an isomer mixture of 4,4'-methylenebis(cyclohexylisocyanate) (polyisocyanate compound) 4 parts by mass, ethylenebis(oxyethylene)bis[3-(5-tert-butyl-4-hydroxy-m-tolyl)propionate] (antioxidant) 0.4 parts by mass, and a surfactant (DOW CORNING TORAY L-7001) 0.06 parts by mass were added to the solution.

Further, the photochromic compound synthesized in Example 1 (Compound 1: 0.26 mmol) was added per 100 g of the solid content, followed by stirring and mixing at room temperature to obtain a composition for forming a photochromic layer.

Synthesis of Adhesive for Adhesive Layer (Terminal Non-Reactive Urethane Urea Resin):

A 5 L four-neck separable flask fitted with a stirring blade, a condenser, a thermometer, and a nitrogen gas inlet tube was prepared and charged with polycarbonate diol having a number average molecular weight of 1000 400 parts by mass, isophorone diisocyanate 175 parts by mass, and toluene 120 parts by mass for reaction in a nitrogen atmosphere at 110° C. for seven hours, thereby synthesizing a urethane prepolymer having an isocyanate group at the terminal.

After the completion of the reaction, the reaction solution was cooled to approximately 20° C., dissolved in 2500 parts by mass of propylene glycol-monomethylether, and then, the temperature of this liquid was kept at 20° C.

Then, 60 parts by mass of isophoronediamine as a chain extender was added dropwise and allowed to react at 20° C. for one hour. Thereafter, 3 parts by mass of n-butylamine was further added dropwise and allowed to react at 20° C. for one hour to obtain a propylene glycol-monomethylether solution of a terminal non-reactive urethane urea resin.

To 500 parts by mass of the obtained terminal non-reactive urethane urea resin solution, a surfactant (DOW CORNING TORAY L-7001)

0.2 parts by mass was added, followed by stirring and mixing at room temperature to obtain an adhesive for an adhesive layer.

Production of Photochromic Laminate:

A coater (manufactured by Tester Sangyo Co., Ltd.) was used to coat the adhesive for an adhesive layer on polycarbonate sheets (first and second optical sheets: one of them would make an optical base material and the other would make a layer free of photochromic compounds) having a thickness of 400 μm at a coating rate of 0.5 m/min, followed by drying at a drying temperature of 110° C. for three minutes so as to obtain a polycarbonate sheet having an adhesive resin layer with a film thickness of 5 μm.

Next, a coater (manufactured by Tester Sangyo Co., Ltd.) was used to coat the composition for forming a photochromic layer on an OPP film (stretched polypropylene film) having a thickness of 50 μm at a coating rate of 0.3 m/min, followed by drying at a drying temperature of 100° C. for five minutes, thereby forming a photochromic layer. Thereafter, the photochromic layer (thickness: 40 μm) was placed on the adhesive resin layer of the first optical sheet and bonded to the adhesive resin layer.

The thus prepared laminate comprised the first optical sheet, the adhesive resin layer, the photochromic layer and the OPP film in this order. The OPP film was peeled off from this laminate, and the resultant structural body was bonded to the polycarbonate sheet (second optical sheet) having the adhesive resin layer so that the photochromic layer and the adhesive resin layer on the polycarbonate sheet (second optical sheet) were joined together.

Next, the obtained laminate was left to stand at 40° C. for 24 hours under vacuum, which was then heat-treated at 110°

C. for 60 minutes, and further subjected to a humidification treatment at 60° C. and 100% RH for 24 hours. Finally, the laminate was left to stand at 40° C. for 24 hours under vacuum, whereby a photochromic laminate was obtained.

The obtained photochromic laminate was evaluated as a sample in the same manner as in Example 5. The results are shown in Table 19.

Examples 56 to 59

The operation of Example 55 was carried out in a like manner except for using each of the photochromic compounds shown in Table 19, thereby producing a photochromic laminate. The photochromic laminate was evaluated in a like manner. The results are shown in Table 19.

The results show that excellent temperature dependence is also achieved by the use of the binder method.

TABLE 19

| Example | Compound No. | L-$R^3$ molecular weight | λ max (nm) | $A_{23}$ (−) | $A_{36}$ (−) | $A_{36}$/$A_{23}$ × 100 (%) | τ 1/2 (sec) |
|---|---|---|---|---|---|---|---|
| 55 | 1 | 178 | 467 | 0.77 | 0.50 | 63% | 132 |
| | | | 568 | 0.56 | 0.35 | 63% | 132 |
| 56 | 13 | 168 | 441 | 0.58 | 0.19 | 57% | 67 |
| | | | 568 | 0.53 | 0.30 | 58% | 67 |
| 57 | 18 | 242 | 588 | 0.25 | 0.14 | 57% | 52 |
| 58 | 24 | 126 | 596 | 1.01 | 0.71 | 70% | 142 |
| 59 | 29 | 76 | 472 | 0.79 | 0.60 | 76% | 198 |
| | | | 592 | 0.64 | 0.49 | 76% | 199 |

Example 60

(Physical Property Evaluation of Photochromic Plastic Lens Produced by Bonding Method (Lamination Method))

A photochromic curable composition was prepared according to the following formulation, and the composition was cast and polymerized on the surface of a lens base material.

Preparation of Curable Composition:

According to the following formulation, the respective components were thoroughly mixed to prepare a polymerizable composition:

1,3-Bis(isocyanatomethyl)cyclohexane 38.3 parts by mass,

Pentaerythritoltetrakis(3-mercaptopropionate) 42.5 parts by mass,

Tridecanel-thiol 2.9 parts by mass,

Polyoxyethylene polyoxypropylene monododecyl ether (number average molecular weight: 1200) 12.3 parts by mass, and RX-1 4.0 parts by mass.

RX-1 is a polyrotaxane monomer synthesized by the method described in the third step of Example 1 in WO2018/235771 (i.e., pr1; see Reference Example 1 in WO 2018/235771).

The total of the thus prepared polymerizable composition was 100 parts by mass.

In 100 parts by mass of the total of the polymerizable composition, 0.05 parts by mass of dimethyldichlorotin was blended.

Further, the photochromic compound synthesized in Example 2 (Compound 2) was added to ensure that it would be 0.1 mmol relative to 100 g of the total of the polymerizable composition, thereby preparing a photochromic curable composition.

Production of Photochromic Laminate:

The photochromic curable composition was used to obtain a photochromic laminate by a bonding method. The polymerization method is described below.

The photochromic curable composition was sufficiently defoamed, and then, it was injected into a mold in which a glass plate and a thiourethane-based plastic lens having a refractive index of 1.60 were provided with a gap of 1 mm therebetween, thereby polymerizing a photochromic curable composition by cast polymerization.

The polymerization was performed for 18 hours at a temperature gradually raised from 27° C. to 120° C. for curing.

After the polymerization, only the glass plate was removed, resulting in a laminated photochromic optical article having a 1 mm-thick photochromic layer laminated on the thiourethane-based plastic lens having a refractive index of 1.60.

The thus obtained photochromic laminate was evaluated as a sample in the same manner as in Example 5. The results are shown in Table 20.

Examples 61 to 63

The operation of Example 60 was carried out in a like manner except for using each of the photochromic compounds shown in Table 20, thereby producing a photochromic laminate. The photochromic laminate was evaluated in a like manner. The results are shown in Table 20.

TABLE 20

| Example | Compound No. | L-$R^3$ molecular weight | λ max (nm) | $A_{23}$ (−) | $A_{36}$ (−) | $A_{36}$/$A_{23}$ × 100 (%) | τ 1/2 (sec) |
|---|---|---|---|---|---|---|---|
| 60 | 2 | 168 | 455 | 0.85 | 0.46 | 54% | 78 |
| | | | 569 | 0.56 | 0.36 | 54% | 78 |
| 61 | 3 | 76 | 451 | 0.82 | 0.48 | 59% | 112 |
| | | | 573 | 0.54 | 0.31 | 58% | 113 |
| 62 | 15 | 184 | 459 | 1.07 | 0.82 | 77% | 216 |
| | | | 573 | 0.76 | 0.58 | 77% | 216 |
| 63 | 30 | 210 | 470 | 0.58 | 0.39 | 67% | 100 |
| | | | 605 | 0.59 | 0.40 | 67% | 100 |

Example 64, Comparative Examples 4 and 5

(Evaluation of Weather Resistance)

3 mL of a toluene solution of the photochromic compound (Compound 3) synthesized in Example 3 (in which the photochromic basic structural group is present at a concentration of 1 mmol/L), together with a stirring bar, was put in a 6 mL vial bottle and sealed. Then, the toluene solution was irradiated with simulated sunlight at a temperature in a range of 23° C. to 24° C. for 10 minutes by using XENON LAMP POWER SUPPLY MODEL YSS-50 manufactured by Yamashita Denso Corporation, while being stirred in the bottle turned sideways. The toluene solution before and after the irradiation was analyzed by using a high performance liquid chromatogram (HPLC), and the survival rate was calculated from the following equation.

Survival rate (%)=(area of photochromic compound after 10-minute irradiation)/(area of photochromic compound before irradiation)×100

The higher the survival rate, the better the weather resistance.

For comparison, the same evaluation as in Example 64 was made of the compound represented by Formula (B) and a compound represented by Formula (D) below in which an organic group having an S-containing aromatic ring serves as a bonding group (Comparative Examples 4 and 5). Here, the compound of Formula (D) was synthesized based on Examples of JP 2005-508897 A. The results are shown in Table 21.

(D)

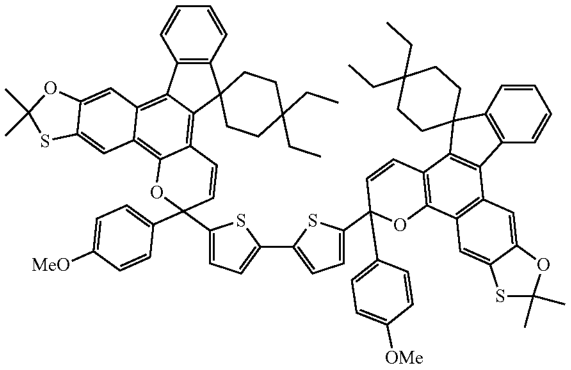

TABLE 21

| | Compound No. | Survival rate (%) |
|---|---|---|
| Example 64 | 3 | 98 |
| Comparative Example 4 | B | 99 |
| Comparative Example 5 | D | 82 |

As is evident from Table 21, the photochromic compound of the present invention has excellent weather resistance as compared with the photochromic compound in which an organic group having an S-containing aromatic ring serves as a bonding group.

The invention claimed is:

1. A photochromic compound represented by Formula (1) below comprising at least two of monovalent photochromic basic structural groups PC, the monovalent photochromic basic structural group including a T-type photochromic moiety and being bonded to an organic group having a non-SO aromatic ring containing neither a sulfur atom nor an oxygen atom, $$[PC-L]_m-R^3 \quad (1)$$

where m is an integer of 2 to 6,

PC is the monovalent photochromic basic structural group, provided that at least one of L and $R^3$ contains the non-SO aromatic ring, L is a phenylene group or a direct bonding, $R^3$ is an m-valent organic group or a direct bonding, and when $R^3$ is a direct bonding, m is two and L is a divalent organic group containing the non-SO aromatic ring, wherein the m-valent organic group $R^3$ is selected from the group consisting of a saturated or unsaturated hydrocarbon group having 1 to 15 carbon atoms; a saturated or unsaturated aliphatic ring group that has 3 to 20 carbon atoms and may have a heteroatom in the aliphatic ring; a polyvalent silylene group that has 1 to 3 silicon atoms and has, as a substituent, at least one selected from an alkyl group having 1 to 15 carbon atoms, an alkoxy group having 1 to 15 carbon atoms, or a non-SO aromatic ring group having 6 to 30 carbon atoms; and an oxygen atom or a sulfur atom when m=2; or a carbon atom when m=4, wherein an organic group including the group $R^3$ bonded to the PC has a molecular weight per PC of less than 300, and wherein each monovalent photochromic basic structural group PC is represented by Formula (2) below:

(2)

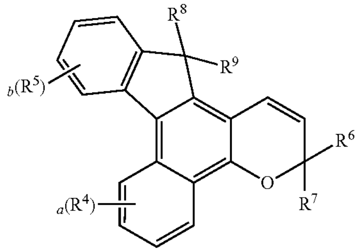

where a is an integer of 0 to 4, b is an integer of 0 to 4, $R^4$ and $R^5$ are each the following group:

a hydroxyl group;
an alkyl group;
a cycloalkyl group;
an alkoxy group;
an amino group;
a cyano group;
a halogen atom;
a nitro group;
a formyl group;
a hydroxycarbonyl group;
an alkylcarbonyl group;
an alkoxycarbonyl group;
an aryl group;
a heterocyclic group;
an alkylthio group;
a cycloalkylthio group;
an arylthio group;
an aralkyl group;
an aralkoxy group;
an aryloxy group;
a thiol group;
an alkoxyalkylthio group;
a group represented by Formula (X) below:

(X)

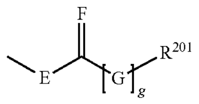

where E is an oxygen atom or $NR^{101}$ where $R^{101}$ is a hydrogen atom or an alkyl group, F is an oxygen atom or a sulfur atom, $R^{201}$ is a hydrogen atom, an alkyl group, or a cycloalkyl group, G is an oxygen atom, a sulfur atom, or $NR^{202}$ where $R^{202}$ is a hydrogen atom, an alkyl group, a cycloalkyl group, an aryl group, or a heteroaryl group, and when G is an oxygen atom or a sulfur atom, $R^{201}$ is a group other than a hydrogen atom, and g is an integer of 0 or 1; or a group represented by formula (Y) below:

(Y)

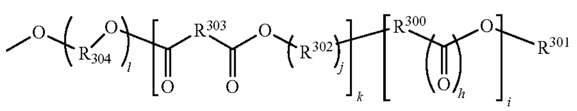

where $R^{300}$ is an alkylene group or a silylene group having an alkyl group or an aryl group as a substituent, $R^{301}$ is an alkyl group or an aryl group, $R^{302}$, $R^{303}$ and $R^{304}$ are each an alkylene group, h, j, k and 1 are each an integer of 0 or 1, and i is an integer of 2 to 200; the plural i may be expressed in the same or different units, when a plurality of the $R^4$ or $R^5$ are present depending on the value of a or b, the plural $R^4$ or $R^5$ may be the same or different from each other; when two $R^4$ or $R^5$ are present adjacent to each other, these two adjacent $R^4$ or $R^5$ together may form, with carbon atoms to which the $R^4$ or $R^5$ are bonded, a ring that may contain an oxygen atom, a carbon atom, a sulfur atom, or a nitrogen atom, $R^6$ is a phenylene group or a direct bonding and $R^7$ is an aryl group or a heteroaryl group or a direct bonding, provided that one of the $R^6$ and $R^7$ is a direct bonding to an organic group, $R^8$ and $R^9$ are each the following group:

a hydrogen atom;
a hydroxyl group;
an alkyl group;
a cycloalkyl group;
an alkoxy group;
an alkoxyalkyl group;
a formyl group;
a hydroxycarbonyl group;
an alkylcarbonyl group;
an alkoxycarbonyl group;
a halogen atom;
an aralkyl group;
an aralkoxy group;
an aryl group;
an aryloxy group;
a heterocyclic group; or
the group represented by Formula (Y), and the $R^8$ and $R^9$ together may form, with carbon atoms in the 13-position to which the $R^8$ and $R^9$ are bonded, an aliphatic ring having 3 to 20 carbon atoms, a fused polycyclic ring in which the aliphatic ring is fused with an aromatic ring or an aromatic heterocyclic ring, a 3- to 20-membered heterocyclic ring, or a fused polycyclic ring in which the heterocyclic ring is fused with an aromatic ring or an aromatic heterocyclic ring, and wherein a non-SO aromatic ring is an aromatic hydrocarbon ring or an aromatic heterocyclic ring containing neither a sulfur atom(S) nor an oxygen atom (O) therein, and wherein $R^3$ has a molecular weight of less than 200.

2. The photochromic compound according to claim 1, wherein the $R^8$ and $R^9$ in Formula (2) together form, with the carbon atoms in the 13-position to which the $R^8$ and $R^9$ are bonded, an aliphatic ring having 3 to 20 carbon atoms, a fused polycyclic ring in which the aliphatic ring is fused with an aromatic ring or an aromatic heterocyclic ring, a 3 to 20 membered heterocycle ring, or a fused polycyclic ring in which the heterocyclic ring is fused with an aromatic ring or an aromatic heterocyclic ring.

3. The photochromic compound according to claim 2, wherein the aliphatic ring formed by the $R^8$ and $R^9$ in Formula (2) together is a cyclopentane ring, a cyclohexane ring, a cycloheptane ring, a cyclooctane ring, a cyclononane ring, a cyclodecane ring, a cycloundecane ring, a cyclododecane ring, or a spirodicyclohexane ring, and the ring may have one to ten alkyl groups having 1 to 3 carbon atoms or cycloalkyl groups having 5 to 7 carbon atoms as substituents or may be fused with a cycloalkyl group having 5 to 7 carbon atoms.

4. A photochromic curable composition comprising a photochromic compound according to claim 1 and a polymerizable compound.

5. A photochromic optical article formed by polymerization of a photochromic curable composition according to claim 4.

6. A polymer molded article in which a photochromic compound according to claim 1 is dispersed.

7. An optical article coated with a polymer film in which a photochromic compound according to claim 1 is dispersed.

* * * * *